(12) United States Patent
Nakamura et al.

(10) Patent No.: US 8,039,420 B2
(45) Date of Patent: Oct. 18, 2011

(54) FUNGICIDAL COMPOSITION CONTAINING ACID AMIDE DERIVATIVE

(75) Inventors: Yuji Nakamura, Kusatsu (JP); Shigeru Mitani, Kusatsu (JP); Tetsuo Yoneda, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 0 days.

(21) Appl. No.: 12/822,204

(22) Filed: Jun. 24, 2010

(65) Prior Publication Data

US 2010/0261735 A1    Oct. 14, 2010

Related U.S. Application Data

(62) Division of application No. 11/659,423, filed as application No. PCT/JP2005/014970 on Aug. 10, 2005, now Pat. No. 7,829,501.

(30) Foreign Application Priority Data

Aug. 12, 2004  (JP) ................................ 2004-235634
Jun. 17, 2005  (JP) ................................ 2005-178614

(51) Int. Cl.
*A01N 43/56* (2006.01)
*A01N 43/10* (2006.01)
*A01N 43/08* (2006.01)
(52) U.S. Cl. .................... 504/280; 504/289; 504/299
(58) Field of Classification Search .................. 504/257, 504/337, 312, 280
See application file for complete search history.

(56) References Cited

U.S. PATENT DOCUMENTS

| | | | |
|---|---|---|---|
| 7,439,366 B2 | 10/2008 | Nakamura et al. | |
| 7,683,096 B2 | 3/2010 | Nakamura et al. | |
| 2003/0153464 A1 | 8/2003 | Nakamura et al. | |
| 2004/0254237 A1 | 12/2004 | Nakamura et al. | |
| 2010/0093707 A1 | 4/2010 | Nakamura et al. | |

FOREIGN PATENT DOCUMENTS

| | | |
|---|---|---|
| CN | 1353700 A | 6/2002 |
| CN | 1423631 A | 6/2003 |
| EP | 0 334 134 | 9/1989 |
| EP | 1 256 569 | 11/2002 |
| EP | 1 428 817 | 6/2004 |
| JP | 2005-179234 | 7/2005 |
| WO | 00/73290 | 12/2000 |
| WO | 01/60783 A1 | 8/2001 |
| WO | 03/027059 A1 | 4/2003 |
| WO | 2004/005478 | 1/2004 |

OTHER PUBLICATIONS

"Pesticide," [retrieved on Aug. 12, 2010]. Retrieved online via Internet, URL: http://en.wikipedia.org/wiki/Pesticide.*
Hayes, F. Newton et al., "2, 5-Diaryloxazoles and 2,5-Diaryl-1,3,4-oxadiazoles", Journal of the American Chemical Society, vol. 77, pp. 1850-1852, 1955.
Shkumat, A. P. et al., "2-(2-furyl)- and 2-(2-thienyl)-5-aryloxazoles", Ukrainskii Khimicheskii Zhurnal (Russian Edition), vol. 53, No. 5, pp. 529-533, 1987. (English abstract only).
RN 128370-89-8; CAPLUS retrieved on Jul. 2, 2009.
RN 237384-68-8; CAPLUS retrieved on Jul. 2, 2009.
RN 389123-02-8; CAPLUS retrieved on Jul. 2, 2009.
RN 478489-82-6; CAPLUS retrieved on Jul. 2, 2009.
RN 133380-43-5; CAPLUS retrieved on Jul. 2, 2009.
RN 99923-42-9; CAPLUS retrieved on Jul. 2, 2009.
RN 112671-98-4 CAPLUS retrieved on Jul. 2, 2009.
U.S. Appl. No. 12/822,206, filed Jun. 24, 2010, Nakamura et al.
U.S. Appl. No. 12/095,517, filed May 30, 2008, Nakamura et al.

* cited by examiner

*Primary Examiner* — Kamal Saeed
*Assistant Examiner* — Kristin Bianchi
(74) *Attorney, Agent, or Firm* — Oblon, Spivak, McClelland, Maier & Neustadt, L.L.P.

(57) ABSTRACT

Conventional many fungicidal compositions have had practical problems such that either a preventive effect or a curing effect is inadequate, the residual effect tends to be inadequate, or the controlling effect against plant diseases tends to be inadequate depending upon the application site, and a fungicidal composition to overcome such problems has been desired. The present invention provides a fungicidal composition containing an acid amide derivative of the formula (I) or a salt thereof, as an active ingredient:

(I)

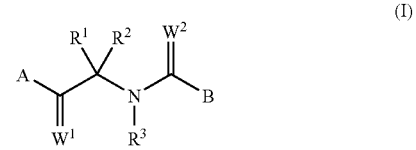

wherein A is phenyl which may be substituted, benzyl which may be substituted, naphthyl which may be substituted, heterocyclic ring which may be substituted, fused heterocyclic ring which may be substituted, or the like; B is heterocyclic ring which may be substituted, fused heterocyclic ring which may be substituted, or naphthyl which may be substituted; each of $R^1$ and $R^2$ which are independent of each other, is alkyl, or the like; $R^3$ is hydrogen, or the like; each of $W^1$ and $W^2$ which are independent of each other, is oxygen or sulfur.

20 Claims, No Drawings

FUNGICIDAL COMPOSITION CONTAINING ACID AMIDE DERIVATIVE

This is a divisional application of U.S. application Ser. No. 11/659,423, filed Feb. 5, 2007, which is a 371 of PCT/JP2005/014970 filed on Aug. 10, 2005.

TECHNICAL FIELD

The present invention relates to a fungicidal composition containing an acid amide derivative.

BACKGROUND ART

WO2001/60783 and WO2003/27059 disclose that acid amide derivatives having certain chemical structures are useful as active ingredients for pesticides, but there is no disclosure that compounds of the formula (I) given hereinafter, have fungicidal activities. On the other hand, Japanese Patent Application No. 2003-420864 by the present applicants, discloses a fungicidal composition containing an acid amide derivative as an active ingredient, but the active ingredient compound of such a composition is different from the compound of the formula (I) given hereinafter.

Conventional many fungicidal compositions have had practical problems such that either a preventive effect or a curing effect is inadequate, the residual effect tends to be inadequate, or the controlling effect against plant diseases tends to be inadequate depending upon the application site. Accordingly, a fungicidal composition to overcome such problems has been desired.

DISCLOSURE OF THE INVENTION

The present inventors have conducted a research to solve the above problems and as a result, have found that a fungicidal composition containing an acid amide derivative of the formula (I) given hereinafter exhibits excellent preventive and curing effects against various diseases caused by various noxious fungi such as Oomycetes, Ascomycetes, Basidiomycetes or Deuteromycetes and, at the same time, has practically satisfactory residual activities. The present invention has been accomplished on the basis of this discovery.

Namely, the present invention provides a fungicidal composition containing an acid amide derivative of the formula (I) or a salt thereof as an active ingredient:

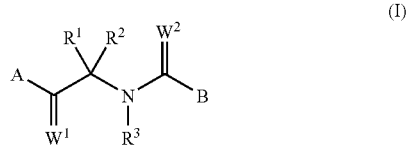

(I)

wherein A is phenyl which may be substituted by X, benzyl which may be substituted by X, naphthyl which may be substituted by X, heterocyclic ring which may be substituted by X, fused heterocyclic ring which may be substituted by X, indanyl (the indanyl may be substituted by halogen, alkyl, or alkoxy), or tetrahydronaphthyl (the tetrahydronaphthyl may be substituted by halogen, alkyl, or alkoxy); B is heterocyclic ring (excluding pyridyl) which may be substituted by Y, fused heterocyclic ring which may be substituted by Y, or naphthyl which may be substituted by Y; X is halogen, alkyl which may be substituted by $E^1$, alkenyl which may be substituted by $E^1$, alkynyl which may be substituted by $E^1$, hydroxy, cyanooxy, alkoxy which may be substituted by $E^1$, alkenyloxy which may be substituted by $E^1$, alkynyloxy which may be substituted by $E^1$, mercapto, cyanothio, alkylthio which may be substituted by $E^1$, alkenylthio which may be substituted by $E^1$, alkynylthio which may be substituted by $E^1$, alkylsulfinyl which may be substituted by $E^2$, alkylsulfonyl which may be substituted by $E^2$, cycloalkyl which may be substituted by J, cycloalkyloxy which may be substituted by J, cycloalkylthio which may be substituted by J, cyano, nitro, formyl, phenyl which may be substituted by Y, phenoxy which may be substituted by Y, phenylthio which may be substituted by Y, phenylalkyl which may be substituted by Y, phenylalkenyl which may be substituted by Y, phenylalkynyl which may be substituted by Y, phenylalkyloxy which may be substituted by Y, phenylalkenyloxy which may be substituted by Y, phenylalkynyloxy which may be substituted by Y, phenylalkylthio which may be substituted by Y, phenylalkenylthio which may be substituted by Y, phenylalkynylthio which may be substituted by Y, phenylamino which may be substituted by Y, —$OR^4$, —$SR^5$, —$NR^6R^7$, —$CO_2R^8$, —$C(=O)NR^8R^9$, —$SO_2NR^8R^9$, —$CH=NR^{10}$, or heterocyclic ring (the heterocyclic ring may be substituted by halogen, alkyl, haloalkyl, alkoxy, haloalkoxy, or alkylcarbonyl); Y is halogen, alkyl which may be substituted by $E^1$, alkenyl which may be substituted by $E^1$, alkynyl which may be substituted by $E^1$, hydroxy, cyanooxy, alkoxy which may be substituted by $E^1$, alkenyloxy which may be substituted by $E^1$, alkynyloxy which may be substituted by $E^1$, mercapto, cyanothio, alkylthio which may be substituted by $E^1$, alkenylthio which may be substituted by $E^1$, alkynylthio which may be substituted by $E^1$, alkylsulfinyl which may be substituted by $E^2$, alkylsulfonyl which may be substituted by $E^2$, cycloalkyl which may be substituted by J, cycloalkyloxy which may be substituted by J, cycloalkylthio which may be substituted by J, cyano, nitro, formyl, —$OR^4$, —$SR^5$, —$NR^6R^7$, —$CO_2R^8$, —$C(=O)NR^8R^9$, —$SO_2NR^8R^9$, —$CH=NR^{10}$, or heterocyclic ring (the heterocyclic ring may be substituted by halogen, alkyl, haloalkyl, alkoxy, haloalkoxy, or alkylcarbonyl); each of $R^1$ and $R^2$ which are independent of each other, is hydrogen, alkyl, haloalkyl, hydroxyalkyl, alkoxyalkyl, haloalkoxyalkyl, cyanoalkyl, alkoxycarbonylalkyl, alkenyl, haloalkenyl, alkoxyalkenyl, alkynyl, haloalkynyl, alkoxyalkynyl, cycloalkyl, halocycloalkyl, (alkyl)cycloalkyl, (haloalkyl)cycloalkyl, cyano, or —$CO_2R^8$, or $R^1$ and $R^2$ may together form a 3- to 6-membered saturated carbon ring; $R^3$ is hydrogen, alkyl which may be substituted by $E^1$, alkenyl which may be substituted by $E^1$, alkynyl which may be substituted by $E^1$, hydroxy, cyanooxy, alkoxy which may be substituted by $E^1$, cycloalkyl which may be substituted by J, cycloalkyloxy which may be substituted by J, cycloalkylthio which may be substituted by J, cyano, formyl, —$C(=W^3)R^{11}$, —$C(=W^3)OR^{12}$, —$C(=W^3)SR^{12}$, —$C(=W^3)NR^{12}R^{13}$, —$S(O)mR^{12}$, or —$S(O)nNR^{12}R^{13}$; $R^4$ is —$C(=W^3)R^{12}$, —$C(=W^3)OR^{12}$, —$C(=W^3)SR^{12}$, —$C(=W^3)NR^{12}R^{13}$, —$S(O)mR^{12}$, —$S(O)nNR^{12}R^{13}$, or heterocyclic ring (the heterocyclic ring may be substituted by halogen, alkyl, haloalkyl, alkoxy, haloalkoxy, or alkylcarbonyl); $R^5$ is —$C(=W^3)OR^{12}$, —$C(=W^3)SR^{12}$, —$C(=W^3)NR^{12}R^{13}$, or heterocyclic ring (the heterocyclic ring may be substituted by halogen, alkyl, haloalkyl, alkoxy, haloalkoxy, or alkylcarbonyl); $R^6$ is hydrogen, alkyl, haloalkyl, alkoxyalkyl, haloalkoxyalkyl, cyanoalkyl, (cycloalkyl)alkyl, cycloalkyl, cyano, —$C(=W^3)R^{12}$, —$C(=W^3)OR^{12}$, —$C(=W^3)SR^{12}$, —$C(=W^3)NR^{12}R^{13}$, —$S(O)mR^{12}$, —$S(O)nNR^{12}R^{13}$, or heterocyclic ring (the heterocyclic ring may be substituted by halogen, alkyl, haloalkyl, alkoxy, haloalkoxy, or an alkylcarbonyl); $R^7$ is hydrogen, alkyl, haloalkyl, alkoxyalkyl, or haloalkoxyalkyl; each of R⁸ and R⁹ which are independent of each other, is hydrogen, alkyl, haloalkyl, alkoxyalkyl, or haloalkoxyalkyl, and adjacent R⁸ and R⁹ may together form a ring; R¹⁰ is alkyl (the alkyl may be substituted by halogen, alkoxy, or haloalkoxy), alkoxy (the alkoxy may be substituted by halogen, alkoxy, or haloalkoxy), alkenyloxy (the alkenyloxy may be substituted by halogen, alkoxy, or haloalkoxy), alkynyloxy (the alkynyloxy may be substituted by halogen, alkoxy, or haloalkoxy), or alkoxycarbonyl (the alkoxycarbonyl may be substituted by halogen, alkoxy, or haloalkoxy); R¹¹ is hydrogen, alkyl which may be substituted by E³, phen (the phenyl may be substituted by halogen, alkyl, haloalkyl, alkoxy, haloalkoxy, or alkylcarbonyl), or heterocyclic ring (the heterocyclic ring may be substituted by halogen, alkyl, haloalkyl, alkoxy, haloalkoxy, or alkylcarbonyl); each of R¹² and R¹³ which are independent of each other, is alkyl which may be substituted by E³, alkoxy, haloalkoxy, cycloalkyl which may be substituted by J, or phenyl (the phenyl may be substituted by halogen, alkyl, haloalkyl, alkoxy, haloalkoxy, or alkylcarbonyl), or adjacent R¹² and R¹³ may together form a ring; each of W¹, W² and W³ which are independent of one another, is oxygen or sulfur; each of m and n which are independent of each other, is an integer of from 0 to 2; E¹ is halogen, hydroxy, alkoxy, haloalkoxy, mercapto, alkylthio, haloalkylthio, alkylsulfonyl, cycloalkyl, amino, monoalkylamino, dialkylamino, cyano, nitro, hydroxycarbonyl, alkoxycarbonyl, alkylcarbonyloxy, trialkylsilyl, or heterocyclic ring (the heterocyclic ring may be substituted by halogen, alkyl, haloalkyl, alkoxy, haloalkoxy, or alkylcarbonyl); E² is halogen, hydroxy, alkoxy, haloalkoxy, cycloalkyl, amino, monoalkylamino, dialkylamino, cyano, nitro, hydroxycarbonyl, alkoxycarbonyl, trialkylsilyl, or heterocyclic ring (the heterocyclic ring may be substituted by halogen, alkyl, haloalkyl, alkoxy, haloalkoxy, or alkylcarbonyl); E³ is halogen, alkoxy, alkylthio, amino, monoalkylamino, dialkylamino, cycloalkyl, cyano, alkoxycarbonyl, haloalkoxy, haloalkylthio, or phenyl (the phenyl may be substituted by halogen, alkyl, haloalkyl, alkoxy, haloalkoxy, or alkylcarbonyl); and J is halogen, alkyl, haloalkyl, alkoxy, or haloalkoxy. Further, the present invention provides a method for controlling various noxious fungi, or various diseases caused by various noxious fungi, which comprises applying an effective amount of such an acid amide derivative or a salt thereof, or a method for protecting crop plants or improving crop yields, which comprises applying an effective amount of such an acid amide derivative or a salt thereof. Further, the present invention provides an acid amide derivative of the formula (I-α) or a salt thereof, which has not been known specifically heretofore:

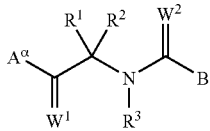

(I-α)

wherein A^α is phenyl which may be substituted by X^α, naphthyl substituted by X^α, thienyl substituted by X^α, benzodioxolanyl which may be substituted X^α, or benzodioxanyl which may be substituted X^α; B is heterocyclic ring (excluding pyridyl) which may be substituted by Y, fused heterocyclic ring which may be substituted by Y, or naphthyl which may be substituted by Y; X^α is fluorine, chlorine, iodine, alkyl, haloalkyl, alkoxyalkyl, dialkylaminoalkyl, alkynyl, trialkylsilylalkynyl, hydroxy, alkoxy, haloalkoxy, alkoxyalkoxy, cycloalkyl, nitro, phenyl, phenylalkynyl, pyridyloxy which may be substituted by haloalkyl, alkylcarbonyloxy, alkylsulfonyloxy, or heterocyclic ring (the heterocyclic ring may be substituted by halogen, alkyl, or alkylcarbonyl); Y is halogen, alkyl which may be substituted by E¹, alkenyl which may be substituted by E¹, alkynyl which may be substituted by E¹, hydroxy, cyanooxy, alkoxy which may be substituted by E¹, alkenyloxy which may be substituted by E¹, alkynyloxy which may be substituted by E¹, mercapto, cyanothio, alkylthio which may be substituted by E¹, alkenylthio which may be substituted by E¹, alkynylthio which may be substituted by E¹, alkylsulfinyl which may be substituted by E², alkylsulfonyl which may be substituted by E², cycloalkyl which may be substituted by J, cycloalkyloxy which may be substituted by J, cycloalkylthio which may be substituted by J, cyano, nitro, formyl, —OR⁴, —SR⁵, —NR⁶R⁷, —CO₂R⁸, —C(=O)NR⁸R⁹, —SO₂NR⁸R⁹, —CH=NR¹⁰, or heterocyclic ring (the heterocyclic ring may be substituted by halogen, alkyl, haloalkyl, alkoxy, haloalkoxy, or alkylcarbonyl); each of R¹ and R² which are independent of each other, is hydrogen, alkyl, haloalkyl, hydroxyalkyl, alkoxyalkyl, haloalkoxyalkyl, cyanoalkyl, alkoxycarbonylalkyl, alkenyl, haloalkenyl, alkoxyalkenyl, alkynyl, haloalkynyl, alkoxyalkynyl, cycloalkyl, halocycloalkyl, (alkyl)cycloalkyl, (haloalkyl)cycloalkyl, cyano, or —CO₂R⁸, or R¹ and R² may together form a 3- to 6-membered saturated carbon ring; R³ is hydrogen, alkyl which may be substituted by E¹, alkenyl which may be substituted by E¹, alkynyl which may be substituted by E¹, hydroxy, cyanooxy, alkoxy which may be substituted by E¹, cycloalkyl which may be substituted by J, cycloalkyloxy which may be substituted by J, cycloalkylthio which may be substituted by J, cyano, formyl, —C(=W³)R¹¹, —C(=W³)OR¹², —C(=W³)SR¹², —C(=W³)NR¹²R¹³, —S(O)mR¹², or S(O)nNR¹²R¹³; R⁴ is —C(=W³)R¹², —C(=W³)OR¹², —C(=W³)SR¹², —C(=W³)NR¹²R¹³, —S(O)mR¹², —S(O)nNR¹²R¹³, or heterocyclic ring (the heterocyclic ring may be substituted by halogen, alkyl, haloalkyl, alkoxy, haloalkoxy, or alkylcarbonyl); R⁵ is —C(=W³)R¹², —C(=W³)OR¹², —C(=W³)SR¹², —C(=W³)NR¹²R¹³, or heterocyclic ring (the heterocyclic ring may be substituted by halogen, alkyl, haloalkyl, alkoxy, haloalkoxy, or alkylcarbonyl); R⁶ is hydrogen, alkyl, haloalkyl, alkoxyalkyl, haloalkoxyalkyl, cyanoalkyl, (cycloalkyl)alkyl, cycloalkyl, cyano, —C(=W³)R¹², —C(=W³)OR¹², —C(=W³)SR¹², —C(=W³)NR¹²R¹³, —S(O)mR¹², —S(O)nNR¹²R¹³, or heterocyclic ring (the heterocyclic ring may be substituted by halogen, alkyl, haloalkyl, alkoxy, haloalkoxy, or alkylcarbonyl); R⁷ is hydrogen, alkyl, haloalkyl, alkoxyalkyl, or haloalkoxyalkyl; each of R⁸ and R⁹ which are independent of each other, is hydrogen, alkyl, haloalkyl, alkoxyalkyl, or haloalkoxyalkyl, and adjacent R⁸ and R⁹ may together form a ring; R¹⁰ is alkyl (the alkyl may be substituted by halogen, alkoxy, or haloalkoxy), alkoxy (the alkoxy may be substituted by halogen, alkoxy, or haloalkoxy), alkenyloxy (the alkenyloxy may be substituted by halogen, alkoxy, or haloalkoxy), alkynyloxy (the alkynyloxy may be substituted by halogen, alkoxy, or haloalkoxy), or alkoxycarbonyl (the alkoxycarbonyl may be substituted by halogen, alkoxy, or haloalkoxy); R¹¹ is hydrogen, alkyl which may be substituted by E³, phenyl (the phenyl may be substituted by halogen, alkyl, haloalkyl, alkoxy, haloalkoxy, or alkylcarbonyl), or heterocyclic ring (the heterocyclic ring may be substituted by halogen, alkyl, haloalkyl, alkoxy, haloalkoxy, or alkylcarbonyl); each of R¹² and R¹³ which are independent of each other, is alkyl which may be substituted by E³, alkoxy, haloalkoxy, cycloalkyl which may be substituted by J, or phenyl (the phenyl may be substituted by halogen, alkyl, haloalkyl, alkoxy, haloalkoxy, or alkylcarbonyl), and adjacent $R^{12}$ and $R^{13}$ may together form a ring; each of $W^1$, $W^2$ and $W^3$ which are independent of one another, is oxygen or sulfur; each of m and n which are independent of each other, is an integer of from 0 to 2; $E^1$ is halogen, hydroxy, alkoxy, haloalkoxy, mercapto, alkylthio, haloalkylthio, alkylsulfonyl, cycloalkyl, amino, monoalkylamino, dialkylamino, cyano, nitro, hydroxycarbonyl, alkoxycarbonyl, alkylcarbonyloxy, trialkylsilyl, or heterocyclic ring (the heterocyclic ring may be substituted by halogen, alkyl, haloalkyl, alkoxy, haloalkoxy, or alkylcarbonyl); $E^2$ is halogen, hydroxy, alkoxy, haloalkoxy, cycloalkyl, amino, monoalkylamino, dialkylamino, cyano, nitro, hydroxycarbonyl, alkoxycarbonyl, trialkylsilyl, or heterocyclic ring (the heterocyclic ring may be substituted by halogen, alkyl, haloalkyl, alkoxy, haloalkoxy, or alkylcarbonyl); $E^3$ is halogen, alkoxy, alkylthio, amino, monoalkylamino, dialkylamino, cycloalkyl, cyano, alkoxycarbonyl, haloalkoxy, haloalkylthio, or phenyl (the phenyl may be substituted by halogen, alkyl, haloalkyl, alkoxy, haloalkoxy, or alkylcarbonyl); and J is halogen, alkyl, haloalkyl, alkoxy, or haloalkoxy.

In the above formula (I), the number of substituents X contained in A may be one or more, and in the case of more than one, such substituents may be the same or different. The number of halogen, alkyl or alkoxy which is substituent(s) on indanyl or tetrahydronaphthyl contained in A, may be one or more, and in the case of more than one, such substituents may be the same or different. The number of substituents Y contained in B or X may be one or more, and in the case of more than one, such substituents may be the same or different. The number of substituents $E^1$, $E^2$ or $E^3$ contained in X, Y, $R^3$, $R^{11}$, $R^{12}$ or $R^{13}$, may be one or more, and in the case of more than one, such substituents may be the same or different. The number of substituents J contained in X, Y, $R^3$, $R^{12}$ or $R^{13}$, may be one or more, and in the case of more than one, such substituents may be the same or different. The number of halogen, alkyl, haloalkyl, alkoxy, haloalkoxy, or alkylcarbonyl, which is substituent(s) on phenyl or heterocyclic ring contained in X, Y, $R^4$, $R^5$, $R^6$, $R^{11}$, $R^{12}$, $R^{13}$, $E^1$, $E^2$ or $E^3$, may be one or more, and in the case of more than one, such substituents may be the same or different. The number of halogen, alkoxy or haloalkoxy, which is substituent(s) on alkyl, alkoxy, alkenyloxy, alkynyloxy or alkoxycarbonyl, contained in $R^{10}$, may be one or more, and in the case of more than one, such substituents may be the same or different.

The heterocyclic ring in A, B, X, Y, $R^4$, $R^5$, $R^6$, $R^{11}$, $E^1$ or $E^2$, is preferably a 3-, 5- or 6-membered heterocyclic ring containing from 1 to 4 atoms of at least one type selected from the group consisting of O, S and N, and it may, for example, be a 3-membered heterocyclic ring such as oxiranyl; a 5-membered heterocyclic ring such as furyl, tetrahydrofuryl, thienyl, pyrrolyl, pyrrolinyl, pyrrolidinyl, dioxolanyl, oxazolyl, isoxazolyl, thiazolyl, isothiazolyl, imidazolyl, imidazolinyl, imidazolidinyl, pyrazolyl, pyrazolinyl, pyrazolidinyl, triazolyl, oxadiazolyl, thiadiazolyl or tetrazolyl; a 6-membered heterocyclic ring such as pyranyl, pyridyl, piperidinyl, dioxanyl, oxazinyl, morpholinyl, thiazinyl, pyridazinyl, pyrimidinyl, pyrazinyl, piperazinyl or triazinyl.

The fused heterocyclic ring in A or B is preferably a 8- to 10-membered fused heterocyclic ring containing from 1 to 4 atoms of at least one type selected from the group consisting of O, S and N, and it may, for example, be benzofuranyl, isobenzofuranyl, dihydrobenzofuranyl, dihydroisobenzofuranyl, benzothienyl, isobenzothienyl, dihydrobenzothienyl, dihydroisobenzothienyl, tetrahydrobenzothienyl, indolyl, isoindolyl, benzoxazolyl, benzothiazolyl, indazolyl, benzimidazolyl, benzodioxolanyl, benzodioxanyl, chromenyl, chromanyl, isochromanyl, chromonyl, chromanonyl, quinolyl, isoquinolyl, cinnolinyl, phthalazinyl, quinazolinyl, quinoxalinyl, indolizinyl, quinolizinyl, imidazopyridyl, naphthyridinyl, pteridinyl, dihydrobenzoxazinyl, dihydrobenzoxazolinonyl, dihydrobenzoxazinonyl or benzothioxanyl.

The alkyl or alkyl moiety in A, X, Y, $R^1$ to $R^3$, $R^6$ to $R^{13}$, $E^1$ to $E^3$ or J, may be linear or branched, and as a specific example thereof, $C_{1-7}$ alkyl may be mentioned such as methyl, ethyl, propyl, isopropyl, butyl, tert-butyl, pentyl, hexyl or heptyl.

The cycloalkyl or cycloalkyl moiety in X, Y, $R^1$ to $R^3$, $R^6$, $R^{12}$, $R^{13}$ or $E^1$ to $E^3$, may be one having from 3 to 6 carbon atoms, such as cyclopropyl, cyclopentyl or cyclohexyl. Further, a specific example of the 3- to 6-membered saturated carbon ring which $R^1$ and $R^2$ may together form, may be cyclopropyl, cyclobutyl, cyclopentyl or cyclohexyl.

The alkenyl or alkenyl moiety in X, Y, $R^1$ to $R^3$ or $R^{10}$, may be a linear or branched one having from 2 to 7 carbon atoms, such as vinyl, 1-propenyl, allyl, isopropenyl, 1-butenyl, 1,3-butadienyl, 1-hexenyl or 1-heptenyl. Further, the alkynyl or alkynyl moiety in X, Y, $R^1$ to $R^3$ or $R^{10}$, may be a linear or branched one having from 2 to 7 carbon atoms, such as ethynyl, 2-butynyl, 2-pentynyl, 3-hexynyl or 4-dimethyl-2-pentynyl.

The halogen or the halogen as a substituent in A, X, Y, $R^1$ to $R^{13}$, $E^1$ to $E^3$ or J may be an atom of fluorine, chlorine, bromine or iodine. The number of halogen as substituent(s), may be one or more, and in the case of more than one, such halogens may be the same or different. Further, such halogens may be substituted at any positions.

The definition of substituent $A^\alpha$ or $X^\alpha$ in the above formula (I-α) follows the definition of substituent A or X in the above formula (I), respectively.

The salt of the acid amide derivative of the above formula (I) or (I-α) may be any salt so long as it is agriculturally acceptable. For example, it may be an alkali metal salt such as a sodium salt or a potassium salt; an alkaline earth metal salt such as a magnesium salt or a calcium salt; an inorganic acid salt such as a hydrochloride, a perchlorate, a sulfate or a nitrate; or an organic acid salt such as an acetate or a methane sulfonate.

The acid amide derivative of the above formula (I) or (I-α) has various isomers such as optical isomers or geometrical isomers, and the present invention includes both isomers and mixtures of such isomers. Further, the present invention also includes various isomers other than the above isomers within the common knowledge in the technical field concerned. Further, depending upon the types of isomers, they may have chemical structures different from the above formula (I) or (I-α), but they are within the scope of the present invention, since it is obvious to those skilled in the art that they are isomers.

The acid amide derivative of the above formula (I) or (I-α) or a salt thereof can be produced by the following reactions (A) to (K), (U) to (W), or by a usual process for producing a salt.

REACTION (A)

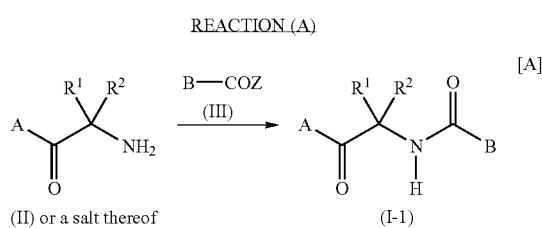

[A]

In the reaction (A), A, B, R$^1$, and R$^2$, are as defined above. Z is hydroxy, alkoxy or halogen, and the halogen may be an atom of fluorine, chlorine, bromine or iodine.

Reaction (A) may be carried out usually in the presence of a base and a solvent.

The base may be one or more suitably selected from e.g. an alkali metal such as sodium or potassium; an alkali metal alkoxide such as sodium methoxide, sodium ethoxide or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; a pyridine such as pyridine or 4-dimethylaminopyridine; and an organic lithium such as methyllithium, n-butyllithium or lithium diisopropyl amide. The base may be used in an amount of from 1 to 3 mols, preferably from 1 to 2 mols, per mol of the compound of the formula (II).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone, pyridine acetonitrile or propionitrile; and a ketone such as acetone or methyl ethyl ketone.

Reaction (A) may be carried out, if necessary, in the presence of a dehydration condensation agent. The dehydration condensation agent may, for example, be N,N'-dicyclohexylcarbodiimide, chlorosulfonyl isocyanate, N,N'-carbonyldiimidazole and trifluoroacetic anhydride.

The reaction temperature for reaction (A) is usually from 0 to 100° C., preferably from 0 to 50° C., and the reaction time is usually from 0.5 to 48 hours, preferably from 1 to 24 hours.

REACTION (B)

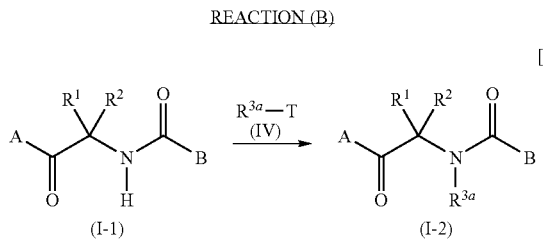

[B]

In reaction (B), A, B, R$^1$ and R$^2$ are as defined above, and R$^{3a}$ is alkyl which may be substituted by E$^1$, alkenyl which may be substituted by E$^1$, alkynyl which may be substituted by E$^1$, hydroxy, cyanooxy, alkoxy which may be substituted by E$^1$, cycloalkyl which may be substituted by J, cycloalkyloxy which may be substituted by J, cycloalkylthio which may be substituted by J, cyano, formyl, —C(=W$^3$)R$^{11}$, —C(=W$^3$)OR$^{12}$, —C(=W$^3$)SR$^{12}$, —C(=W$^3$)NR$^{12}$R$^{13}$, —S(O)mR$^{12}$ or S(O)nNR$^{12}$R$^{13}$ (E$^1$, J, R$^{11}$, R$^{12}$, R$^{13}$, W$^3$, m and n are as defined above) and T is halogen, and the halogen may be an atom of fluorine, chlorine, bromine or iodine.

Reaction (B) may be carried out usually in the presence of a base and a solvent.

The base may be one or more suitably selected from e.g. an alkali metal such as sodium or potassium; an alkali metal alkoxide such as sodium methoxide, sodium ethoxide or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base may be used in an amount of from 1 to 3 mols, preferably from 1 to 1.5 mols, per mol of the compound of the formula (I-1).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; and a ketone such as acetone or methyl ethyl ketone.

The reaction temperature for reaction (B) is usually from 0 to 100° C., preferably from 0 to 50° C., and the reaction time is usually from 1 to 300 hours, preferably from 1 to 150 hours.

REACTION (C)

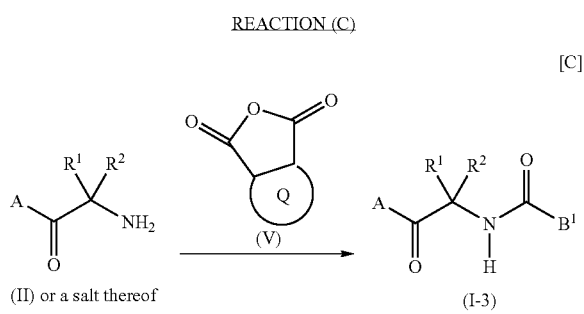

[C]

In reaction (C), A, R$^1$ and R$^2$ are as defined above, and B$^1$ is a heterocyclic ring substituted by —CO$_2$H, or a fused heterocyclic ring substituted by —CO$_2$H. The formula (V) is anhydrous dicarboxylic acid of Q (phenyl, a heterocycle or a fused heterocycle).

Reaction (C) may be carried out usually in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane;

an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; and an alcohol such as methanol, ethanol, propanol or tert-butanol.

Reaction (C) may be carried out, if necessary, in the presence of a base. The base may be one or more suitably selected from e.g. an alkali metal such as sodium or potassium; an alkali metal alkoxide such as sodium methoxide, sodium ethoxide or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base may be used in an amount of from 1 to 3 mols, preferably from 1 to 1.5 mols, per mol of the compound of the formula (II).

The reaction temperature for reaction (C) is usually from 0 to 150° C., preferably from 0 to 80° C. The reaction time is usually from 0.5 to 96 hours, preferably from 1 to 48 hours.

REACTION D

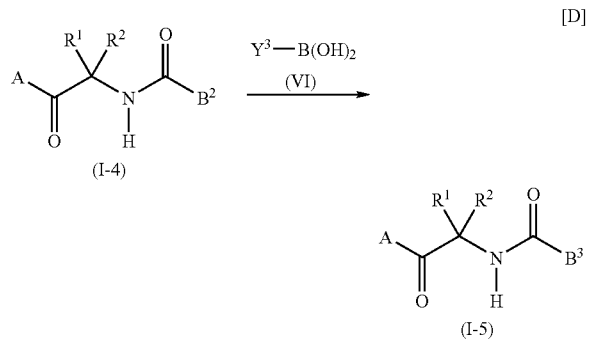

In reaction (D), A, $R^1$ and $R^2$ are as defined above. $B^2$ is a heterocyclic ring substituted by $Y^2$, or a fused heterocyclic ring substituted by $Y^2$, $B^3$ is a heterocyclic ring substituted by $Y^3$, or a fused heterocyclic ring substituted by $Y^3$, $Y^2$ is an atom of chlorine, bromine or iodine, and $Y^3$ is an unsaturated heterocyclic ring (the unsaturated heterocyclic ring may be substituted by halogen, alkyl, haloalkyl, alkoxy or haloalkoxy).

Reaction (D) may be carried out usually in the presence of a catalyst, a base, a solvent and an inert gas.

The catalyst may be one or more suitably selected from e.g. palladium complexes such as tetrakis (triphenylphosphine) palladium(0), bis (dibenzylideneacetone)palladium(0), and tris (dibenzylideneacetone)dipalladium(0).

The base may be one or more suitably selected from e.g. a carbonate such as sodium carbonate, potassium carbonate or calcium carbonate; a bicarbonate such as sodium bicarbonate or potassium bicarbonate; and a metal hydroxide such as sodium hydroxide or potassium hydroxide. The base may be used in an amount of from 1 to 20 mols, preferably from 1 to 10 mols, per mol of the compound of the formula (I-4).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; an alcohol such as methanol, ethanol, propanol or tert-butanol; and water.

The inert gas may, for example, be nitrogen gas or argon gas.

The reaction temperature for reaction (D) is usually from 0 to 150° C., preferably from 15 to 100° C. The reaction time is usually from 0.5 to 96 hours, preferably from 1 to 48 hours.

REACTION E

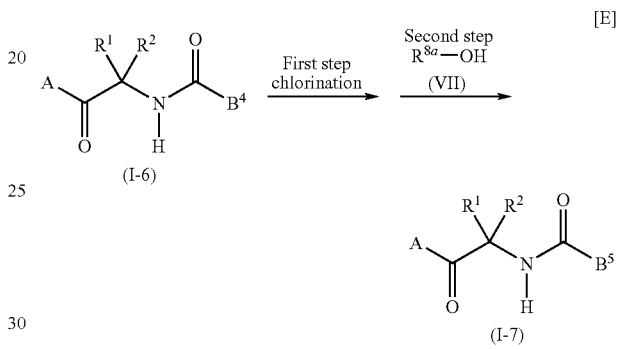

In reaction (E), A, $R^1$ and $R^2$ are as defined above, and $B^4$ is a heterocyclic ring substituted by $-CO_2H$, or a fused heterocyclic ring substituted by $-CO_2H$, $B^5$ is a heterocyclic ring substituted by $-CO_2R^{8a}$, or a fused heterocyclic ring substituted by $-CO_2R^{8a}$, and $R^{8a}$ is alkyl, haloalkyl, alkoxyalkyl or haloalkoxyalkyl.

The first step in reaction (E) may be carried out in the presence of a chlorination agent. The chlorination agent may be one or more suitably selected from e.g. thionyl chloride, oxalyl chloride and phosphorus pentachloride.

The first step in reaction (E) may be carried out, if necessary, in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; and an ester such as methyl acetate or ethyl acetate.

The reaction temperature for the first step in reaction (E) is usually from 0 to 200° C., preferably from 15 to 150° C. The reaction time is usually from 0.1 to 72 hours, preferably from 0.5 to 3 hours.

The second step in reaction (E) may be carried out, if necessary, in the presence of a base. The base may be one or more suitably selected from e.g. an alkali metal such as sodium or potassium; an alkali metal alkoxide such as sodium methoxide, sodium ethoxide or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base may be used in an amount of from 1 to 5 mols, preferably from 1 to 2 mols, per mol of the compound of the formula (I-6).

The second step in reaction (E) may be carried out, if necessary, in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; and a ketone such as acetone or methyl ethyl ketone. Further, in this reaction, the compound of the formula (VII) may serve also as a solvent if used excessively.

The reaction temperature for the second step in reaction (E) is usually from 0 to 100° C., preferably from 0 to 50° C. The reaction time is usually from 0.1 to 48 hours, preferably from 0.5 to 6 hours.

REACTION F

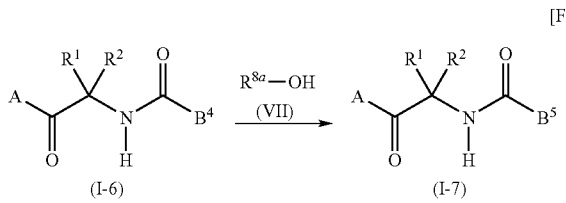

In reaction (F), A, B$^4$, B$^5$, R$^1$, R$^2$ and R$^{8a}$ are as defined above.

Reaction (F) may be carried out usually in the presence of a catalyst or a dehydration condensation agent.

The catalyst may be one or more suitably selected from e.g. a mineral acid such as hydrochloric acid or sulfuric acid; an organic acid such as paratoluene sulfonic acid; and a Lewis acid such as boron trifluoride etherate.

The dehydration condensation agent may be one or more suitably selected from e.g. N,N'-dicyclohexylcarbodiimide, chlorosulfonyl isocyanate, N,N'-carbonyldiimidazole and trifluoroacetic anhydride.

Reaction (F) may be carried out, if necessary, in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; and an alcohol such as methanol, ethanol, propanol or tert-butanol. Further, in this reaction, the compound of the formula (VII) may serve also as a solvent if used excessively.

The reaction temperature for reaction (F) is usually from 0 to 200° C., preferably from 0 to 100° C. The reaction time is usually from 0.1 to 96 hours, preferably from 0.5 to 24 hours.

REACTION G

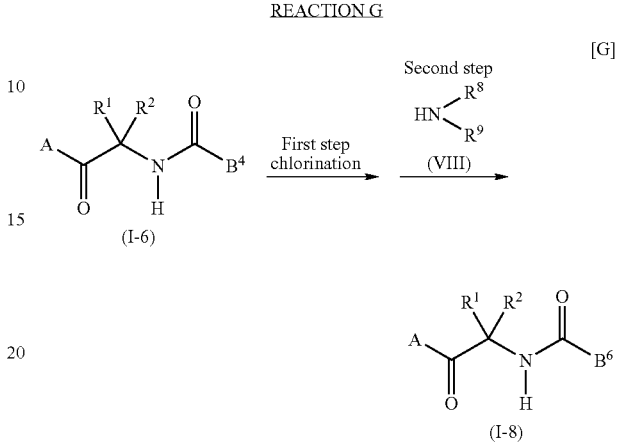

In reaction (G), A, B$^4$, R$^1$, R$^2$, R$^8$ and R$^9$ are as defined above, and B$^6$ is a heterocyclic ring substituted by —CONR$^8$R$^9$, or a fused heterocyclic ring substituted by —CONR$^8$R$^9$ (wherein R$^8$ and R$^9$ are as defined above).

The first step in reaction (G) may be carried out in accordance with the first step in the above-described reaction (E).

The second step in the reaction (G) may be carried out, if necessary, in the presence of a base. The base may be one or more suitably selected from e.g. an alkali metal such as sodium or potassium; an alkali metal alkoxide such as sodium methoxide, sodium ethoxide or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base may be used in an amount of from 1 to 10 mols, preferably from 1 to 2 mols, per mol of the compound of the formula (I-6).

The second step in reaction (G) may be carried out, if necessary, in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; and water.

The reaction temperature for the second step in reaction (G) is usually from 0 to 100° C., preferably from 0 to 50° C. The reaction time is usually from 0.1 to 48 hours, preferably from 0.5 to 6 hours.

REACTION H

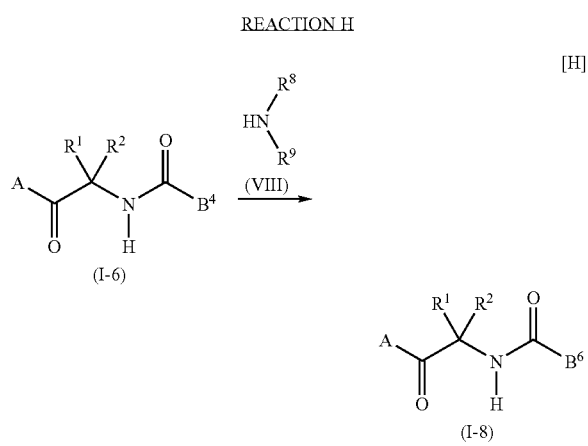

In reaction (H), A, B$^4$, B$^6$, R$^1$, R$^2$, R$^8$ and R$^9$ are as is defined above.

Reaction (H) may be carried out usually in the presence of a dehydration condensation agent and a solvent.

The dehydration condensation agent may be one or more suitably selected from e.g. N,N'-dicyclohexylcarbodiimide, chlorosulfonyl isocyanate, N,N'-carbonyldiimidazole and trifluoroacetic anhydride.

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; and a ketone such as acetone or methyl ethyl ketone.

The reaction temperature for the reaction (H) is usually from 0 to 200° C., preferably from 0 to 100° C. The reaction time is usually from 0.1 to 96 hours, preferably from 0.5 to 24 hours.

REACTION I

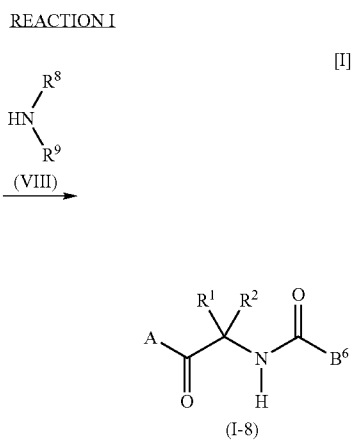

In reaction (I), A, B$^5$, B$^6$, RR$^1$, R$^2$, R$^8$ and R$^9$ are as defined above.

Reaction (I) may be carried out usually in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; an alcohol such as methanol, ethanol, propanol or tert-butanol; and water. Further, in this reaction, the compound of the formula (VIII) may serve also as a solvent if used excessively.

The reaction temperature for the reaction (I) is usually from 0 to 150° C., preferably from 0 to 80° C. The reaction time is usually from 0.1 to 48 hours, preferably from 0.5 to 24 hours.

REACTION J

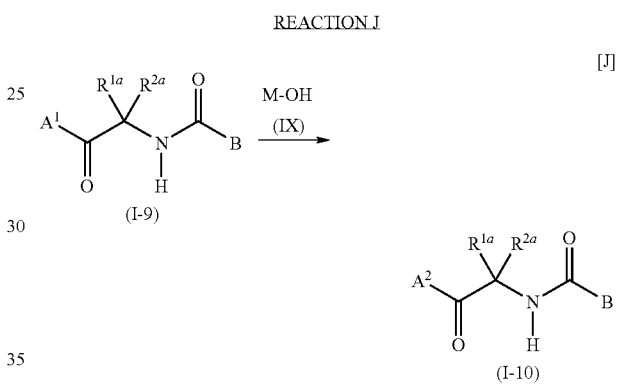

In reaction (J), B is as defined above, A$^1$ is phenyl substituted by —OR$^4$, benzyl substituted by —OR$^4$, naphthyl substituted by —OR$^4$, a heterocyclic ring substituted by —OR$^4$ or a fused heterocyclic ring substituted by —OR$^4$ (wherein R$^4$ is defined above), A$^2$ is phenyl substituted by —OH, benzyl substituted by —OH, naphthyl substituted by —OH, a heterocyclic ring substituted by —OH or a fused heterocyclic ring substituted by —OH, each of R$^{1a}$ and R$^{2a}$ is alkyl, haloalkyl, hydroxyalkyl, alkoxyalkyl, haloalkoxyalkyl, cyanoalkyl, alkoxycarbonylalkyl, alkenyl, haloalkenyl, alkoxyalkenyl, alkynyl, haloalkynyl, alkoxyalkynyl, cycloalkyl, halocycloalkyl, (alkyl)cycloalkyl, (haloalkyl)cycloalkyl or cyano, and R$^{1a}$ and R$^{2a}$ may together form a 3- to 6-membered saturated carbocycle, and M is sodium or potassium.

Reaction (J) may be usually carried out in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; an alcohol such as methanol, ethanol, propanol or tert-butanol; and water.

The reaction temperature for reaction (J) is usually from 0 to 100° C., preferably from 20 to 80° C. The reaction time is usually from 0.1 to 24 hours, preferably from 0.1 to 12 hours.

REACTION K

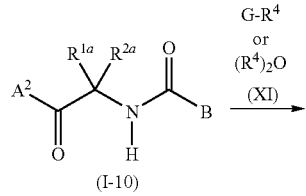

[K]

(I-10) → (I-9)

In reaction (K), $A^1$, $A^2$, B, $R^{1a}$, $R^{2a}$ and $R^4$ are as defined above, G is an atom of chlorine, bromine or iodine.

Reaction (K) may be usually carried out in the presence of a base and a solvent.

The base may be one or more suitably selected from e.g. an alkali metal alkoxide such as sodium methoxide, sodium ethoxide or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base may be used in an amount of from 1 to 2 mols, preferably from 1 to 1.5 mols, per mol of the compound of the formula (I-10).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; and a ketone such as acetone or methyl ethyl ketone.

The reaction temperature for reaction (K) is usually from −20 to 100° C., preferably from 0 to 50° C. The reaction time is usually from 0.1 to 24 hours, preferably from 0.1 to 12 hours.

The compound of the formula (II) to be used in the above reaction (A) or (C) can be produced by the following reactions (L) to (N).

REACTION (L)

[L]

(XII) → (II) or a salt thereof

In reaction (L), A, $R^1$ and $R^2$ are as defined above. In reaction (L), a salt of the compound (II) can be produced by post treatment of the reaction or in accordance with a usual reaction for forming a salt.

Reaction (L) may be carried out usually in the presence of an oxidizing agent and a solvent.

The oxidizing agent may, for example, be potassium ferricyanide. The oxidizing agent may be used in an amount of from 1 to 10 mols, preferably from 1 to 5 mols, per mol of the compound of the formula (XII).

The solvent may be any solvent so long as it is inert to the reaction. For example, it may be one or more suitably selected from e.g. an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone, pyridine, acetonitrile or propionitrile; and a ketone such as acetone or methyl ethyl ketone.

The reaction temperature for reaction (L) is usually from 20 to 150° C., preferably from 50 to 100° C. The reaction time is usually from 0.5 to 30 hours, preferably from 1 to 20 hours.

REACTION (M)

[M]

(XIII) → (II) or a salt thereof

In reaction (M), A, $R^1$ and $R^2$ are as defined above. In reaction (M), a salt of the compound (II) can be produced by post treatment of the reaction or in accordance with a usual reaction for forming a salt.

The cyclization reaction in reaction (M) may be carried out usually in the presence of a base and a solvent.

The base may be one or more suitably selected from e.g. an alkali metal such as sodium or potassium; an alkali metal alkoxide such as sodium methoxide, sodium ethoxide or potassium tert-butoxide; and a metal hydride such as sodium hydride or potassium hydride. The base may be used in an amount of from 1 to 3 mols, preferably from 1 to 1.5 mols per mol of the compound of the formula (XIII).

The solvent may be any solvent so long as it is inert to the reaction. For example, it may be one or more suitably selected from e.g. an aromatic hydrocarbon such as benzene, toluene, xylene or chlorobenzene; an ether such as dioxane, tetrahydrofuran, diethyl ether or dimethoxyethane; an alcohol such as methanol, ethanol, propanol or tert-butanol; and a nitrile such as acetonitrile, propionitrile or acrylonitrile.

The reaction temperature for the cyclization reaction in reaction (M) is usually from 0 to 150° C., preferably from 30 to 100° C. The reaction time is usually from 0.5 to 24 hours, preferably from 1 to 12 hours.

The hydrolytic reaction in reaction (M) may be carried out in accordance with a common hydrolytic reaction and may be carried out usually in the presence of an acid or base and a solvent.

The acid may, for example, be hydrogen chloride or sulfuric acid. The base may, for example, be a metal hydroxide such as sodium hydroxide or potassium hydroxide.

The solvent may be any solvent so long as it is inert to the reaction. For example, it may be one or more suitably selected e.g. an alcohol such as methanol, ethanol, propanol or tert-butanol; a nitrile such as acetonitrile, propionitrile or acrylonitrile; a ketone such as acetone or methyl ethyl ketone; and water.

The reaction temperature for the hydrolytic reaction in reaction (M) is usually from 0 to 100° C., preferably from 20 to 80° C. The reaction time is usually from 0.1 to 12 hours, preferably from 0.1 to 1 hour.

REACTION (N)

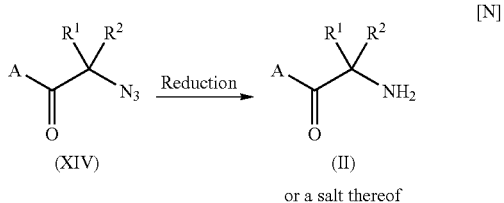

or a salt thereof

In reaction (N), A, $R^1$ and $R^2$ are as defined above. In reaction (N), a salt of the compound (II) can be produced by post treatment of the reaction or in accordance with a usual reaction for forming a salt.

The reduction reaction in reaction (N) may, for example, be catalytic reduction, reduction by a metal hydride (such as sodium boron hydride, or lithium aluminum hydride); reduction by e.g. triphenylphosphine, dimethyl sulfide or diphenyl sulfide; or reduction in a reaction system constituted by a metal such as iron or copper and a carboxylic acid such as formic acid or acetic acid. The catalytic reduction is usually carried out in a hydrogen atmosphere by using a catalyst, such as platinum, platinum oxide, platinum black, Raney Nickel, is palladium, palladium-carbon, rhodium or rhodium-alumina.

Reaction (N) may be carried out usually in the presence of a solvent. The solvent may be any solvent so long as it is a solvent inert to the reaction. For example, it may be one or more suitably selected from e.g. an aromatic hydrocarbon such as benzene, toluene or xylene; an aliphatic hydrocarbon such as hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone, pyridine, acetonitrile or propionitrile; a ketone such as acetone or methyl ethyl ketone; an alcohol such as methanol, ethanol, propanol or tert-butanol; and water.

The reaction temperature in reaction (N) is usually from 0 to 150° C., preferably from 0 to 80° C. The reaction time is usually from 0.5 to 96 hours, preferably from 1 to 48 hours.

The compound of the formula (XIII) to be used in the above reaction (M) can be produced by the following reaction (O).

REACTION (O)

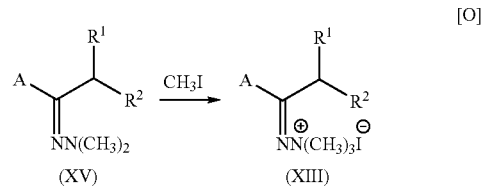

In reaction (O), A, $R^1$ and $R^2$ are as defined above.

Reaction (O) may be carried out, if necessary, in the presence of a solvent. The solvent may be any solvent so long as it is inert to the reaction, and for example, it may be one or more suitably selected from e.g. an aromatic hydrocarbon such as benzene, toluene, xylene or chlorobenzene; an aliphatic hydrocarbon such as carbon tetrachloride, chloroform, dichloromethane, dichloroethane, trichloroethane, hexane or cyclohexane; an ether such as dioxane, tetrahydrofuran, diethyl ether or dimethyoxyethane; an ester such as methyl acetate or ethyl acetate; an alcohol such as methanol, ethanol, propanol or tert-butanol; a polar aprotic solvent such as acetonitrile, propionitrile or acrylonitrile; and a ketone such as acetone or methyl ethyl ketone.

Methyl iodide in reaction (O) may be used in an amount of from 1 to 10 mols, preferably from 1 to 3 mols, per mol of the compound of the formula (XV). Further, methyl iodide may serve also as a solvent if used excessively.

The reaction temperature for reaction (O) is usually from 0 to 100° C., preferably from 10 to 50° C. The reaction time is usually from 0.5 to 48 hours, preferably from 1 to 24 hours.

The compound of the formula (XIV) to be used in the above reaction (N) can be produced by the following reaction (P).

REACTION (P)

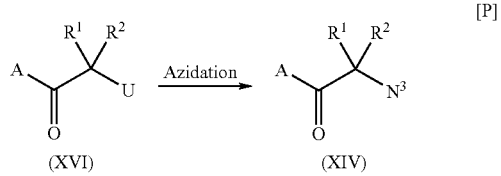

In reaction (P), A, $R^1$ and $R^2$ are as defined above, U is an atom of chlorine or bromine.

Reaction (P) may be carried out in the presence of an azidation agent. The azidation agent may be one or more suitably selected from e.g. sodium azide, potassium azide and trimethylsilyl azide.

Reaction (P) may be carried out usually in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone, pyridine, acetonitrile or propionitrile; a ketone such as acetone or methyl ethyl ketone; an alcohol such as methanol, ethanol, propanol or tert-butanol; and water.

The reaction temperature for reaction (P) is usually from 0 to 150° C., preferably from 20 to 90° C. The reaction time is usually from 0.1 to 96 hours, preferably from 0.5 to 12 hours.

The compound of the formula (XV) to be used in the above reaction (O) can be produced by the following reaction (Q).

REACTION (Q)

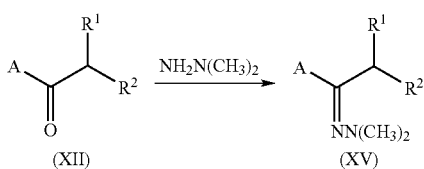

[Q]

In reaction (Q), A, $R^1$ and $R^2$ are as defined above.

Reaction (Q) can be carried out in accordance with a common hydrazone synthetic reaction and, if necessary, in the presence of a dehydrating agent and/or a catalyst.

As the dehydrating agent, molecular sieve may, for example, be mentioned. The dehydrating agent may be used usually from 1 to 30 times, preferably from 5 to 10 times relative to the weight of the compound of the formula (XII).

The catalyst may, for example, be titanium tetrachloride.

Dimethylhydrazine for reaction (Q) may be used usually in an amount of from 1 to 30 mols, preferably from 5 to 10 mols, per mol of the compound of the formula (XII).

The reaction temperature for reaction (Q) is usually from 20 to 150° C., preferably from 50 to 120° C. The reaction time is usually from 5 to 200 hours, preferably from 24 to 120 hours.

The compound of the formula (XVI) to be used in the above reaction (P) can be produced by the following reaction (R).

REACTION (R)

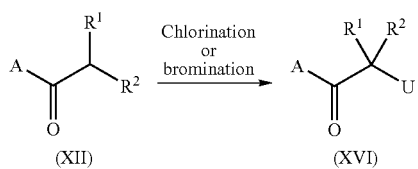

[R]

In reaction (R), A, $R^1$, $R^2$ and U are as defined above.

Reaction (R) may be carried out in the presence of a chlorination agent or a bromination agent. The chlorination agent may be one or more suitably selected from e.g. chlorine and N-chlorosuccinimide. The bromination agent may be one or more suitably selected from e.g. bromine, N-bromosuccinimide and phenyltrimethyl ammonium tribromide.

Reaction (R) may be carried out usually in the presence of a solvent. The solvent may be any solvent so long as it is a solvent inert to the reaction. For example, it may be one or more suitably selected from e.g. an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; an organic acid such as acetic acid or propionic acid; and water.

Reaction (R) may be carried out, if necessary, in the presence of a base or an acid.

The base may, for example, be lithium diisopropylamide. The base is used in an amount of from 1 to 2 mols, preferably from 1 to 1.2 mols, per mol of the compound of the formula (XII).

When the reaction is carried out in the presence of a base, the solvent may usually be one or more suitably selected from ethers such as tetrahydrofuran and diethyl ether.

The acid may be one or more suitably selected from e.g. an organic acid such as acetic acid or propionic acid, and aluminum chloride. The acid is usually used in a catalytic amount. Further, an organic acid as a solvent may serve as both a solvent and an acid if used excessively.

The reaction temperature for reaction (R) is usually from −100 to 150° C., preferably from −78 to 110° C. The reaction time is usually from 0.1 to 48 hours, preferably from 0.5 to 24 hours. However, if it is carried out in the presence of a base, the reaction temperature is usually from −100 to 0° C., preferably from −78 to −20° C., and the reaction time is usually from 0.1 to 12 hours, preferably from 0.5 to 6 hours. If it is carried out in the presence of an acid, the reaction temperature is usually from 0 to 150° C., preferably from 20 to 110° C., and the reaction time is usually from 0.1 to 48 hours, preferably from 1 to 24 hours.

The compound of the formula (XII) to be used in the above reaction (Q) is a known compound, or can be produced by the following reactions (S) to (T) or by methods in accordance therewith.

REACTION (S)

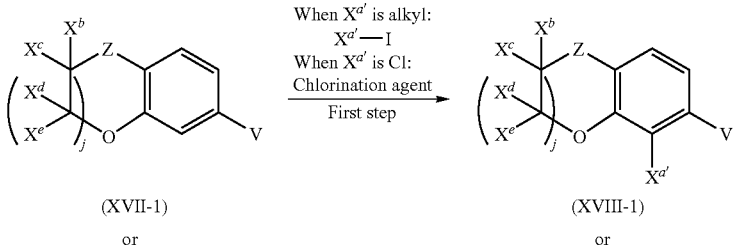

[S]

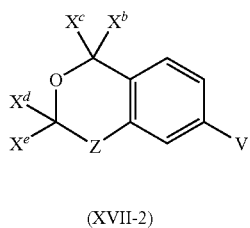

(XVII-2)

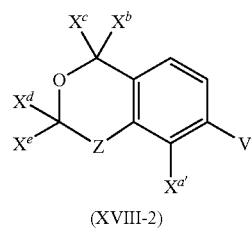

(XVIII-2)

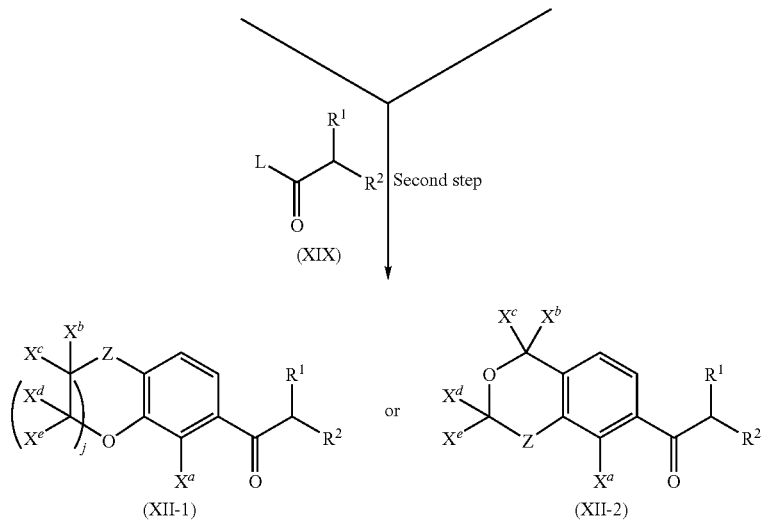

In reaction (S), $R^1$ and $R^2$ are as defined above, and Z is an oxygen atom or $-C(G^1)G^2-$, $X^a$ is an hydrogen atom, chlorine atom or alkyl, $X^{a'}$ is a chlorine atom or alkyl, each of $X^b$, $X^c$, $X^d$, $X^e$, $G^1$ and $G^2$ is an atom of hydrogen, fluorine or chlorine, V is an atom of bromine or iodine, and j is 0 or 1.

The first step in reaction (S) may be carried out in the presence of a base and a solvent.

The base may be suitably selected from an organic lithium compound such as lithium diisopropylamide. The base may be used in an amount of from 1 to 2 mols, preferably from 1 to 1.5 mols, per mol of the compound of the formula (XVII-1) or (XVII-2).

The solvent may be any solvent so long as it is a solvent inert to the reaction. For example, it may be one or more suitably selected from e.g. an ether such as dioxane, tetrahydrofuran and diethyl ether.

The chlorination agent to be used for the first step in reaction (S) may, for example, be N-chlorosuccinimide.

The formula: $X^{a'}$—I to be used for the first step in reaction (S) may be used in an amount of from 1 to 10 mols, preferably from 1 to 5 mols, per mol of the compound of the formula (XVII-1) or (XVII-2). Further, the chlorination agent to be used for the first step in reaction (S) is used in an amount of from 1 to 5 mols, preferably from 1 to 3 mols, per mol of the compound of the formula (XVII-1) or (XVII-2).

The first step in reaction (S) may be carried out, if necessary, in the presence of an inert gas. The inert gas may be suitably selected from e.g. nitrogen gas or argon gas.

The reaction temperature for the first step in reaction (S) is usually from −100 to 50° C., preferably from −70 to 25° C. The reaction time is usually from 1 to 48 hours, preferably from 1 to 20 hours.

The second step in reaction (S) may be carried out, usually in the presence of a base and a solvent.

The base may be one or more suitably selected from e.g. organic lithium compounds such as methyllithium and n-butyllithium; and Grignard compounds such as isopropyl magnesium chloride. The base may be used in an amount of from 1 to 2 mols, preferably from 1 to 1.5 mols, per mol of the compound of the formula (XVII-1), (XVII-2), (XVIII-1) or (XVIII-2).

The solvent may be any solvent so long as it is a solvent inert to the reaction. For example, it may be one or more suitably selected from e.g. an ether such as dioxane, tetrahydrofuran and diethyl ether.

The compound of the formula (XIX) to be used for the second step in reaction (S) is used in an amount of from 1 to 3 mols, preferably from 1 to 1.5 mols, per mol of the compound of the formula (XVII-1), (XVII-2), (XVIII-1) or (XVIII-2).

The second step in reaction (S) may be carried out, if necessary, in the presence of an inert gas. The inert gas may be suitably selected from e.g. nitrogen gas and argon gas.

The reaction temperature for the second step in reaction (S) is usually from −100 to 50° C., preferably from −70 to 25° C. The reaction time is usually from 1 to 48 hours, preferably from 1 to 20 hours.

REACTION (T)

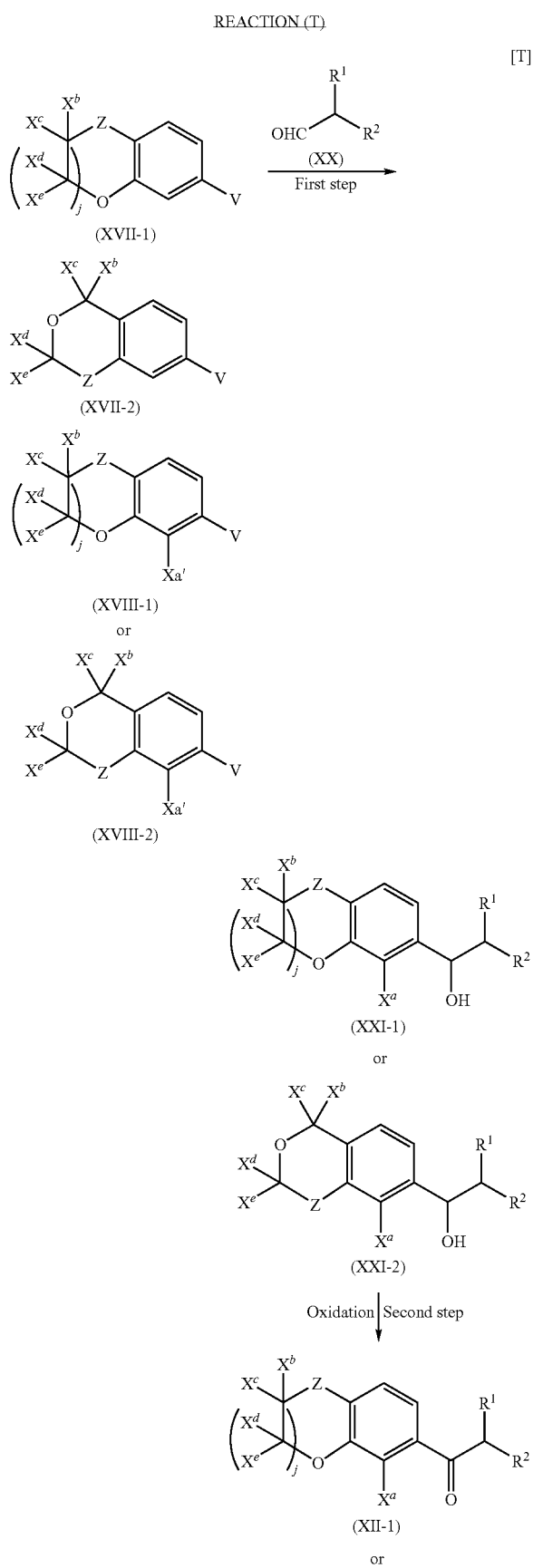

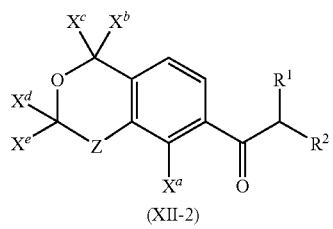

In reaction (T), $R^1$, $R^2$, Z, $X^a$, $X^{a'}$, $X^b$, $X^c$, $X^d$, $X^e$, V and j are as defined above.

The first step in reaction (T) may be carried out usually in the presence of a base and a solvent.

The base may be one or more suitably selected from e.g. organic lithium compounds such as methyllithium and n-butyllithium; and Grignard compounds such as isopropyl magnesium chloride.

The base is used in an amount of from 1 to 2 mols, preferably from 1 to 1.5 mols, per mol of the compound of the formula (XVII-1), (XVII-2), (XVIII-1) or (XVIII-2).

The solvent may be any solvent so long as it is a solvent inert to the reaction. For example, it may be one or more suitably selected from e.g. an ether such as dioxane, tetrahydrofuran and diethyl ether.

The compound of the formula (XX) to be used for the first step in reaction (T) is used in an amount of from 1 to 3 mols, preferably from 1 to 1.5 mols, per mol of the compound of the formula (XVII-1), (XVII-2), (XVIII-1) or (XVIII-2).

The first step in reaction (T) may be carried out, if necessary, in the presence of an inert gas. The inert gas may be suitably selected from e.g. nitrogen gas and argon gas.

The reaction temperature for the first step in reaction (T) is usually from −100 to 50° C., preferably from −70 to 25° C. The reaction time is usually from 1 to 48 hours, preferably from 1 to 20 hours.

The second step for reaction (T) may be carried out usually in the presence of an oxidizing agent and a solvent.

The oxidizing agent may be one or more suitably selected from e.g. pyridinium chlorochromate and manganese dioxide. The oxidizing agent is used in an amount of from 1 to 10 mols, preferably from 1 to 3 mols, per mol of the compound of the formula (XXI-1) or (XXI-2).

The solvent may be any solvent so long as it is a solvent inert to the reaction. For example, it may be one or more suitably selected from e.g. an aromatic hydrocarbon such as benzene, toluene, xylene or chlorobenzene; and an aliphatic hydrocarbon such as carbon tetrachloride, chloroform, dichloromethane, dichloroethane, trichloroethane, hexane or cyclohexane.

The reaction temperature for the second step in reaction (T) is usually from 0 to 150° C., preferably from 20 to 100° C. The reaction time is usually from 0.5 to 24 hours, preferably from 1 to 12 hours.

REACTION (U)

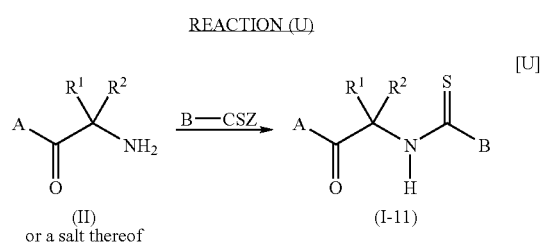

In reaction (U), A, B, $R^1$, $R^2$ and Z, are as defined above.
Reaction (U) may be carried out in accordance with the above reaction (A).

REACTION (V)

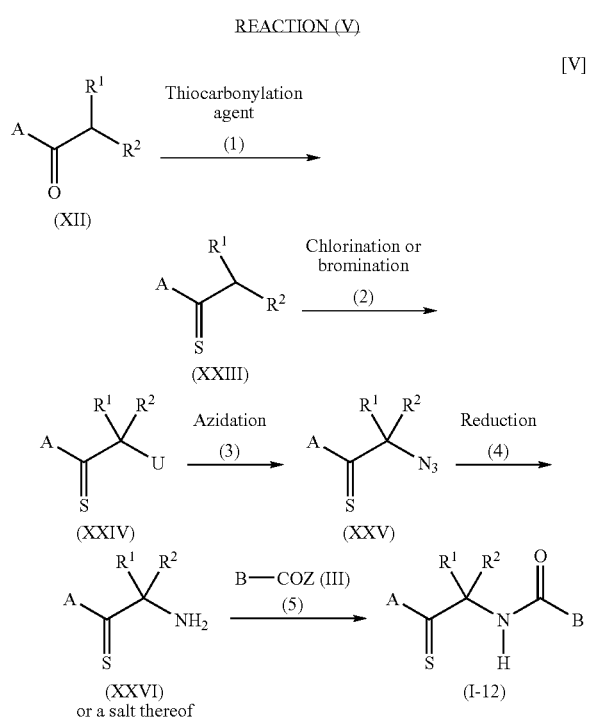

In reaction (V), A, B, $R^1$, $R^2$, U and Z are as defined above. Further, the thiocarbonylation agent, may, for example, be a Lawesson reagent or diphosphorus pentasulfide. Reaction (V) comprises five stage reactions (1) to (5) as shown in the above flow process, and the reaction conditions of the respective reactions will be described below.

The reaction (1) may usually be carried out in the presence of a solvent. The solvent may be any solvent inert to the reaction, and it may be one or more suitably selected from aromatic hydrocarbons such as benzene, toluene and xylene; aliphatic hydrocarbons such as pentane, hexane, heptane, petroleum ether, ligroin and petroleum benzin; ethers such as diethyl ether, dipropyl ether, dibutyl ether, tetrahydrofuran, and dioxane; and carbon disulfide.

The reaction (1) may usually be carried out at from −20° C. to 150° C., preferably from 0 to 110° C., and the reaction time is usually from 0.1 to 48 hours.

In the reaction (1), the thiocarbonylation agent may be used in an amount of from 0.4 to 2 mols, per mol of the compound of the formula (XII).

The reaction (2) can be carried out in accordance with the above reaction (R).

The reaction (3) can be carried out in accordance with the above reaction (P).

The reaction (4) can be carried out in accordance with the above reaction (N).

The reaction (5) can be carried out in accordance with the above reaction (A).

REACTION (W)

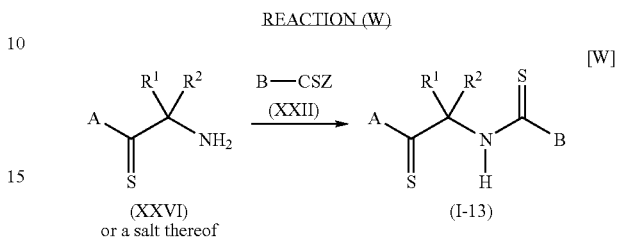

In reaction (W), A, B, $R^1$, $R^2$ and Z are as defined above.
Reaction (W) can be carried out in accordance with the above reaction (A).

Further, the acid amide derivative of the formula (I) or a salt thereof may be produced with reference to the method disclosed in WO2001/60783 or WO2003/27059, as the case requires.

A fungicidal composition containing an acid amide derivative of the formula (I) or a salt thereof as an active ingredient (hereinafter referred to simply as the composition of the present invention) is capable of controlling noxious fungi at a low dose and thus useful, for example, as an agricultural or horticultural fungicidal composition.

BEST MODE FOR CARRYING OUT THE INVENTION

Now, preferred embodiments of the composition of the present invention will be described.

The composition of the present invention is useful as a fungicidal composition capable of controlling noxious fungi at a low dose, particularly useful as an agricultural or horticultural fungicidal composition. When used as an agricultural or horticultural fungicidal composition, the composition of the present invention is capable of controlling noxious fungi such as Oomycetes, Ascomycetes, Basidiomycetes, Deuteromycetes and particularly effective for controlling noxious fungi belonging to e.g. Ascomycetes or Deuteromycetes.

The following may be mentioned as specific examples of the above noxious fungi.

Oomycetes may, for example, be genus *Phytophthora*, such as potato or tomato late blight pathogen (*Phytophthora infestans*), or tomato haiiro-eki-byo pathogen (*Phytophthora capsici*); genus *Pseudoperonospora*, such as cucumber downy mildew pathogen (*Pseudoperonospora cubensis*); genus *Plasmopara*, such as grape downy mildew pathogen (*Plasmopara viticola*); and genus *Pythium*, such as rice seedling blight pathogen (*Pythium graminicola*), or wheat browning root rot pathogen (*Pythium iwayamai*).

Ascomycetes may, for example, be genus *Erysiphe*, such as wheat powdery mildew pathogen (*Erysiphe graminis*); genus *Sphaerotheca*, such as cucumber powdery mildew pathogen (*Sphaerotheca fuliginea*), or strawberry powdery mildew pathogen (*Sphaerotheca humuli*); genus *Uncinula*, such as grape powdery mildew pathogen (*Uncinula necator*); genus *Podosphaera*, such as apple powdery mildew pathogen (*Podosphaera leucotricha*); genus *Mycosphaerella*, such as garden pea *Mycosphaerella* blight pathogen (*Mycosphaerella*

*pinodes*), apple fruit spot pathogen (*Mycosphaerella pomi*), banana black sigatoka pathogen (*Mycosphaerella musicola*), persimmons circular leaf spot pathogen (*Mycosphaerella nawae*), or strawberry leaf spot pathogen (*Mycosphaerella fragariae*); genus *Venturia*, such as apple scab pathogen (*Venturia inaequalis*), or pear scab pathogen (*Venturia nashicola*); genus *Pyrenophora*, such as barley net blotch pathogen (*Pyrenophora teres*), or barley stripe pathogen (*Pyrenophora graminea*); genus *Sclerotinia*, such as various *Sclerotinia* disease pathogen (*Sclerotinia Sclerotiorum*) such as kidney bean stem rot pathogen, cucumber *Sclerotinia* rot pathogen, cabbage *Sclerotinia* rot pathogen, Chinese cabbage *Sclerotinia* rot pathogen, red pepper *Sclerotinia* rot pathogen, sweet pepper *Sclerotinia* rot pathogen, or onion watery soft rot pathogen, wheat *Sclerotinia* snow blight pathogen (*Sclerotinia borealis*), tomato syoryu-kinkaku pathogen (*Sclerotinia minor*), or alfalfa *Sclerotinia* rot and crown rot pathogen (*Sclerotinia trifoliorum*); genus *Botryolinia*, such as peanut small *Sclerotinia* rot pathogen (*Botryolinia arachidis*); genus *Cochliobolus*, such as rice brown spot pathogen (*Cochliobolus miyabeanus*); genus *Didymella*, such as cucumber gummy stem blight pathogen (*Didymella bryoniae*); genus *Gibberella*, such as wheat *Fusarium* blight pathogen (*Gibberella zeae*); genus *Elsinoe*, such as grape anthracnose pathogen (*Elsinoe ampelina*), or citrus scab pathogen (*Elsinoe fawcettii*); genus *Diaporthe*, such as citrus melanose pathogen (*Diaporthe citri*), or grape swelling arm pathogen (*Diaporthe* sp.); genus *Monilinia*, such as apple blossom blight pathogen (*Monilinia mali*), or peach brown rot pathogen (*Monilinia fructicola*); and genus *Glomerella*, such as grape ripe rot pathogen (*Glomerella cingulata*).

Basidiomycetes may, for example, be genus *Rhizoctonia*, such as rice sheath blight pathogen (*Rhizoctonia solani*); genus *Ustilago*, such as wheat loose smut pathogen (*Ustilago nuda*); genus *Puccinia*, such as oat crown rust pathogen (*Puccinia coronata*), wheat brown rust pathogen (*Puccinia recondita*), or wheat stripe rust pathogen (*Puccinia striiformis*); and genus *Typhula*, such as wheat or barley *Typhula* snow blight pathogen (*Typhula incarnata, Typhula ishikariensisis*).

Deuteromycetes may, for example, be genus *Septoria*, such as wheat glume blotch pathogen (*Septoria nodorum*), wheat speckled leaf blotch (*Septoria tritici*); genus *Botrytis*, such as various gray mold pathogen (*Botrytis cinerea*) such as grape gray mold pathogen, citrus gray mold pathogen, cucumber gray mold pathogen, tomato gray mold pathogen, strawberry gray mold pathogen, eggplant gray mold pathogen, kidney bean gray mold pathogen, adzuki bean gray mold pathogen, garden pea gray mold pathogen, peanut gray mold pathogen, red pepper gray mold pathogen, sweet pepper gray mold pathogen, lettuce gray mold pathogen, onion gray mold pathogen, statice gray mold pathogen, carnation gray mold pathogen, rose *Botrytis* blight pathogen, garden pansy gray mold pathogen, or sunflower gray mold pathogen, onion gray mold neck rot pathogen (*Botrytis allii*), or onion *Botrytis* hagare-syo (*Botrytis squamosa, Botrytis byssoidea, Botrytis tulipae*); genus *Pyricularia*, such as rice blast pathogen (*Pyricularia oryzae*); genus *Cercospora*, such as sugar beet *Cercospora* leaf spot pathogen (*Cercospora beticola*), or persimmons *Cercospora* leaf spot pathogen (*Cercospora kakivola*); genus *Colletotrichum*, such as cucumber anthracnose pathogen (*Colletotrichum orbiculare*); genus *Alternaria*, such as apple *Alternaria* leaf spot pathogen (*Alternaria alternata* apple pathotype), pear black spot pathogen (*Alternaria alternata* Japanese pear pathotype), potato or tomato early blight pathogen (*Alternaria solani*), cabbage or Chinese cabbage *Alternaria* leaf spot pathogen (*Alternaria brassicae*), cabbage *Alternaria* sooty spot pathogen (*Alternaria brassicola*), onion or Welsh onion *Alternaria* leaf spot pathogen (*Alternaria porri*); genus *Pseudocercosporella*, such as wheat eye spot pathogen (*Pseudocercosporella herpotrichoides*); genus *Pseudocercospora*, such as grape leaf spot pathogen (*Pseudocercospora vitis*); genus *Rhynchosporium*, such as barley scold pathogen (*Rhynchosporium secalis*); genus *Cladosporium*, such as peach scab pathogen (*Cladosporium carpophilum*); genus *Phomopsis*, such as peach *Phomopsis* rot pathogen (*Phomopsis* sp.); genus *Gloeosporium*, such as persimmons anthracnose pathogen (*Gloeosporium kaki*); genus *Fulvia*, such as tomato leaf mold pathogen (*Fulvia fulva*); and genus *Corynespora*, such as cucumber *Corynespora* leaf spot pathogen (*Corynespora cassiicola*).

The composition of the present invention is capable of controlling the above various noxious fungi and thus capable of preventively or curatively controlling various diseases. Particularly, the composition of the present invention is effective for controlling various diseases which are problematic in the agricultural and horticultural field, such as blast, brown spot, sheath blight or damping-off of rice (*Oryza sativa*, etc.); powdery mildew, scab, brown rust, stripe rust, net blotch, stripe, snow mold, snow blight, loose smut, eye spot, scald, leaf spot or glume blotch of cereals (*Hordeum vulgare, Tricum aestivum*, etc.); melanose or scab of citrus (*Citrus* spp., etc.); blossom blight, powdery mildew, melanose, *Alternaria* leaf spot or scab of apple (*Malus pumila*); scab or black spot of pear (*Pyrus serotina, Pyrus ussuriensis, Pyrus communis*); brown rot, scab or *Phomopsis* rot of peach (*Prunus persica*, etc.); anthracnose, ripe rot, leaf spot, swelling arm, powdery mildew or downy mildew of grape (*Vitis vinifera* spp., etc.); anthracnose, circular leaf spot or *Cercospora* leaf spot of Japanese persimmon (*Diospyros kaki*, etc.); anthracnose, powdery mildew, gummy stem blight, corynespora leaf spot or downy mildew of cucurbit (*Cucumis melo*, etc.); early blight, haiiro-eki-byo, leaf mold or late blight of tomato (*Lycopersicon esculentum*); black sigatoka of banana (*Musa sapientum*, etc.); *Cercospora* leaf spot of sugar beet (*Beta vulgaris* var. *saccharifera*, etc.); *Mycosphaerella* blight of garden pea (*Pisum sativum*); various *Alternaria* disease pathogens of cruciferous vegetables (*Brassica* sp., *Raphanus* sp., etc); late blight or early blight of potato (*Solanum tuberosum*); powdery mildew or leaf spot of strawberry (*Fragaria*, etc.); and gray mold or disease caused by *Sclerotinia* of various crops such as beans, vegetables, fruits or flowers. Among them, it is particularly effective against various gray mold or disease caused by *Sclerotinia* of cucumber (*Cucumis sativus*), kidney bean (*Phaseolus vulgaris*), adzuki bean (*Vigna angularis*), soybean (*Glycine max*), garden pea, peanut (*Arachis hypogaea*), tomato, strawberry, eggplant (*Solanum melongena*), red pepper (*Capsicum annuum*), sweet pepper (*Capsicum annuum*), lettuce (*Lactuca sativa*), onion (*Allium cepa*), grape, citrus, statice (*Limonium* spp.), carnation (*Dianthus* spp.), rose (*Rosa* spp.), garden pansy (*Viola*, etc.) or sunflower (*Helianthus annuus*).

Further, the composition of the present invention is effective also for preventive or curative control of soil diseases caused by plant pathogens such as *Fusarium, Pythium, Rhizoctonia, Verticillium* and *Plasmodiophora*.

Still further, the composition of the present invention is effective also to control various pathogens resistant to fungicides such as benzimidazoles, strobilurins, dicarboximides, phenylamides and ergosterol biosynthesis inhibitors.

Furthermore, the composition of the present invention has an excellent penetrative migration property, and when a pesticide containing the composition of the present invention is applied to soil, it is possible to control noxious fungi on stems and leaves at the same time as controlling noxious fungi in soil.

The composition of the present invention, is usually formulated by mixing the acid amide derivative represented by the formula (I) or a salt thereof with various agricultural adjuvants and used in the form of a formulation such as a dust, granules, water-dispersible granules, a wettable powder, a water-based suspension concentrate, an oil-based suspension concentrate, water soluble granules, an emulsifiable concentrate, a soluble concentrate, a paste, an aerosol or an ultra low-volume formulation. However, so long as it is suitable for the purpose of the present invention, it may be formulated into any type of formulation which is commonly used in this field. Such agricultural adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethylsulfoxide, N,N-dimethylformamide, dimethylacetamide, N-methyl-2-pyrrolidone, and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyethylene glycol, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Each of the components as such adjuvants may be one or more suitable selected for use, so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed.

The weight ratio of the acid amide derivative represented by the formula (I) or a salt thereof to the various agricultural adjuvants is usually from 0.001:99.999 to 95:5, preferably from 0.005:99.995 to 90:10.

In the actual application of such a formulation, it may be used as it is, or may be diluted to a predetermined concentration with a diluent such as water, and various spreaders e.g. surfactants, vegetable oils or mineral oils may be added thereto, as the case requires.

The application of the composition of the present invention can not generally be defined, as it varies depending upon the weather conditions, the type of the formulation, the crop plants to be treated, the application season, the application site, the types or germination states of noxious fungi, and the types or degree of outbreak of the diseases. However, it is usually applied in a concentration of the active ingredient being from 0.1 to 10,000 ppm, preferably from 1 to 2,000 ppm in the case of foliage treatment, and its dose may be such that the acid amide derivative of the formula (I) or a salt thereof is usually from 0.1 to 50,000 g, preferably from 1 to 30,000 g, per hectare. In the case of soil treatment, it is applied usually in such a dose that the acid amide derivative of the formula (I) or a salt thereof is from 10 to 100,000 g, preferably from 200 to 20,000 g, per hectare.

The formulation containing the composition of the present invention or a diluted product thereof may be applied by an application method which is commonly used, such as spreading (spreading, spraying, misting, atomizing, grain diffusing or application on water surface), soil application (such as mixing or irrigation) or surface application (such as coating, dust coating or covering). Further, it may be applied also by so-called ultra low volume. In this method, the formulation may contain 100% of the active ingredient.

The composition of the present invention may be mixed with or may be used in combination with other agricultural chemicals, fertilizers or phytotoxicity-reducing agents, whereby synergistic effects or activities may sometimes be obtained. Such other agricultural chemicals may, for example, be a herbicide, an insecticide, a miticide, a nematicide, a soil pesticide, a fungicide, an antivirus agent, an attractant, an antibiotic, a plant hormone and a plant growth regulating agent. Especially, with a mixed fungicidal composition having the acid amide derivative of the formula (I) or a salt thereof mixed with or used in combination with one or more of other fungicidally active ingredient compounds, the application range, the application time, the fungicidal activities, etc. may be improved to preferred directions. Here, the acid amide derivative of the formula (I) or a salt thereof, and the active ingredient compound of another fungicide may separately be formulated so that they may be mixed for use at the time of application, or they may be formulated together for use. The present invention includes such a mixed fungicidal composition.

The mixing ratio of the acid amide derivative of the formula (I) or a salt thereof to another fungicidally active ingredient compound can not generally be defined, since it varies depending upon the weather conditions, the types of formulations, the crops to be treated, the application time, the application site, the types or germination state of noxious fungi, the types or state of the diseases, etc., but it is usually within a range of from 1:300 to 300:1, preferably from 1:100 to 100:1, by weight. Further, the dose for the application may be such that the total amount of the active compounds is from 0.1 to 70,000 g, preferably from 1 to 30,000 g, per hectare. The present invention includes a method for controlling noxious fungi by an application of such a mixed fungicidal composition.

The active ingredient compound (common name; including some which are under application or test code of the Japan plant protection association) of the fungicide in such another agricultural chemical, may, for example, be:
an anilinopyrimidine compound such as Mepanipyrim, Pyrimethanil or Cyprodinil;
a pyridinamine compound such as Fluazinam;
an azole compound such as Triadimefon, Bitertanol, Triflumizole, Etaconazole, Propiconazole, Penconazole, Flusilazole, Myclobutanil, Cyproconazole, Tebuconazole, Hexaconazole, Furconazole-cis, Prochloraz, Metconazole, Epoxiconazole, Tetraconazole, Oxpoconazole fumarate, Sipconazole, Prothioconazole, Triadimenol, Flutriafol, Difenoconazole, Fluquinconazole, Fenbuconazole, Bromuconazole, Diniconazole, Tricyclazole, Probenazole or Simeconazole, Pefurazoate, Ipconazole or Imibenconazole;

a quinoxaline compound such as Quinomethionate;

a dithiocarbamate compound such as Maneb, Zineb, Mancozeb, Polycarbamate, Metiram or Propineb;

an organic chlorine compound such as Fthalide, Chlorothalonil or Quintozene;

an imidazole compound such as Benomyl, Thiophanate-Methyl, Carbendazim or Cyazofamid;

a cyano acetamide compound such as Cymoxanil;

a phenylamide compound such as Metalaxyl, Metalaxyl M, Oxadixyl, Ofurace, Benalaxyl, Benalaxyl M, Furalaxyl or Cyprofuram;

a sulfenic acid compound such as Dichlofluanid;

a copper compound such as Cupric hydroxide or Oxine Copper;

an isoxazole compound such as Hymexazol;

an organic phosphorus compound such as Fosetyl-Al, Tolcofos-Methyl, S-benzyl O,O-diisopropylphosphorothioate, O-ethyl S,S-diphenylphosphorodithioate or aluminum ethylhydrogen phosphonate;

an N-halogenothioalkyl compound such a Captan, Captafol or Folpet;

a dicarboxylmide compound such as Procymidone, Iprodione or Vinclozolin;

a benzanilide compound such as Flutolanil, Mepronil, Zoxamid or Tiadinil;

an anilide compound such as Boscalid;

a piperazine compound such as Triforine;

a pyridine compound such as Pyrifenox;

a carbinol compound such as Fenarimol or Flutriafol;

a piperidine compound such as Fenpropidine;

a morpholine compound such as Fenpropimorph or Tridemorph;

an organic tin compound such as Fentin Hydroxide or Fentin Acetate;

an urea compound such as Pencycuron;

a cinnamic acid compound such as Dimethomorph or Flumorph;

a phenylcarbamate compound such as Diethofencarb;

a cyanopyrrole compound such as Fludioxonil or Fenpiclonil;

a strobilurin compound such as Azoxystrobin, Kresoxim-Methyl, Metominofen, Trifloxystrobin, Picoxystrobin, Oryzastrobin, Dimoxystrobin, Pyraclostrobin, Fluoxastrobin or Fluacrypyrin;

an oxazolidinone compound such as Famoxadone;

a thiazolecarboxamide compound such as Ethaboxam;

a silylamide compound such as Silthiopham;

an amino acid amide carbamate compound such as Iprovalicarb or Benthiavalicarb-isopropyl;

an imidazolidine compound such as Fenamidone;

a hydroxyanilide compound such as Fenhexamid;

a benzenesulfonamide compound such as Flusulfamide;

an oxime ether compound such as Cyflufenamid;

a phenoxyamide compound such as Fenoxanil;

an antibiotic such as Polyoxins;

a guanidine compound such as Iminoctadine;

other compound, such as Isoprothiolane, Pyroquilon, Diclomezine, Quinoxyfen, Propamocarb Hydrochloride, Spiroxamine Chloropicrin, Dazomet, Metam-sodium, Nicobifen, Metrafenone, MTF-753 (Pentiopyrad), UBF-307, Diclocymet, Proquinazid, NC-224 (Amibromdole, Amisulbrom), KIF-7767 (KUF-1204, Pyribencarb methyl, Mepyricarb) or Syngenta 446510 (Mandipropamid, Dipromandamid).

The active ingredient compound (common name; including some which are under application) of the insecticide, miticide, nematicide or soil pesticide in such another agricultural chemical, may, for example, be:

an organic phosphate compound such as Profenofos, Dichlorvos, Fenamiphos, Fenitrothion, EPN, Diazinon, Chlorpyrifos-methyl, Acephate, Prothiofos, Fosthiazate, Phosphocarb, Cadusafos, Disulfoton, Chlorpyrifos, Demeton-S-methyl, Dimethoate or Methamidophos;

a carbamate compound such as Carbaryl, Propoxur, Aldicarb, Carbofuran, Thiodicarb, Methomyl, Oxamyl, Ethiofencarb, Pirimicarb, Fenobucarb, Carbosulfan or Benfuracarb;

a nelicetoxin derivative such as Cartap, Thiocyclam or Bensultap;

an organic chlorine compound such as Dicofol or Tetradifon;

an organic metal compound such as Fenbutatin Oxide;

a pyrethroid compound such as Fenvalerate, Permethrin, Cypermethrin, Deltamethrin, Cyhalothrin, Tefluthrin, Ethofenprox, Fenpropathrin or Bifenthrin;

a benzoyl urea compound such as Diflubenzuron, Chlorfluazuron, Teflubenzuron, Flufenoxuron, Lufenuron or Novaluron;

a juvenile hormone-like compound such as Methoprene, Pyriproxyfen or Fenoxycarb;

a pyridadinone compound such as Pyridaben;

a pyrazole compound such as Fenpyroximate, Fipronil, Tebufenpyrad, Ethiprole, Tolfenpyrad, Acetoprole, Pyrafluprole or Pyriprole;

a neonicotinoide such as Imidacloprid, Nitenpyram, Acetamiprid, Thiacloprid, Thiamethoxam, Clothianidin or Dinotefuran;

a hydrazine compound such as Tebufenozide, Methoxyfenozide or Chromafenozide;

a dinitro compound, an organosulfur compound, an urea compound, a triazine compound or a hydrazone compound;

other compound, such as Flonicamid, Buprofezin, Hexythiazox, Amitraz, Chlordimeform, Silafluofen, Triazamate, Pymetrozine, Pyrimidifen, Chlorfenapyr, Indoxacarb, Acequinocyl, Etoxazole, Cyromazine, 1,3-dichloropropene, Diafenthiuron, Benclothiaz, Flufenerim, Pyridalyl, Spirodiclofen, Bifenazate, Spiromesifen, spirotetramat, Propargite, Clofentezine, Fluacrypyrim, Metaflumizone, Flubendiamide or Cyflumetofen.

Further, a microbial pesticide such as a BT agent, an insect pathogenic virus agent, entomopathogenic fugi or nematophagous fugi;

an antibiotic such as Avermectin, Emamectin-Benzoate, Milbemectin, Spinosad, Ivermectin or Lepimectin;

a natural product such as Azadirachtin.

Preferred embodiments of the present invention are as follows. However, it should be understood that the present invention is by no means restricted to such specific embodiments.

(1) An acid amide derivative of the above formula (I) or a salt thereof.

(2) The acid amide derivative of the above formula (I) or a salt thereof, wherein A is phenyl which may be substituted by X, naphthyl which may be substituted by X, heterocyclic ring which may be substituted by X, or fused heterocyclic ring which may be substituted by X; B is heterocyclic ring (excluding pyridyl) which may be substituted by Y, fused heterocyclic ring which may be substituted by Y, or naphthyl which may be substituted by Y; X is halogen, alkyl (the alkyl may be substituted by halogen, hydroxy, alkoxy, haloalkoxy, alkylthio, alkylsulfonyl, cycloalkyl, amino, monoalkylamino, dialkylamino, cyano, alkoxycarbonyl, or alkylcarbonyloxy), alkenyl, haloalkenyl, alkynyl (the alkynyl may be substituted by halogen, hydroxy, alkoxy, amino, hydroxycarbonyl, alkoxycarbonyl, or trialkylsilyl), hydroxy, cyanooxy, alkoxy (the alkoxy may be substituted by halogen, alkoxy, haloalkoxy, alkylthio, cycloalkyl, monoalkylamino, dialkylamino, cyano, or heterocyclic ring), alkenyloxy, haloalkenyloxy, alkynyloxy, haloalkynyloxy, alkylthio (the alkylthio may be substituted by halogen, cycloalkyl, or cyano), alkenylthio, haloalkenylthio, alkynylthio, haloalkynylthio, alkylsulfinyl, haloalkylsulfinyl, alkylsulfonyl, haloalkylsulfonyl, cycloalkyl which may be substituted by halogen, cycloalkyloxy which may be substituted by halogen, cycloalkylthio which may be substituted by halogen, cyano, nitro, formyl, phenyl (the phenyl may be substituted by halogen, alkyl, haloalkyl, or alkoxy), phenoxy which may be substituted by alkyl, phenylthio which may be substituted by alkyl, phenylalkyl which may be substituted by alkyl, phenylalkenyl which may be substituted by alkyl, phenylalkynyl which may be substituted by alkyl, phenylalkyloxy which may be substituted by alkyl, phenylalkenyloxy which may be substituted by alkyl, phenylalkynyloxy which may be substituted by alkyl, phenylamino which may be substituted by alkyl, —OR$^4$, —SR$^5$, —NR$^6$R$^7$, —CO$_2$R$^8$, —C(=O)NR$^8$R$^9$, —SO$_2$NR$^8$R$^9$, —CH=NR$^{10}$, or heterocyclic ring (the heterocyclic ring may be substituted by halogen, alkyl, or alkylcarbonyl); Y is halogen, alkyl (the alkyl may be substituted by halogen, alkoxy, haloalkoxy, amino, monoalkylamino, or dialkylamino), alkenyl, alkynyl, hydroxy, alkoxy, haloalkoxy, alkylthio, haloalkylthio, alkylsulfinyl, haloalkylsulfinyl, alkylsulfonyl, haloalkylsulfonyl, cycloalkyl, cyano, nitro, formyl, —OR$^4$, —NR$^6$R$^7$, —CO$_2$R$^8$, —C(=O)NR$^8$R$^9$, —SO$_2$NR$^8$R$^9$, or —CH=NR$^{10}$; each of R$^1$ and R$^2$ which are independent of each other, is hydrogen, alkyl, haloalkyl, alkoxyalkyl, alkenyl, alkynyl, or cycloalkyl, or R$^1$ and R$^2$ may together form a 3- to 6-membered saturated carbon ring; R$^3$ is hydrogen, alkyl (the alkyl may be substituted by halogen, alkoxy, haloalkoxy, alkylthio, amino, monoalkylamino, dialkylamino, or cyano), alkenyl, alkynyl, hydroxy, alkoxy, haloalkoxy, cycloalkyl, cycloalkyloxy, cyano, formyl, —C(=W$^3$)R$^{11}$, —C(=W$^3$)OR$^{12}$, or —S(O)mR$^{12}$.

(3) The acid amide derivative or a salt thereof, wherein A is phenyl which may be substituted by X, naphthyl which may be substituted by X, heterocyclic ring which may be substituted by X, or fused heterocyclic ring which may be substituted by X; B is 5-membered heterocyclic ring which may be substituted by Y, pyrazinyl, or fused heterocyclic ring which may be substituted by Y; X is halogen, alkyl, haloalkyl, alkoxyalkyl, dialkylaminoalkyl, alkynyl, trialkylsilylalkynyl, hydroxy, alkoxy, haloalkoxy, alkoxyalkoxy, cycloalkyl, nitro, phenyl, phenylalkynyl, pyridyloxy which may be substituted by haloalkyl, alkylcarbonyloxy, alkylsulfonyloxy, or heterocyclic ring (the heterocyclic ring may be substituted by halogen, alkyl, or alkylcarbonyl); Y is halogen, alkyl, haloalkyl, alkoxy, haloalkoxy, cycloalkyl, or formyl; each of R$^1$ and R$^2$ which are independent of each other, is hydrogen, or alkyl; R$^3$ is hydrogen, alkyl, alkylcarbonyl, or alkoxycarbonyl; and each of W$^1$ and W$^2$ which are independent of each other, is oxygen or sulfur.

(4) The acid amide derivative or a salt thereof according to the above (3), wherein each of W$^1$ and W$^2$ is oxygen.

(5) The acid amide derivative or a salt thereof according to the above (3), wherein B is fused heterocyclic ring which may be substituted by Y.

(6) The acid amide derivative or a salt thereof according to the above (5), wherein the fused heterocyclic ring is benzofuranyl, dihydrobenzofuranyl, benzodioxanyl or quinolyl.

(7) The acid amide derivative or a salt thereof according to the above (3), wherein B is 5-membered heterocyclic ring which may be substituted by Y; X is halogen, alkyl, haloalkyl, alkynyl, hydroxy, alkoxy, haloalkoxy, alkoxyalkoxy, cycloalkyl, nitro, phenylalkyl, pyridyloxy which may be substituted by haloalkyl, alkylcarbonyloxy, or heterocyclic ring (the heterocyclic ring may be substituted by halogen, alkyl, or alkylcarbonyl); Y is halogen, alkyl, haloalkyl, or alkoxy; R$^3$ is hydrogen, alkylcarbonyl, or alkoxycarbonyl; and each of W$^1$ and W$^2$ is oxygen.

(8) The acid amide derivative or a salt thereof according to the above (3) or (7), wherein B is furyl which may be substituted by Y, thienyl which may be substituted by Y, pyrrolyl which may be substituted by Y, oxazolyl which may be substituted by Y, isoxazolyl which may be substituted by Y, thiazolyl which may be substituted by Y, isothiazolyl which may be substituted by Y, pyrazolyl which may be substituted by Y, or thiadiazolyl which may be substituted by Y.

(9) The acid amide derivative or a salt thereof according to the above (8), wherein B is furyl which may be substituted by Y, thienyl which may be substituted by Y, pyrrolyl which may be substituted by Y, oxazolyl which may be substituted by Y, thiazolyl which may be substituted by Y, isothiazolyl which may be substituted by Y, pyrazolyl which may be substituted by Y, or thiadiazolyl which may be substituted by Y.

(10) The acid amide derivative or a salt thereof according to the above (9), wherein B is furyl substituted by Y.

(11) The acid amide derivative or a salt thereof according to the above (9), wherein B is thienyl substituted by Y.

(12) The acid amide derivative or a salt thereof according to the above (9), wherein B is pyrazolyl substituted by Y.

(13) An acid amide derivative of the above formula (I-α) or a salt thereof.

(14) The acid amide derivative of the above formula (I-α) or a salt thereof, wherein B is 5-membered heterocyclic ring which may be substituted by Y, pyrazinyl, or fused heterocyclic ring which may be substituted by Y; X$^α$ is fluorine, chlorine, iodine, alkyl, haloalkyl, alkoxyalkyl, dialkylaminoalkyl, alkynyl, trialkylsilylalkynyl, hydroxy, alkoxy, haloalkoxy, alkoxyalkoxy, cycloalkyl, nitro, phenyl, phenylalkynyl, pyridyloxy which may be substituted by haloalkyl, alkylcarbonyloxy, alkylsulfonyloxy, or heterocyclic ring (the heterocyclic ring may be substituted by halogen, alkyl, or alkylcarbonyl); Y is halogen, alkyl, haloalkyl, alkoxy, haloalkoxy, cycloalkyl, or formyl; each of R$^1$ and R$^2$ which are independent of each other, is hydrogen or alkyl; R$^3$ is hydrogen, alkyl, alkylcarbonyl, or alkoxycarbonyl; and each of W$^1$ and W$^2$ which are independent of each other, is oxygen, or sulfur.

(15) The acid amide derivative or a salt thereof according to the above (14), wherein each of W$^1$ and W$^2$ is oxygen.

(16) The acid amide derivative or a salt thereof according to the above (14), wherein B is the fused heterocyclic ring which may be substituted by Y.

(17) The acid amide derivative or a salt thereof according to the above (16), wherein the fused heterocyclic ring is benzofuranyl, dihydrobenzofuranyl, benzodioxanyl or quinolyl.

(18) The acid amide derivative or a salt thereof according to the above (14), wherein B is 5-membered heterocyclic ring which may be substituted by Y; X$^α$ is fluorine, chlorine, iodine, alkyl, haloalkyl, alkynyl, hydroxy, alkoxy, haloalkoxy, alkoxyalkoxy, cycloalkyl, nitro, phenylalkynyl, pyridyloxy which may be substituted by haloalkyl, alkylcarbonyloxy, or heterocyclic ring (the heterocyclic ring may be substituted by halogen, alkyl, or alkylcarbonyl); Y is halogen, alkyl, haloalkyl, or alkoxy; $R^3$ is hydrogen, alkylcarbonyl, or alkoxycarbonyl; and each of $W^1$ and $W^2$ is oxygen.

(19) The acid amide derivative or a salt thereof according to the above (14) or (18), wherein B is furyl which may be substituted by Y, thienyl which may be substituted by Y, pyrrolyl which may be substituted by Y, oxazolyl which may be substituted by Y, isoxazolyl which may be substituted by Y, thiazolyl which may be substituted by Y, isothiazolyl which may be substituted by Y, imidazolyl which may be substituted by Y, pyrazolyl which may be substituted by Y, or thiadiazolyl which may be substituted by Y.

(20) The acid amide derivative or a salt thereof according to the above (19), wherein B is furyl which may be substituted by Y, thienyl which may be substituted by Y, pyrrolyl which may be substituted by Y, oxazolyl which may be substituted by Y, isoxazolyl which may be substituted by Y, thiazolyl which may be substituted by Y, isothiazolyl which may be substituted by Y, pyrazolyl which may be substituted by Y, or thiadiazolyl which may be substituted by Y.

(21) The acid amide derivative or a salt thereof according to the above (20), wherein B is furyl substituted by Y.

(22) The acid amide derivative or a salt thereof according to the above (20), wherein B is thienyl substituted by Y.

(23) The acid amide derivative or a salt thereof according to the above (20), wherein B is pyrazolyl substituted by Y.

(24) The acid amide derivative or a salt thereof according to the above (3) or (14), wherein A is phenyl which may be substituted by X, naphthyl which may be substituted by X, benzodioxolanyl which may be substituted by X, or benzodioxanyl which may be substituted by X; B is furyl which may be substituted by Y, thienyl which may be substituted by Y, or pyrazolyl which may be substituted by Y; X is halogen, alkyl, haloalkyl, alkoxy, or haloalkoxy; Y is halogen, alkyl, haloalkyl, alkoxy, or haloalkyl; $R^3$ is hydrogen; and each of $W^1$ and $W^2$ is oxygen.

(25) The acid amide derivative or a salt thereof according to the above (24), wherein B is furyl substituted by Y, thienyl substituted by Y, or pyrazolyl substituted by Y.

(26) The acid amide derivative or a salt thereof according to the above (24), wherein B is furyl substituted by Y, thienyl substituted by Y, pyrazolyl substituted by Y, and Y is halogen, alkyl or haloalkyl.

(27) The acid amide derivative or a salt thereof according to the above (24), wherein A is phenyl substituted by X, or benzodioxolanyl substituted by X, and B is furyl substituted by Y, thienyl substituted by Y, or pyrazolyl substituted by Y.

(28) The acid amide derivative or a salt thereof according to the above (24), wherein A is phenyl substituted by X, or benzodioxolanyl substituted by X; B is furyl substituted by Y, thienyl substituted by Y, or pyrazolyl substituted by Y; X is halogen, alkyl, or alkoxy; and Y is halogen, alkyl, or haloalkyl.

(29) The acid amide derivative or a salt thereof according to the above (24), wherein A is phenyl substituted by X, or benzodioxolanyl substituted by X; B is furyl substituted by Y, thienyl substituted by Y, or pyrazolyl substituted by Y; each of $R^1$ and $R^2$ is alkyl; X is halogen, alkyl, or alkoxy; and Y is halogen, alkyl, or haloalkyl.

(30) The acid amide derivative or a salt thereof according to any one of the above (24) to (29), wherein B is furyl substituted by Y.

(31) The acid amide derivative or a salt thereof according to any one of the above (24) to (29), wherein B is thienyl substituted by Y.

(32) The acid amide derivative or a salt thereof according to any one of the above (24) to (29), wherein B is pyrazolyl substituted by Y.

(33) A fungicidal composition containing the acid amide derivative or a salt thereof as defined in any one of the above (1) to (32) as an active ingredient.

(34) A mixed fungicidal composition containing the acid amide derivative or a salt thereof as defined in any one of the above (1) to (32), and another fungicidally active ingredient compound, as active ingredients.

(35) The mixed fungicidal composition according to the above (34), wherein said another fungicidally active ingredient compound is at least one member selected from the group consisting of an anilinopyrimidine compound, a pyridinamine compound, an azole compound, a quinoxaline compound, a dithiocarbamate compound, an organic chlorine compound, an imidazole compound, a cyano acetamide compound, a phenylamide compound, a sulfenic acid compound, a copper compound, an isoxazole compound, an organic phosphorus compound, an N-halogenothioalkyl compound, a dicarboxylmide compound, a benzanilide compound, an anilide compound, a piperazine compound, a pyridine compound, a carbinol compound, a piperidine compound, a morpholine compound, an organic tin compound, an urea compound, a cinnamic acid compound, a phenylcarbamate compound, a cyanopyrrole compound, a strobilurin compound, an oxazolidinone compound, a thiazolecarboxamide compound, a silylamide compound, an amino acid amide carbamate compound, an imidazolidine compound, a hydroxyanilide compound, a benzenesulfonamide compound, an oxime ether compound, a phenoxyamide compound, an antibiotic, a guanidine compound, isoprothiolane, pyroquilon, diclomezine, quinoxyfen, propamocarb hydrochloride, spiroxamine, chloropicrin, dazomet, metam-sodium, nicobifen, metrafenone, MTF-753, UBF-307, diclocymet, proquinazid, NC-224, KIF-7767 and Syngenta 446510.

(36) The mixed fungicidal composition according to the above (35), wherein said another fungicidally active ingredient compound is at least one member selected from the group consisting of a pyridinamine compound, an azole compound, a dithiocarbamate compound, an organic chlorine is compound, an imidazole compound, a copper compound, a dicarboxylmide compound, an anilide compound, a piperazine compound, a pyridine compound, a carbinol compound, a phenylcarbamate compound, a cyanopyrrole compound, a strobilurin compound, a hydroxyanilide compound, MTF-753, and KIF-7767.

(37) The mixed fungicidal composition according to the above (36), wherein said another fungicidally active ingredient compound is at least one member selected from the group consisting of Fluazinam, Triadimefon, Bitertanol, Triflumizole, Etaconazole, Propiconazole, Penconazole, Flusilazole, Myclobutanil, Cyproconazole, Terbuconazole, Hexaconazole, Furconazole-cis, Prochloraz, Metconazole, Epoxiconazole, Tetraconazole, Oxpoconazole fumarate, Sipconazole, Prothioconazole, Triadimenol, Flutriafol, Difenoconazole, Fluquinconazole, Fenbuconazole, Bromuconazole, Diniconazole, tricyclazole, probenazole, Simeconazole, Pefurazoate, Ipconazole, Imibenconazole, Maneb, Zineb, Mancozeb, Polycarbamate, Metiram, Propineb, Fthalide, Chlorothalonil, Quintozene, Benomyl, Thiophanate-Methyl, Carbendazim, Cyazofamid, Cupric hydroxide, Oxine Copper, Procymidone, Iprodione, Vinclozolin, Boscalid, Diethofencarb, Fludioxonil, Fenpiclonil, Azoxystrobin, Kresoxim-Methyl, Metominofen, Trifloxystrobin, Picoxystrobin, Oryzastrobin, Dimoxystrobin, Pyraclostrobin, Fluoxastrobin, Fluacrypyrin, Fenhexamid, Polyoxins, Iminoctadine, MTF-753, and KIF-7767.

(38) A method for controlling noxious fungi, which comprises applying an effective amount of the acid amide derivative or a salt thereof as defined in any one of the above (1) to (32).

(39) A method for controlling plant diseases, which comprises applying an effective amount of the acid amide derivative or a salt thereof as defined in any one of the above (1) to (32).

(40) A method for protecting crop plants, which comprises applying an effective amount of the acid amide derivative or a salt thereof as defined in any one of the above (1) to (32).

(41) A method for improving crop yields, which comprises applying an effective amount of the acid amide derivative or a salt thereof as defined in any one of the above (1) to (32).

Now, the present invention will be described in further detail with reference to Examples. However, it should be understood that the present invention is by no means restricted thereto. Firstly, Preparation Examples for the acid amide derivative of the formula (I), (I-α) or a salt thereof will be described.

Preparation Example 1

Preparation of N-[(3',4'-dichloro-1,1-dimethyl) phenacyl]-2-methyl-3-furancarboxamide (After-Mentioned Compound No. 1-57)

(1) A mixture comprising 10.0 g of 3,4-dichlorobenzoyl chloride, 9.31 g of ethyl 2-bromoisobutyrate and 90 ml of anhydrous diethyl ether, was dropwise added to 3.12 g of zinc in a nitrogen atmosphere, followed by a reaction for 15 hours under reflux. The reaction mixture was filtered through celite, and the filtrate was washed with 20% sulfuric acid and then with water. The organic layer was dried over anhydrous magnesium sulfate and then concentrated under reduced pressure. The residue was purified by silica gel column chromatography (developing solvent: ethyl acetate/n-hexane=1/19) to obtain 8.7 g of oily ethyl 2-(3',4'-dichlorobenzoyl)isobutyrate. The NMR spectrum data of this product is as follows.

$^1$H-NMR δppm (Solvent: CDCl$_3$/400 MHz)
1.11 (t, 3H), 1.52 (s, 6H), 4.14 (q, 2H), 7.48 (d, 1H), 7.63 (dd, 1H), 7.96 (d, 1H)

(2) A mixture comprising 8.7 g of ethyl 2-(3',4'-dichlorobenzoyl)isobutyrate, 14.2 ml of sulfuric acid, 14.2 ml of water and 40 ml of acetic acid, was reacted for 15 hours under reflux. The reaction mixture was put into ice water and extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/19) to obtain 6.47 g of oily 3,4-dichloroisobutyrophenone. The NMR spectrum data of this product is as follows.

$^1$H-NMR δppm (Solvent: CDCl$_3$/400 MHz)
1.21 (d, 6H), 3.46 (m, 1H), 7.55 (d, 1H), 7.79 (dd, 1H), 8.02 (d, 1H)

(3) 9.32 g of phenyltrimethylammonium tribromide was added to a mixture comprising 6.47 g of 3,4-dichloroisobutyrophenone and 100 ml of tetrahydrofuran, followed by a reaction for 4 hours at room temperature. The reaction mixture was filtered, and the filtrate was concentrated under reduced pressure to obtain 6.39 g of oily α-bromo-3,4-dichloroisobutyrophenone. The NMR spectrum data of this product is as follows.

$^1$H-NMR δppm (Solvent: CDCl$_3$/300 MHz)
2.01 (s, 6H), 7.50 (d, 1H), 8.0 (dd, 1H), 8.20 (d, 1H)

(4) 2.8 g of sodium azide was added to a mixture comprising 6.39 g of α-bromo-3,4-dichloroisobutyrophenone and 60 ml dimethyl sulfoxide, followed by a reaction for one hour at 50° C. The reaction mixture was put into water and extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/9) to obtain 6.34 g of oily α-azide-3,4-dichloroisobutyrophenone. The NMR spectrum data of this product is as follows.

$^1$H-NMR δppm (Solvent: CDCl$_3$/300 MHz)
1.60 (s, 6H), 7.53 (d, 1H), 7.97 (dd, 1H), 8.20 (d, 1H)

(5) 7.74 g of triphenylphosphine was added to a mixture comprising 6.34 g of α-azide-3,4-dichloroisobutyrophenone, 90 ml of tetrahydrofuran and 3.2 ml of water, followed by a reaction for 23 hours at room temperature. The reaction mixture was concentrated under reduced pressure. To the residue, water and then hydrochloric acid were added to bring it to be weakly acidic, followed by washing with diethyl ether. The aqueous layer was neutralized with an aqueous sodium hydroxide solution and extracted with diethyl ether. The organic layer was dried over anhydrous magnesium sulfate and concentrated under reduced pressure. To the residue, ethyl acetate was added, and hydrogen chloride gas was introduced under cooling with ice. Formed solid was collected by filtration and dried to obtain 5.92 g of α-amino-3,4-dichloroisobutyrophenone hydrochloride.

(6) 0.31 g of triethylamine was added to a mixture comprising 0.3 g of α-amino-3,4-dichloroisobutyrophenone hydrochloride and 10 ml of tetrahydrofuran, followed by stirring for 5 hours at room temperature. The mixture was concentrated under reduced pressure. To a mixture comprising the obtained residue, 0.195 g of 2-methyl-3-furancarboxylic acid and 20 ml of dichloromethane, a mixture comprising 0.29 g of N,N'-dicyclohexylcarbodiimide and 10 ml of dichloromethane, was dropwise added under cooling with ice, followed by a reaction for 15 hours at room temperature. The reaction mixture was filtered, and the filtrate was diluted with dichloromethane, and washed with an aqueous potassium carbonate solution and then with water. The organic layer was dried over anhydrous sodium sulfate and then concentrated under reduced pressure. The residue was purified by silica gel column chromatography (developing solvent: ethyl acetate/n-hexane=1/9) to obtain 0.08 g of the desired product having a melting point of from 175 to 178° C. The NMR spectrum data of this product is as follows.

$^1$H-NMR δppm (Solvent: CDCl$_3$/400 MHz)
1.71 (s, 6H), 2.43 (s, 3H), 6.28 (s, 1H), 6.44 (d, 1H), 7.26 (d, 1H), 7.44 (d, 1H), 7.84 (dd, 1H), 8.11 (d, 1H)

Preparation Example 2

Preparation of N-[(3'-difluoromethoxy-1,1-dimethyl) phenacyl]-5-chloro-1,3-dimethyl-4-pyrazole carboxamide (After-Mentioned Compound No. 1-72)

(1) A Grignard reagent prepared by using 0.75 g of magnesium, 4.46 g of 2-bromopropane and 24 ml of anhydrous diethyl ether, was dropwise added to a mixture comprising 4.09 g of 3-difluoromethoxybenzonitrile and 20 ml of anhydrous diethyl ether. After completion of the dropwise addition, the mixture was reacted at room temperature for 27 hours. The reaction mixture was put into ice water, and 6N sulfuric acid was added to bring the mixture to be weakly acidic, followed by stirring for 0.5 hour. The mixture was extracted with diethyl ether and washed with water. The organic layer was dried over anhydrous magnesium sulfate and then concentrated under reduced pressure. The residue was purified by silica gel column chromatography (developing solvent: ethyl acetate/n-hexane=1/19), to obtain 2.04 g of 3-difluoromethoxyisobutyrophenone. The NMR spectrum data of this product is as follows.

$^1$H-NMR δppm (Solvent: CDCl$_3$/300 MHz)
1.23 (d, 6H), 3.52 (m, 1H), 6.56 (t, 1H), 7.32 (dd, 1H), 7.48 (t, 1H), 7.70 (s, 1H), 7.80 (d, 1H)

(2) 3.58 g of phenyltrimethylammonium tribromide was added to a mixture comprising 2.04 g of 3-difluoromethoxyisobutyrophenone and 30 ml of tetrahydrofuran, followed by a reaction for two hours at room temperature. The reaction mixture was filtered, and the filtrate was concentrated under reduced pressure to obtain 2.79 g of oily α-bromo-3-difluoromethoxyisobutyrophenone.

(3) 1.24 g of sodium azide was added to a mixture comprising 2.79 g of α-bromo-3-difluoromethoxyisobutyrophenone and 35 ml of dimethyl sulfoxide, followed by a reaction for one hour at 50° C. The reaction mixture was put into water and extracted with ethyl acetate, followed by washing with water. The organic layer was dried over anhydrous magnesium sulfate and then concentrated under reduced pressure. The residue was purified with silica gel column chromatography (developing solvent: ethyl acetate/n-hexane=1/9) to obtain 2.21 g of oily α-azide-3-difluoromethoxyisobutyrophenone. The NMR spectrum data of this product is as follows.

$^1$H-NMR δppm (Solvent: CDCl$_3$/300 MHz)
1.61 (s, 6H), 6.56 (t, 1H), 7.34 (dd, 1H), 7.48 (t, 1H), 7.86 (s, 1H), 7.98 (d, 1H)

(4) A mixture comprising 2.18 g of α-azide-3-difluoromethoxyisobutyrophenone, 35 ml of methanol and 0.109 g of 5% palladium carbon, was reacted for 1.5 hours at room temperature in a hydrogen atmosphere. The reaction mixture was filtered through celite, and the filtrate was concentrated under reduced pressure. To the residue, ethyl acetate was added, and hydrogen chloride gas was introduced under cooling with ice, followed by concentration under reduced pressure to obtain 1.76 g of α-amino-3-difluoromethoxyisobutyrophenone hydrochloride.

(5) 0.33 g of triethylamine was added to a mixture comprising 0.3 g of α-amino-3-difluoromethoxyisobutyrophenone hydrochloride and 10 ml of tetrahydrofuran, and a mixture comprising 0.25 g of 5-chloro-1,3-dimethyl-4-pyrazolecarbonyl chloride and 5 ml of tetrahydrofuran, was dropwise added thereto under cooling with ice. After completion of the dropwise addition, the mixture was reacted at room temperature for 3 hours. The reaction mixture was extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/4) to obtain 0.23 g of the desired product having a melting point of from 138 to 139° C. The NMR spectrum data of this product is as follows.

$^1$H-NMR δppm (Solvent: CDCl$_3$/400 MHz)
1.75 (s, 6H), 2.28 (s, 3H), 3.80 (s, 3H), 6.50 (t, 1H), 6.80 (s, 1 H), 7.23 (dd, 1H), 7.38 (t, 1H), 7.84 (s, 1H), 7.86 (d, 1H)

Preparation Example 3

Preparation of N-[2-(2'-naphthylcarbonyl)-2-propyl]-5-chloro-1,3-dimethyl-4-pyrazolecarboxamide (Compound No. 2-1)

(1) A Grignard reagent prepared by using 0.61 g of magnesium, 3.6 g of 2-bromopropane and 18 ml of anhydrous diethyl ether, was dropwise added to a mixture comprising 3.0 g of 2-naphthonitrile and 20 ml of anhydrous diethyl ether. After completion of the dropwise addition, the mixture was reacted for 12 hours under reflux. The reaction mixture was put into ice water, and 6N sulfuric acid was added to bring the mixture to be weakly acidic, followed by stirring for 0.5 hour. The mixture was extracted with ethyl acetate, followed by washing with water. The organic layer was dried over anhydrous magnesium sulfate, and then concentrated under reduced pressure. The residue was purified by silica gel column chromatography (developing solvent: ethyl acetate/n-hexane=1/50) to obtain 1.14 g of 2-naphthyl isopropyl ketone. The NMR spectrum data of this product is as follows.

$^1$H-NMR δppm (Solvent: CDCl$_3$/400 MHz)
1.27 (d, 6H), 3.73 (m, 1H), 7.53 to 7.65 (m, 2H), 7.86 to 7.92 (m, 2H), 7.97 (d, 1H), 8.03 (dd, 1H), 8.48 (d, 1H)

(2) 2.16 g of phenyltrimethylammonium tribromide was added to a mixture comprising 1.14 g of 2-naphthyl isopropyl ketone and 25 ml of tetrahydrofuran, and the mixture was reacted at room temperature for 3 hours. The reaction mixture was filtered, and the filtrate was concentrated under reduced pressure to obtain 1.59 g of oily α-bromoisopropyl 2-naphthyl ketone.

(3) 0.75 g of sodium azide was added to a mixture comprising 1.59 g of α-bromoisopropyl 2-naphthyl ketone and 40 ml of dimethyl sulfoxide, and the mixture was reacted at 50° C. for 1.5 hours. The reaction mixture was put into water and extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/9) to obtain 1.19 g of oily α-azideisopropyl 2-naphthyl ketone.

The NMR spectrum data of this product is as follows.
$^1$H-NMR δppm (Solvent: CDCl$_3$/400 MHz)
1.68 (s, 1H), 7.54 to 7.66 (m, 2H), 7.86 to 7.90 (m, 2H), 7.98 (d, 1H), 8.10 (dd, 1H), 8.74 (d, 1H)

(4) A mixture comprising 0.3 g of α-azideisopropyl 2-naphthyl ketone, 10 ml of methanol and 15 mg of 5% palladium carbon, was reacted for one hour at room temperature in a hydrogen atmosphere. The reaction mixture was filtered through celite, and the filtrate was concentrated under reduced pressure to obtain 0.26 g of oily α-aminoisopropyl 2-naphthyl ketone (5) 0.19 g of triethylamine was added to a mixture comprising 0.26 g of α-aminoisopropyl 2-naphthyl ketone and 10 ml of tetrahydrofuran, and a mixture comprising 0.24 g of 5-chloro-1,3-dimethyl-4-pyrazolecarbonyl chloride and 5 ml of tetrahydrofuran, was dropwise added thereto under cooling with ice. After the dropwise addition, the mixture was reacted for 15 hours at room temperature. The reaction mixture was extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=2/3) to obtain 0.15 g of the desired product having a melting point of from 145 to 147° C. The NMR spectrum data of this product is as follows.

$^1$H-NMR δppm (Solvent: CDCl$_3$/300 MHz)
1.87 (s, 6H), 2.28 (s, 3H), 3.79 (s, 3H), 7.05 (s, 1H), 7.48 to 7.58 (m, 2H), 7.80 to 7.90 (m, 3H), 8.05 (dd, 1H), 8.56 (d, 1H)

Preparation Example 4

Preparation of N-[2-[(2',2',3',3'-tetrafluoro-1',4'-benzodioxan-6'-yl)carbonyl]isopropyl]-3-methyl-2-thiophene carboxamide (After-Mentioned Compound No. 4-10)

(1) 7.3 ml of n-butyllithium (1.57M n-hexane solution) was dropwise added at −50° C. in a nitrogen atmosphere to a mixture comprising 3.0 g of 6-bromo-2,2,3,3-tetrafluoro-1,4-benzodioxane and 38 ml of diethyl ether, followed by stirring for 30 minutes at the same temperature. Then, 0.83 g of isobutylaldehyde was dropwise added at a temperature of at most −70° C., and the mixture was heated to room temperature and reacted for 15 hours. The reaction mixture was put into water and adjusted to be weakly acidic with hydrochloric acid, and extracted with diethyl ether. The organic layer was washed with water, dried over magnesium sulfate and then concentrated under reduced pressure. The residue was purified by silica gel column chromatography (developing solvent: ethyl acetate/n-hexane=1/9) to obtain 1.8 g of oily 1-(2',2',3',3'-tetrafluoro-1',4'-benzodioxan-6'-yl)-2-methylpropanol. The NMR spectrum data of this product is as follows.

$^1$H-NMR δppm (Solvent: CDCl$_3$/400 MHz)
0.83 (d, 3H), 0.96 (d, 3H), 1.92 (m, 1H), 4.40 (d, 1H), 6.90 (d, 1H), 7.10 (s, 2H), 7.14 (s, 1H)

(2) A mixture comprising 1.8 g of 1-(2',2',3',3'-tetrafluoro-1',4'-benzodioxan-6'-yl)-2-methylpropanol and 7 ml of dichloromethane, was added to a mixture comprising 2.08 g of pyridinium chlorochromate, 1.05 g of sodium acetate and 20 ml of dichloromethane, followed by a reaction for two hours at room temperature. The reaction mixture was filtered through celite, and the filtrate was concentrated under reduced pressure. The residue was purified by silica gel column chromatography (developing solvent: ethyl acetate/n-hexane=1/19) to obtain 1.40 g of oily 2,2,3,3-tetrafluoro-1,4-benzodioxan-6-yl isopropyl ketone. The NMR spectrum data of this product is as follows.

$^1$H-NMR δppm (Solvent: CDCl$_3$/400 MHz)
1.23 (d, 6H), 3.48 (m, 1H), 7.24 (d, 1H), 7.78 (d, 1H), 7.81 (dd, 1H)

(3) 1.89 g of phenyltrimethylammonium tribromide was added to a mixture comprising 1.40 g of 2,2,3,3-tetrafluoro-1,4-benzodioxan-6-yl isopropyl ketone and 19.7 ml of tetrahydrofuran, followed by a reaction for two hours at room temperature. The reaction mixture was filtered, and the filtrate was concentrated under reduced pressure to obtain 1.78 g of oily α-bromoisopropyl 2,2,3,3-tetrafluoro-1,4-benzodioxan-6-yl ketone.

(4) 0.65 g of sodium azide was added to a mixture comprising 1.78 g of α-bromoisopropyl 2,2,3,3-tetrafluoro-1,4-benzodioxan-6-yl ketone and 10 ml of dimethyl sulfoxide, followed by a reaction for two hours at 50° C. The reaction mixture was put into water, and extracted with diethyl ether, followed by washing with water. The organic layer was dried over anhydrous magnesium sulfate and then concentrated under reduced pressure. The residue was purified by silica gel column chromatography (developing solvent: ethyl acetate/n-hexane=1/19) to obtain 1.5 g of oily α-azideisopropyl 2,2,3,3-tetrafluoro-1,4-benzodioxan-6-yl ketone. The NMR spectrum data of this product is as follows.

$^1$H-NMR δppm (Solvent: CDCl$_3$/400 MHz)
1.61 (s, 6H), 7.23 (d, 1H), 8.01 to 8.03 (m, 2H)

(5) A mixture comprising 0.25 g of α-azideisopropyl 2,2,3,3-tetrafluoro-1,4-benzodioxan-6-yl ketone, 15 ml of methanol and 13 mg of 5% palladium carbon, was reacted for one hour at room temperature in a hydrogen atmosphere. The reaction mixture was filtered through celite, and the filtrate was concentrated under reduced pressure to obtain 0.23 g of oily α-aminoisopropyl 2,2,3,3-tetrafluoro-1,4-benzodioxan-6-yl ketone.

(6) 0.16 g of triethylamine was added to a mixture comprising 0.23 g of α-aminoisopropyl 2,2,3,3-tetrafluoro-1,4-benzodioxan-6-yl ketone and 10 ml of tetrahydrofuran, and a mixture comprising 0.13 g of 3-methyl-2-thiophene carbonyl chloride and 5 ml of tetrahydrofuran, was dropwise added thereto under cooling with ice, followed by a reaction for 3 hours at room temperature. The reaction mixture was extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/4) to obtain 0.23 g of the desired product having a melting point of from 120 to 122° C. The NMR spectrum data of this product is as follows.

$^1$H-NMR δppm (Solvent: CDCl$_3$/300 MHz)
1.76 (s, 6H), 2.39 (s, 3H), 6.54 (s, 1H), 6.84 (d, 1H), 7.24 (d, 1H), 7.42 (d, 1H), 7.84 (s, 1H), 7.96 (s, 1H)

Preparation Example 5

Preparation of N-[(3',4'-dichloro-1,1-dimethyl)phenacyl]-3-methyl-2-thiophene carboxamide (After-Mentioned Compound No. 1-20)

303 mg of triethylamine was added to a mixture comprising 268 mg of α-amino-3,4-dichloroisobutyrophenone hydrochloride obtained in accordance with the process of (1) to (5) in the above Preparation Example 1 and 5 ml of tetrahydrofuran, and a mixture comprising 265 mg of 3-methyl-2-thiophene carbonyl chloride and 2.5 ml of tetrahydrofuran, was dropwise added thereto under cooling with ice. After completion of the dropwise addition, the mixture was reacted for 3 hours at room temperature. The reaction mixture was extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/3) to obtain 180 mg of the desired product having a melting point of 141° C. The NMR spectrum data of this product is as follows.

$^1$H-NMR δppm (Solvent: CDCl$_3$/400 MHz)
1.72 (s, 6H), 2.37 (s, 3H), 6.53 (s, 1H), 6.85 (d, 1H), 7.25 (d, 1H), 7.43 (d, 1H), 7.86 (dd, 1H), 8.13 (s, 1H)

Preparation Example 6

Preparation of N-[(4'-methoxy-2'-methyl-1,1-dimethyl)phenacyl]-3-methyl-2-thiophene carboxamide (After-Mentioned Compound No. 1-160)

(1) A mixture comprising 5.7 g of isobutylyl chloride and 5 ml of carbon disulfide, was dropwise added at most 10° C. to a mixture comprising 7.15 g of aluminum chloride and 20 ml of carbon disulfide, followed by a reaction for 0.5 hour. Then, a mixture comprising 5.0 g of m-cresol and 5 ml of carbon disulfide was dropwise added at most 5° C., followed by a reaction for 4 hours at room temperature. The reaction mixture was put into a mixture of ice water and hydrochloric acid and extracted with methylene chloride, followed by washing with water. The organic layer was dried over anhydrous sodium sulfate and then concentrated under reduced pressure. To the residue, 60 ml of tetrahydrofuran, 30 ml of water and 3.7 g of sodium hydroxide, were added, followed by a reaction for 1.5 hours at room temperature. The reaction mixture was concentrated under reduced pressure, then put into ice water and adjusted to be weakly acidic with dilute sulfuric acid, and then extracted with ethyl acetate. The organic layer was dried over anhydrous magnesium sulfate and then concentrated under reduced pressure. The residue was purified by silica gel column chromatography (developing solvent: ethyl acetate/n-hexane=1/9) to obtain 2.45 g of solid 4-hydroxy-2-methyl-isobutyrophenone. The NMR spectrum data of this product is as follows.

$^1$H-NMR δppm (Solvent: CDCl$_3$/400 MHz)

1.15 (d, 6H), 2.43 (s, 3H), 3.40 (m, 1H), 6.70 (m, 2H), 7.57 (d, 1 H)

(2) A mixture comprising 0.62 g of dimethyl sulfate and 3 ml of dimethylformamide, was added to a mixture comprising 0.8 g of 4-hydroxy-2-methyl-isobutyrophenone, 0.68 g of potassium carbonate and 15 ml of dimethylformamide, followed by a reaction for 3 hours at room temperature. The reaction mixture was put into water and extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/9) to obtain 0.59 g of oily 4-methoxy-2-methylisobutyrophenone. The NMR spectrum data of this product is as follows.

$^1$H-NMR δppm (Solvent: CDCl$_3$/400 MHz)

1.13 (d, 6H), 2.46 (s, 1H), 3.38 (m, 1H), 6.72 (m, 2H), 7.59 (d, 1 H)

(3) 1.16 g of phenyltrimethyl ammonium tribromide was added to a mixture comprising 0.59 g of 4-methoxy-2-methylisobutyrophenone and 15 ml of tetrahydrofuran, followed by a reaction for 2.5 hours at room temperature. Diethyl ether was added to the reaction mixture, and the insoluble matter was filtered off. The filtrate was concentrated under reduced pressure to obtain 0.7 g of oily α-bromo-4-methoxy-2-methylisobutyrophenone.

(4) 0.4 g of sodium azide was added to a mixture comprising 0.7 g of α-bromo-4-methoxy-2-methylisobutyrophenone and 8 ml of dimethyl sulfoxide, followed by a reaction for 1.5 hours at 50° C. The reaction mixture was put into water and extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/9) to obtain 0.67 g of oily α-azide-4-methoxy-2-methylisobutyrophenone. The NMR spectrum data of this product is as follows.

$^1$H-NMR δppm (Solvent: CDCl$_3$/300 MHz)

1.54 (s, 6H), 2.33 (s, 1H), 3.81 (s, 3H), 6.72 (dd, 1H), 6.75 (d, 1H), 7.61 (d, 1H)

(5) A mixture comprising 0.25 g of α-azide-4-methoxy-2-methylisobutyrophenone, 10 ml of methanol and 13 mg of 5% palladium carbon, was reacted for 3 hours at room temperature in a hydrogen atmosphere. The reaction mixture was filtered through celite, and the filtrate was concentrated under reduced pressure to obtain 0.23 g of oily α-amino-4-methoxy-2-methylisobutyrophenone.

(6) 0.13 g of triethylamine was added to a mixture comprising 0.22 g of α-amino-4-methoxy-2-methylisobutyrophenone and 12 ml of tetrahydrofuran, and a mixture comprising 0.17 g of 3-methyl-2-thiophene carbonyl chloride and 3 ml of tetrahydrofuran, was dropwise added thereto under cooling with ice. After completion of the dropwise addition, the mixture was reacted at room temperature for two hours. The reaction mixture was extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/3) to obtain 0.35 g of the desired product having a melting point of from 99 to 101° C. The NMR spectrum data of this product is as follows.

$^1$H-NMR δppm (Solvent: CDCl$_3$/300 MHz)

1.77 (s, 6H), 2.38 (s, 3H), 2.45 (s, 3H), 6.81 (dd, 1H), 6.71 (s, 1H), 6.85 (m, 2H), 7.26 (d, 1H), 7.49 (d, 1H)

Preparation Example 7

Preparation of N-[(3',4'-dimethoxy-1,1-dimethyl)phenacyl]-3-methyl-2-thiophene carboxamide (After-Mentioned Compound No. 1-535)

(1) An isopropyl magnesium bromide ether solution prepared by using 5.6 g of 2-bromopropane, 0.94 g of magnesium and 30 ml of diethyl ether, was dropwise added to a mixture comprising 5.0 g of 3,4-dimethoxybenzaldehyde and 50 ml of diethyl ether, followed by a reaction for 15 hours under reflux. The reaction mixture was put into ice water, and dilute sulfuric acid was added, followed by stirring. Then, the mixture was extracted with methylene chloride, followed by washing with water. The organic layer was dried over anhydrous sodium sulfate and then concentrated under reduced pressure to obtain 6.3 g of oily 1-(3',4'-dimethoxyphenyl)-2-methylpropanol.

(2) A mixture comprising 6.28 g of 1-(3',4'-dimethoxyphenyl)-2-methylpropanol and 30 ml of dichloromethane, was added to a mixture comprising 6.5 g of pyridinium chlorochromate, 4.9 g of sodium acetate and 100 ml of dichloromethane, followed by a reaction for 15 hours at room temperature. The reaction mixture was filtered through celite, and the filtrate was concentrated under reduced pressure. The residue was purified by silica gel column chromatography (developing solvent: ethyl acetate/n-hexane=3/7) to obtain 3.9 g of oily 3,4-dimethoxyisobutyrophenone. The NMR spectrum data of this product is as follows.

$^1$H-NMR δppm (Solvent: CDCl$_3$/400 MHz)

1.70 (d, 6H), 3.50 (m, 1H), 3.89 (s, 3H), 3.90 (s, 3H), 6.85 (d, 1H), 7.50 (d, 1H), 7.56 (dd, 1H)

(3) 1.81 g of phenyltrimethyl ammonium tribromide was added to a mixture comprising 1.0 g of 3,4-dimethoxyisobutyrophenone and 20 ml of tetrahydrofuran, followed by a reaction for two hours at room temperature. To the reaction mixture, diethyl ether was added, and the insoluble matter was filtered off. The filtrate was concentrated under reduced pressure to obtain oily α-bromo-3,4-dimethoxyisobutyrophenone.

(4) 0.62 g of sodium azide was added to a mixture comprising α-bromo-3,4-dimethoxyisobutyrophenone and 20 ml of dimethyl sulfoxide, followed by a reaction for 1.5 hours at 50° C. The reaction mixture was put into water and extracted with ethyl acetate, followed by washing with water. The organic layer was dried over anhydrous magnesium sulfate and then concentrated under reduced pressure. The residue was purified by silica gel column chromatography (developing solvent: ethyl acetate/n-hexane=1/4) to obtain 1.1 g of oily α-azide-3,4-dimethoxyisobutyrophenone. The NMR spectrum data of this product is as follows.

$^1$H-NMR δppm (Solvent: CDCl$_3$/400 MHz)

1.56 (s, 6H), 3.91 (s, 3H), 3.93 (s, 3H), 6.86 (d, 1H), 7.62 (d, 1H), 7.94 (dd, 1H)

(5) A mixture comprising 0.25 g of α-azide-3,4-dimethoxyisobutyrophenone, 15 ml of methanol and 13 mg of 5% palladium carbon, was reacted for 3 hours at room temperature in a hydrogen atmosphere. The reaction mixture was filtered through celite, and the filtrate was concentrated under reduced pressure to obtain 0.2 g of oily α-amino-3,4-dimethoxyisobutyrophenone.

(6) 0.11 g of triethylamine was added to a mixture comprising 0.2 g of α-amino-3,4-dimethoxyisobutyrophenone and 12 ml of 1,2-dichloroethane, and a mixture comprising 0.14 g of 3-methyl-2-thiophenecarbonylchloride and 2 ml of 1,2-dichloroethane, was dropwise added thereto under cooling with ice. After completion of the dropwise addition, the mixture was reacted for 1.5 hours at room temperature. The reaction mixture was extracted with methylene chloride, followed by washing with water. The organic layer was dried over anhydrous sodium sulfate and then concentrated under reduced pressure. The residue was purified by silica gel column chromatography (developing solvent: ethyl acetate/n-hexane=3/2) to obtain 0.1 g of the desired product having a melting point of from 138 to 140° C. The NMR spectrum data of this product is as follows.

$^1$H-NMR δppm (Solvent: CDCl$_3$/300 MHz)

1.82 (s, 6H), 2.44 (s, 3H), 3.89 (s, 6H), 6.80 (d, 1H), 6.85 (d, 1H), 6.88 (s, 1H), 7.23 (d, 1H), 7.63 (d, 1H), 7.75 (dd, 1H)

Now, typical examples of the acid amide derivative of the formula (I), (I-α) or a salt thereof will be given in Tables 1 to 9. These compounds can be prepared in accordance with the above Preparation Examples or by the above-described various processes.

In the Tables, No. represents compound No., Me methyl, Et ethyl, Pr(i) isopropyl, P(n) n-propyl, Bu(t) tert-butyl, Bu(n) n-butyl, Bu(sec) sec-butyl, CO carbonyl, CO$_2$ carboxyl, and Ph phenyl. Further, in the Tables, Ph (4-Cl) represents phenyl having a chlorine atom substituted at the 4-position, and Ph(3,4-Cl$_2$) represents a phenyl having chlorine atoms substituted at the 3- and 4-positions. The same applies to other expressions. Further, abbreviations D1 to D7 and B1 to B117 used in the Tables represent the following substituents, respectively.

D1:

D2:

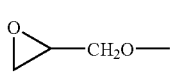

D3:

D4:

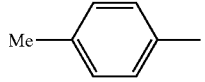

D5:

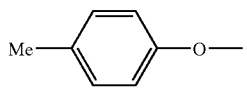

D6:

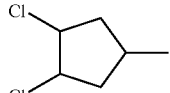

D7:

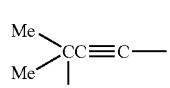

B1:

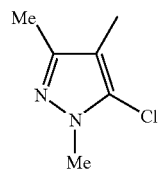

B2:

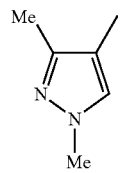

B3:

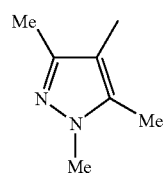

B4:

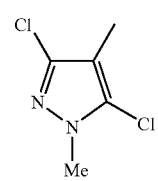

B5:

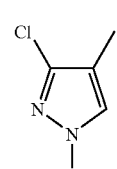

B6:

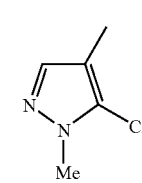

B7:

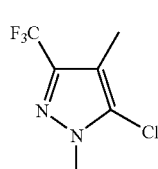

B8:

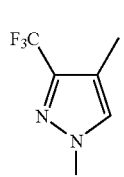

-continued
B9: 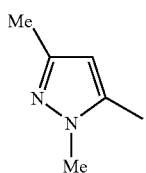
B10: 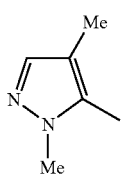
B11: 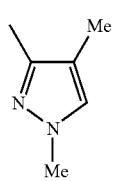
B12: 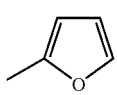
B13: 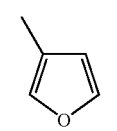
B14: 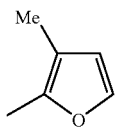
B15: 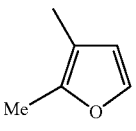
B16: 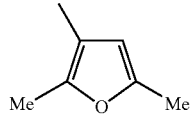
B17: 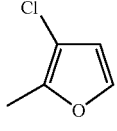
B18: 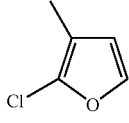
-continued
B19: 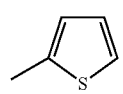
B20: 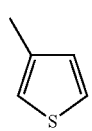
B21: 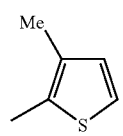
B22: 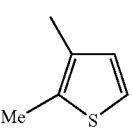
B23: 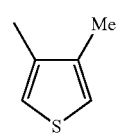
B24: 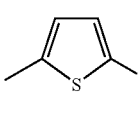
B25: 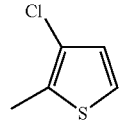
B26: 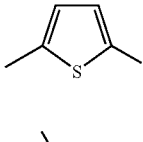
B27: 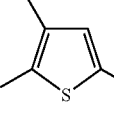
B28: 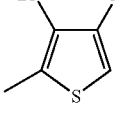
B29: 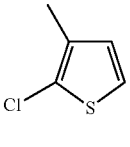

-continued
B30: 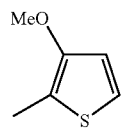
B31: 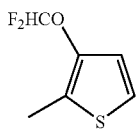
B32: 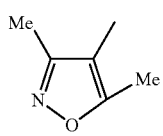
B33: 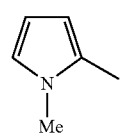
B34: 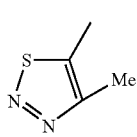
B35: 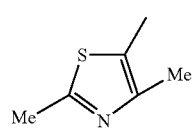
B36: 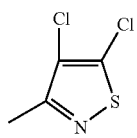
B37: 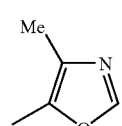
B38: 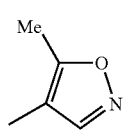
B39: 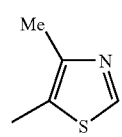
-continued
B40: 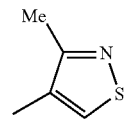
B41: 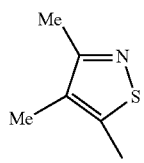
B42: 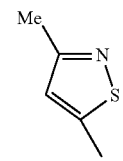
B43: 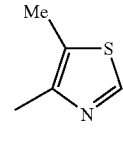
B44: 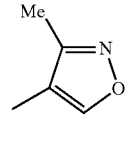
B45: 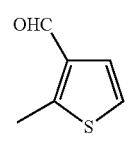
B46: 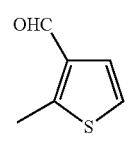
B47: 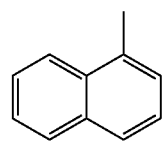
B48: 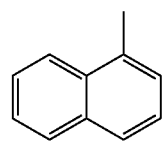

B49: 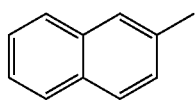
B50: 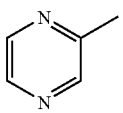
B51: 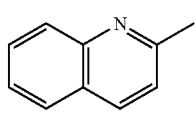
B52: 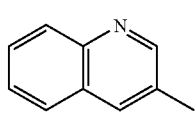
B53: 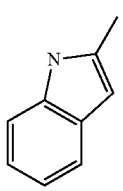
B54: 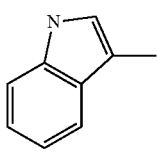
B55: 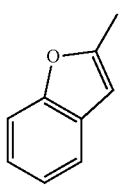
B56: 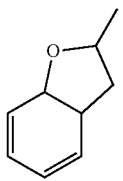
B57: 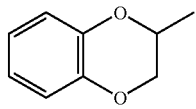
B58: 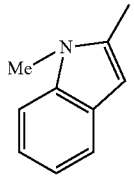
B59: 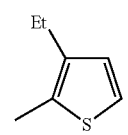
B60: 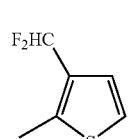
B61: 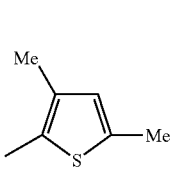
B62: 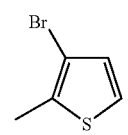
B63: 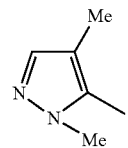
B64: 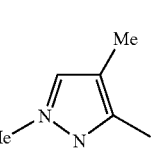
B65: 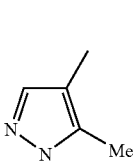
B66: 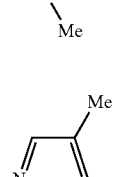
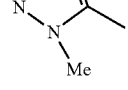

B67: 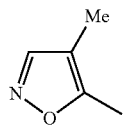
B68: 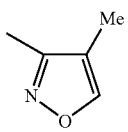
B69: 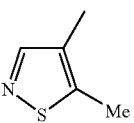
B70: 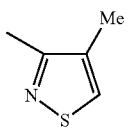
B71: 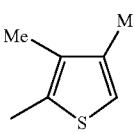
B72: 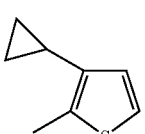
B73: 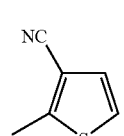
B74: 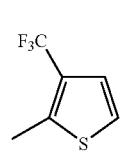
B75: 
B76: 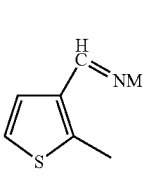
B77: 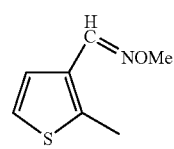
B78: 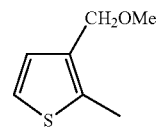
B79: 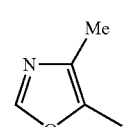
B80: 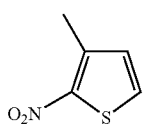
B81: 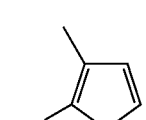
B82: 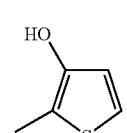
B83: 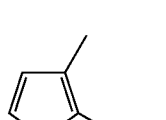
B84: 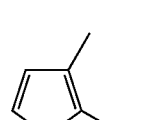
B85: 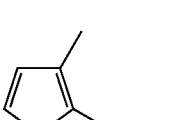
B86: 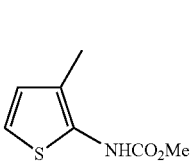

B87: 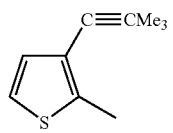
B88: 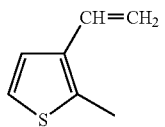
B89: 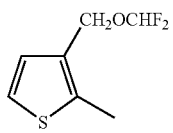
B90: 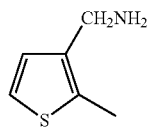
B91: 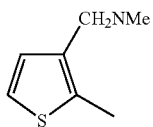
B92: 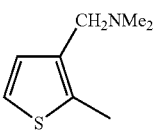
B93: 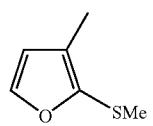
B94: 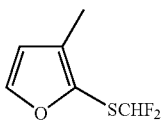
B95: 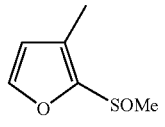
B96: 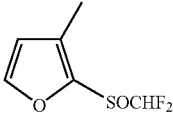
B97: 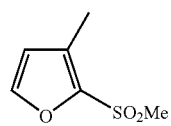
B98: 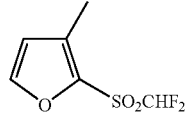
B99: 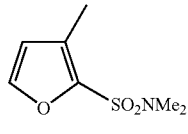
B100: 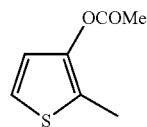
B101: 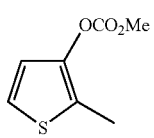
B102: 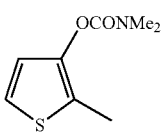
B103: 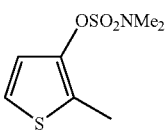
B104: 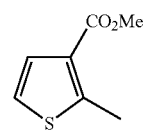
B105: 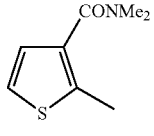
B106: 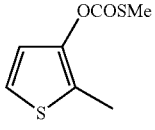

B107:
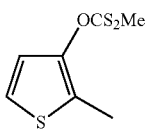
B108:
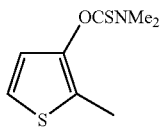
B109:
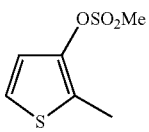
B110:
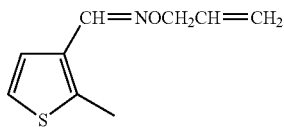
B111:
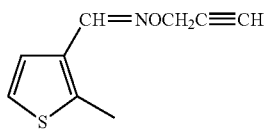
B112:
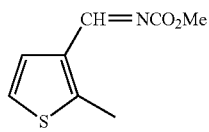
B113:
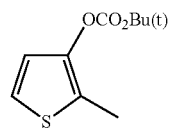
B114:
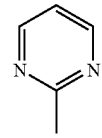
B115:
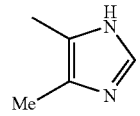
B116:
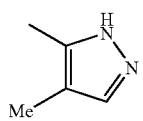
B117:
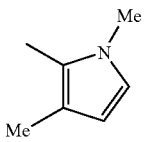
TABLE 1
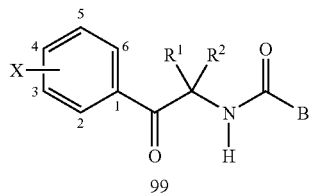
| No. | $R^1$ | $R^2$ | X | B | Physical properties (mp ° C.) |
|---|---|---|---|---|---|
| 1-1 | Me | Me | 2-Me-4-F | B1 | 132-134 |
| 1-2 | Me | Me | 2-Me-4-F | B5 | |
| 1-3 | Me | Me | 2-Me-4-F | B8 | |
| 1-4 | Me | Me | 2-Me-4-Cl | B1 | 141-143 |
| 1-5 | Me | Me | 2-Me-4-Cl | B5 | |
| 1-6 | Me | Me | 2-Me-4-Cl | B21 | 96-100 |
| 1-7 | Me | Me | 2-Me-4-Br | B16 | 138-140 |
| 1-8 | Me | Me | 2-Me-4-Br | B8 | |
| 1-9 | Me | Me | 2-Me-4-Br | B21 | 108-110 |
| 1-10 | Me | Me | 4-Cl | B1 | 186-188 |
| 1-11 | Me | Me | 4-Cl | B16 | 184-186 |
| 1-12 | Me | Me | H | B7 | 168-170 |
| 1-13 | Me | Me | 3-Cl-4-Cl | B1 | 188-189 |
| 1-14 | Me | Me | 3-Cl-4-Cl | B16 | 170-173 |
| 1-15 | Me | Me | 3-Cl-4-Cl | B7 | 182-183 |

TABLE 1-continued

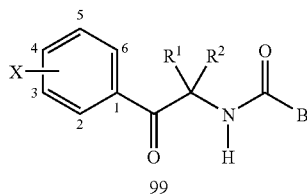

| No. | R¹ | R² | X | B | Physical properties (mp ° C.) |
|---|---|---|---|---|---|
| 1-16 | Me | Me | 3-Cl | B1 | 112-113 |
| 1-17 | Me | Me | 3-Cl | B16 | 150-151 |
| 1-18 | Me | Me | 3-Cl-4-Cl | B2 | 200-201 |
| 1-19 | Me | Me | 4-Br | B21 | 174 |
| 1-20 | Me | Me | 3-Cl-4-Cl | B21 | 141 |
| 1-21 | Me | Me | 3-Cl-4-Cl | B25 | Amorphous |
| 1-22 | Me | Me | 3-Cl-4-Cl | B14 | 137 |
| 1-23 | | | Sodium salt of No. 1-22 | | |
| 1-24 | Me | Me | 3-Cl-4-Cl | B24 | Solid |
| 1-25 | Me | Me | 3-Cl-4-Cl | B26 | 229 |
| 1-26 | Me | Me | 3-Br | B25 | 149 |
| 1-27 | Me | Me | 3-Br | B21 | 119 |
| 1-28 | Me | Me | 3-Me | B21 | Oil |
| 1-29 | Me | Me | 3-CF₃ | B21 | Amorphous |
| 1-30 | Me | Me | 3-OMe | B21 | 128 |
| 1-31 | Me | Me | 3-OCHF₂ | B21 | 110 |
| 1-32 | Me | Me | 4-Cl | B21 | 175 |
| 1-33 | Me | Me | 3-Cl-4-Cl | B9 | 126-130 |
| 1-34 | Me | Me | H | B1 | 103-105 |
| 1-35 | Me | Me | 4-Br | B19 | 235-240 |
| 1-36 | Me | Me | 4-Br | B16 | 183-185 |
| 1-37 | Me | Me | 4-Br | B20 | 245-247 |
| 1-38 | Me | Me | 3-Cl | B2 | 141-142 |
| 1-39 | Me | Me | 4-Cl | B2 | 140-141 |
| 1-40 | Me | Me | 3-Cl-4-Cl | B12 | 225-227 |
| 1-41 | Me | Me | 3-Cl-4-Cl | B5 | 171-172 |
| 1-42 | Me | Me | 3-F-4-F | B1 | 134-136 |
| 1-43 | Me | Me | 3-F-4-F | B16 | 150-152 |
| 1-44 | Me | Me | 2-Cl | B1 | 144-145 |
| 1-45 | Me | Me | 2-Cl | B16 | 130-132 |
| 1-46 | Me | Me | 3-Cl-4-Cl | B6 | Solid |
| 1-47 | Me | Me | 3-Cl-4-Cl | B4 | 150-152 |
| 1-48 | Me | Me | 3-Cl-4-Cl | B27 | 140-141 |
| 1-49 | Me | Me | 3-Cl-4-Cl | B3 | 141-146 |
| 1-50 | Me | Me | 3-Cl-4-Cl | B10 | |
| 1-51 | Me | Me | 3-Cl-4-Cl | B11 | |
| 1-52 | Me | Me | 4-Br | B1 | 183-185 |
| 1-53 | Me | Me | 3-Cl-5-Cl | B16 | 168-170 |
| 1-54 | Me | Me | 3-Cl-5-Cl | B1 | 152-153 |
| 1-55 | Me | Me | 3-Br | B16 | 143-145 |
| 1-56 | Me | Me | 3-Br | B1 | 151-152 |
| 1-57 | Me | Me | 3-Cl-4-Cl | B15 | 175-178 |
| 1-58 | Me | Me | 3-Cl-4-Cl | B17 | |
| 1-59 | Me | Me | 3-Cl-4-Cl | B18 | |
| 1-60 | Me | Me | 2-Cl-4-Cl | B16 | 165-167 |
| 1-61 | Me | Me | 2-Cl-4-Cl | B1 | 170-171 |
| 1-62 | Me | Me | 3-Me | B16 | 133-135 |
| 1-63 | Me | Me | 3-Me | B1 | 145-146 |
| 1-64 | Me | Me | 3-CF₃ | B16 | 125-127 |
| 1-65 | Me | Me | 3-CF₃ | B1 | 120-121 |
| 1-66 | Me | Me | 3-Cl | B21 | 128-130 |
| 1-67 | Me | Me | 3-Cl | B25 | 161-162 |
| 1-68 | Me | Me | 3-Cl-4-Cl | B29 | |
| 1-69 | Me | Me | 3-Cl-4-Cl | B30 | 93-96 |
| 1-70 | Me | Et | 3-Cl-4-Cl | B21 | |
| 1-71 | Me | Me | 3-OCHF₂ | B16 | 121-123 |
| 1-72 | Me | Me | 3-OCHF₂ | B1 | 138-139 |
| 1-73 | Me | Me | 3-OMe | B16 | 116-118 |
| 1-74 | Me | Me | 3-OMe | B1 | 118-120 |
| 1-75 | Me | Me | 3-Cl-4-Cl | B22 | 155-158 |
| 1-76 | Me | Me | 3-Cl-4-Cl | B31 | Oil |
| 1-77 | Me | Me | 3-Me-4-Me | B21 | 101-102 |
| 1-78 | Me | Me | 3-Cl-4-Cl | B23 | 220-222 |
| 1-79 | Me | Me | 3-Cl-4-Cl | B28 | 109-110 |
| 1-80 | Me | Me | 3-Cl-4-F | B21 | 124-126 |

TABLE 1-continued

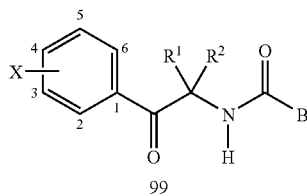

| No. | R¹ | R² | X | B | Physical properties (mp ° C.) |
|---|---|---|---|---|---|
| 1-81 | Me | Me | 3-Cl-4-F | B16 | |
| 1-82 | Me | Me | 3-Cl-4-F | B1 | |
| 1-83 | —(CH$_2$)$_5$— | | 4-Br | B7 | |
| 1-84 | —(CH$_2$)$_5$— | | 4-Br | B11 | |
| 1-85 | Me | Me | 3,4-(OCHF$_2$)$_2$ | B1 | |
| 1-86 | Me | Me | 3,4-(OCHF$_2$)$_2$ | B21 | 147-150 |
| 1-87 | Me | Me | 4-OCF$_3$ | B1 | |
| 1-88 | Me | Me | 3-OCF$_3$ | B21 | |
| 1-89 | Me | Me | 4-CF$_3$ | B1 | |
| 1-90 | Me | Me | 4-CF$_3$ | B21 | 113-115 |
| 1-91 | Me | Me | 4-CF$_3$ | B15 | |
| 1-92 | Me | Me | 4-CF$_3$ | B11 | |
| 1-93 | Me | Me | 3-Me-4-Me | B16 | 133-135 |
| 1-94 | Me | Me | 4-NO$_2$ | B16 | 179-180 |
| 1-95 | Me | Me | 4-NO$_2$ | B1 | 168-170 |
| 1-96 | Me | Me | 4-NO$_2$ | B21 | 135-137 |
| 1-97 | Me | Me | 3-Me-4-Me | B1 | 130-132 |
| 1-98 | Me | Me | 2-Me-4-OCHF$_2$ | B21 | 112-114 |
| 1-99 | Me | Me | 3-Cl-5-Cl | B21 | 137-140 |
| 1-100 | Me | Me | 3-Cl-4-Br | B21 | 120-121 |
| 1-101 | Me | Me | 3-Me-4-Cl | B21 | 108-112 |
| 1-102 | Me | Me | 3-Br-4-Cl | B21 | 117-120 |
| 1-103 | Me | Me | 3-Cl-4-Me | B21 | 115-118 |
| 1-104 | Me | Me | 2-Me-4-F | B21 | 107-109 |
| 1-105 | Me | Me | 4-Me | B21 | 152-154 |
| 1-106 | Me | Me | 4-OCF$_3$ | B21 | 116-120 |
| 1-107 | Me | Me | 3-Br-4-OCF$_3$ | B21 | 107-111 |
| 1-108 | Me | Me | 3-CF$_3$-4-Cl | B21 | 133-135 |
| 1-109 | Me | Me | 3-Cl-4-Br | B1 | 105-109 |
| 1-110 | Me | Me | 3-Cl-4-Cl | B19 | 192-195 |
| 1-111 | Me | Me | 4-OCH$_2$CF$_3$ | B21 | 134-138 |
| 1-112 | Me | Me | 4-OCHF$_2$ | B21 | 118-120 |
| 1-113 | Me | Me | 3-OMe-4-Cl | B21 | 154-159 |
| 1-114 | Me | Me | 3-Me-4-OCF$_3$ | B21 | 116-118 |
| 1-115 | Me | Me | 3-Cl-4-Me-5-Me | B21 | 107-114 |
| 1-116 | Me | Me | 2-Cl-3-Cl-4-Cl | B1 | 133-137 |
| 1-117 | Me | Me | 2-Me-3-Cl-4-Cl | B1 | 94-98 |
| 1-118 | Me | Me | 2-Cl-3-Cl-4-Cl | B21 | 112-115 |
| 1-119 | Me | Me | 2-Me-3-Cl-4-Cl | B21 | 90-95 |
| 1-120 | Me | Me | 2-Me-3-Me-4-Cl | B21 | Oil |
| 1-121 | Me | Me | 2-Cl-3-Me-4-Me | B21 | Oil |
| 1-122 | Me | Me | 3-Cl-4-Cl | B8 | 200-202 |
| 1-123 | Me | H | 4-Cl | B16 | Oil |
| 1-124 | Me | Me | 4-Br | B39 | 126-129 |
| 1-125 | Me | Me | 4-Bu(t) | B21 | 130-134 |
| 1-126 | Me | Me | 4-Bu(t) | B1 | 161-165 |
| 1-127 | Me | Me | 3-Me-4-Cl | B21 | 108-112 |
| 1-128 | Me | Me | 3-Cl-4-Cl | B37 | 157-159 |
| 1-129 | Me | Me | 3-Cl-4-Cl | B43 | 120-125 |
| 1-130 | Me | Me | 3-Cl-4-Cl | B44 | 165-170 |
| 1-131 | Me | Me | 4-(2-thienyl) | B21 | 119.2 |
| 1-132 | Me | Me | 4-(5-Me-2-thienyl) | B21 | 176.8 |
| 1-133 | Me | Me | 4-(2-furyl) | B21 | >300 |
| 1-134 | Me | Me | 4-(3-thienyl) | B21 | >300 |
| 1-135 | Me | Me | 4-(5-Cl-2-thienyl) | B21 | 153.5 |
| 1-136 | Me | Me | 4-(2-Me-3-thienyl) | B21 | Viscous |
| 1-137 | Me | Me | 4-(5-COMe-2-thienyl) | B21 | 199.2 |
| 1-138 | Me | Me | 3-(2-thienyl) | B21 | 134.2 |
| 1-139 | Me | Me | 3-(3-thienyl) | B21 | >300 |
| 1-140 | Me | Me | 3-(5-COMe-2-thienyl) | B21 | Oil |
| 1-141 | Me | Me | 3-(5-Cl-2-thienyl) | B21 | 141.7 |
| 1-142 | Me | Me | 3-(5-Me-2-thienyl) | B21 | 137.8 |
| 1-143 | Me | Me | 3-(4-Me-3-thienyl) | B21 | Amorphous |
| 1-144 | Me | Me | 3-(2-furyl) | B21 | Solid |
| 1-145 | Me | Me | 3-Cl-4-Cl | B32 | 135-137 |

TABLE 1-continued

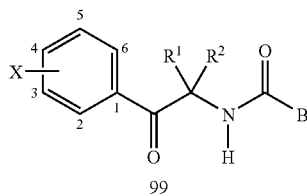

| No. | R¹ | R² | X | B | Physical properties (mp ° C.) |
|---|---|---|---|---|---|
| 1-146 | Me | Me | 3-Cl-4-Cl | B33 | 164 |
| 1-147 | Me | Me | 3-Cl-4-Cl | B34 | 153-154 |
| 1-148 | Me | Me | 3-Cl-4-Cl | B35 | Solid |
| 1-149 | Me | Me | 3-Cl-4-Cl | B36 | Solid |
| 1-150 | Me | Me | 3-Cl-4-Cl | B39 | 142-145 |
| 1-151 | Me | Me | 3-Cl-4-Cl | B40 | 145-146 |
| 1-152 | Me | Me | 3-Cl-4-Cl | B79 | 140-142 |
| 1-153 | Me | Me | 3-Cl-4-Cl | B38 | 165-166 |
| 1-154 | Me | Me | 3-Cl-4-Cl | B41 | 136-140 |
| 1-155 | Me | Me | 3-Cl-4-Cl | B42 | 175-178 |
| 1-156 | Me | Me | 3-Cl-4-Cl | B45 | 175-177 |
| 1-157 | Me | Me | 3-Cl-4-Cl | B46 | Oil |
| 1-158 | Me | Me | 4-(5-CF₃-pyridin-2-yloxy) | B1 | 127-128 |
| 1-159 | Me | Me | 4-(5-CF₃-pyridin-2-yloxy) | B21 | 138-140 |
| 1-160 | Me | Me | 2-Me-4-OMe | B21 | 99-101 |
| 1-161 | Me | Me | 2-Me-4-OEt | B21 | 85-88 |
| 1-162 | Me | Me | 2-Me-4-CF₃ | B21 | 110-113 |
| 1-163 | Me | Me | 2-Me-4-Me | B21 | 102-105 |
| 1-164 | Me | Me | 2-Me | B21 | 79-82 |
| 1-165 | Me | Me | 2-Me-3-Cl | B21 | 109-111 |
| 1-166 | Me | Me | 2-Br-4-CF₃ | B21 | 90-92 |
| 1-167 | Me | Me | 3-Br-4-Br | B21 | 127-130 |
| 1-168 | Me | Me | 3-Me-4-OCHF₂ | B21 | 100-106 |
| 1-169 | Me | Me | 4-[D3] | B21 | 107-109 |
| 1-170 | Me | Me | 3-Cl-4-Cl | B59 | 139-145 |
| 1-171 | Me | Me | 3-Cl-4-Cl | B60 | 139-141 |
| 1-172 | Me | Me | 3-Cl-4-Cl | B61 | 140-142 |
| 1-173 | H | H | 4-Cl | B21 | 119-121 |
| 1-174 | Me | Me | 2-Me-4-OPr | B21 | 97-100 |
| 1-175 | Me | Me | 3-Cl-4-Cl | B62 | 89-92 |
| 1-176 | Me | Me | 3-Me-4-OMe | B21 | 123-125 |
| 1-177 | Me | Me | 3-Cl-4-OMe | B21 | 161-164 |
| 1-178 | Me | Me | 2-Me-3-Me-4-OMe | B21 | 88-90 |
| 1-179 | Me | Me | 2-Me-3-Me-4-OCHF₂ | B21 | Oil |
| 1-180 | Me | Me | 4-OMe | B21 | 139-141 |
| 1-181 | Me | Me | 2-Me-4-OCOPr(i) | B21 | Amorphous |
| 1-182 | Me | Me | 2-Me-4-OH | B21 | 204-208 |
| 1-183 | Me | Me | 2-Me-4-OSO₂Me | B21 | 81-84 |
| 1-184 | Me | Me | 2-OMe | B21 | Oil |
| 1-185 | Me | Me | 2-Me-3-OMe | B21 | 128-129 |
| 1-186 | Me | Me | 2-Me-4-OBu(n) | B21 | 69-71 |
| 1-187 | Me | Me | 2-Me-4-OCH₂CF₃ | B21 | Oil |
| 1-188 | Me | Me | 2-Me-4-OCH₂CH₂OMe | B21 | 73-75 |
| 1-189 | Me | H | 4-Cl | B21 | Oil |
| 1-190 | Me | Me | 2-Me-4-OPr(i) | B21 | 96-98 |
| 1-191 | Me | Me | 4-Br | B48 | |
| 1-192 | Me | Me | 4-Br | B49 | |
| 1-193 | Me | Me | 4-Br | B50 | 122-125 |
| 1-194 | Me | Me | 4-Br | B51 | |
| 1-195 | Me | Me | 4-Br | B52 | 192-195 |
| 1-196 | Me | Me | 4-Br | B53 | |
| 1-197 | Me | Me | 4-Br | B54 | |
| 1-198 | Me | Me | 4-Br | B13 | |
| 1-199 | Me | Me | 4-Br | B12 | |
| 1-200 | Me | Me | 4-Br | B63 | 132-134 |
| 1-201 | Me | Me | 4-Br | B55 | 164-166 |
| 1-202 | Me | Me | 4-Br | B56 | 145-147 |
| 1-203 | Me | Me | 4-Br | B57 | 45-47 |
| 1-204 | Me | Me | 4-Br | B57 | 50-58 |
| 1-205 | Me | Me | 3-F-4-Cl | B21 | 119-122 |
| 1-206 | Me | Me | 2-Me-4-Et | B21 | 77-81 |
| 1-207 | Et | H | 4-Cl | B21 | 114-117 |
| 1-208 | Me | Me | 2-Cl-4-Cl | B21 | 103-104 |
| 1-209 | Me | Me | 3-OCHF₂-4-Cl | B21 | 106-110 |
| 1-210 | Me | Me | 3-Cl-4-OCHF₂ | B21 | 137-139 |

TABLE 1-continued

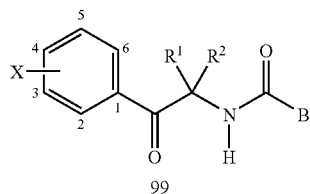

| No. | R¹ | R² | X | B | Physical properties (mp ° C.) |
|---|---|---|---|---|---|
| 1-211 | Me | Me | 3-Cl-4-Cl | B63 | |
| 1-212 | Me | Me | 3-Cl-4-Cl | B64 | |
| 1-213 | Me | Me | 3-Cl-4-Cl | B65 | |
| 1-214 | Me | Me | 3-Cl-4-Cl | B66 | |
| 1-215 | Me | Me | 3-Cl-4-Cl | B67 | |
| 1-216 | Me | Me | 3-Cl-4-Cl | B68 | |
| 1-217 | Me | Me | 3-Cl-4-Cl | B69 | |
| 1-218 | Me | Me | 3-Cl-4-Cl | B70 | |
| 1-219 | Me | Me | 3-Cl-4-Cl | B71 | 122-124 |
| 1-220 | Me | Me | 3-Cl-4-Cl | B72 | |
| 1-221 | Me | Me | 3-Cl-4-Cl | B73 | |
| 1-222 | Me | Me | 3-Cl-4-Cl | B74 | |
| 1-223 | Me | Me | 3-Cl-4-Cl | B75 | |
| 1-224 | Me | Me | 3-Cl-4-Cl | B76 | |
| 1-225 | Me | Me | 3-Cl-4-Cl | B77 | |
| 1-226 | Me | Me | 3-Cl-4-Cl | B78 | |
| 1-227 | Me | Me | 2-Me-4-O—[D3] | B21 | |
| 1-228 | Me | Me | 2-Me-4-CH$_2$NMe$_2$ | B21 | |
| 1-229 | Me | Me | 2-Me-4-CH$_2$OMe | B21 | |
| 1-230 | Me | Me | 2-Me-4-CH$_2$SMe | B21 | |
| 1-231 | Me | Me | 2-Me-5-OMe | B21 | Oil |
| 1-232 | Me | Me | 2-Me-5-Cl | B21 | |
| 1-233 | Me | Me | 2-Me-6-OMe | B21 | |
| 1-234 | Me | Me | 2-Me-6-Me | B21 | |
| 1-235 | Me | Me | 2-Me-4-OMe-6-Me | B21 | |
| 1-236 | Me | Me | 2-Me-4-Br | B21 | |
| 1-237 | Me | Me | 2-Me-4-OCF$_2$CHF$_2$ | B21 | |
| 1-238 | Me | Me | 2-Me-4-OCH$_2$CF$_2$CF$_3$ | B21 | |
| 1-239 | Me | Me | 2-Me-4-OCF$_2$CHFCF$_3$ | B21 | |
| 1-240 | Me | Me | 2-Et-4-OMe | B21 | |
| 1-241 | Me | Me | 2-CF$_3$-4-OMe | B21 | |
| 1-242 | Me | Me | 2-CF$_3$-4-Cl | B21 | |
| 1-243 | Me | Me | 3-Me-4-Br | B21 | |
| 1-244 | Me | Me | 3-Br-4-Me | B21 | 118-120 |
| 1-245 | Me | Me | 2-Me-4-OCH$_2$CN | B21 | |
| 1-246 | Me | Me | 2-Me-4-NHCH$_2$CN | B21 | |
| 1-247 | Me | Me | 2-Me-4-SCH$_2$CN | B21 | |
| 1-248 | Me | Me | 2-Me-4-OCH$_2$—[D3] | B21 | |
| 1-249 | Me | Me | 2-Me-4-NHCH$_2$—[D3] | B21 | |
| 1-250 | Me | Me | 2-Me-4-SCH$_2$—[D3] | B21 | |
| 1-251 | Me | Me | 2-Me-4-SMe | B21 | |
| 1-252 | Me | Me | 2-Me-4-SOMe | B21 | |
| 1-253 | Me | Me | 2-Me-4-SO$_2$Me | B21 | |
| 1-254 | Me | Me | 2-Me-4-CHO | B21 | |
| 1-255 | Me | Me | 2-Me-4-OCF$_3$ | B21 | |
| 1-256 | Me | Me | 2-Me-4-CHF$_2$ | B21 | |
| 1-257 | Me | Me | 2-Me-4-CH$_2$—[D3] | B21 | |
| 1-258 | Me | Me | 2-Me-4-[D3] | B21 | |
| 1-259 | Me | Me | 2-OCHF$_2$-4-Cl | B21 | |
| 1-260 | Me | Me | 2-F-4-Cl | B21 | |
| 1-261 | Me | Me | 2-OMe-4-Cl | B21 | |
| 1-262 | Me | Me | 2-Me-4-CH$_2$OCOMe | B21 | |
| 1-263 | Me | Me | 2-Me-4-CH$_2$OH | B21 | |
| 1-264 | Me | Me | 2-Me-4-CH$_2$Br | B21 | |
| 1-265 | Me | Me | 2-Me-4-I | B21 | |
| 1-266 | Me | Me | 2-Me-3-OEt | B21 | |
| 1-267 | Me | Me | 2-Me-4-cyclopentyloxy | B21 | |
| 1-268 | Me | Me | 2-Me-4-Ph | B21 | 97-102 |
| 1-269 | Me | Me | 2-Me-4-OPh | B21 | |
| 1-270 | Me | Me | 2-Me-4-OCOMe | B21 | Oil |
| 1-271 | Me | Me | 2-Me-4-C≡CCMe$_3$ | B21 | Amorphous |
| 1-272 | Me | Me | 2-Me-4-OCH$_2$C≡CH | B21 | |
| 1-273 | Me | Me | 2-Me-4-OBu(sec) | B21 | Viscous |
| 1-274 | Me | Me | 2-Me-4-OCH([D3])Me | B21 | |
| 1-275 | Me | Me | 2-Me-4-NH([D3])Me | B21 | |

TABLE 1-continued

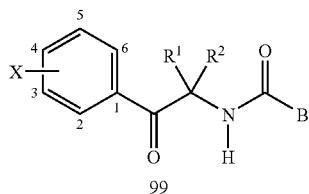

| No. | R¹ | R² | X | B | Physical properties (mp ° C.) |
|---|---|---|---|---|---|
| 1-276 | Me | Me | 2-Me-4-C≡CPh | B21 | Amorphous |
| 1-277 | Me | Me | 2-Me-4-OCF$_2$CHFOCF$_3$ | B21 | |
| 1-278 | Me | Me | 2-Me-4-CN | B21 | |
| 1-279 | Me | Me | 2-Me-4-CH$_2$C≡CCMe$_3$ | B21 | |
| 1-280 | Me | Me | 2-Me-4-C≡CMe | B21 | |
| 1-281 | Me | Me | 2-Me-4-C≡CH | B21 | |
| 1-282 | Me | Me | 2-Me-4-C≡CSiMe$_3$ | B21 | Viscous |
| 1-283 | Me | Me | 2-Me-4-[D1] | B21 | |
| 1-284 | Me | Me | 2-Me-4-[D2] | B21 | |
| 1-285 | Me | Me | 2-Me-4-CH$_2$C≡CI | B21 | |
| 1-286 | Me | Me | 2-Me-4-CH$_2$C≡CH | B21 | |
| 1-287 | Me | Me | 2-Me-4-CH=CF$_2$ | B21 | |
| 1-288 | Me | Me | 2-Me-4-CH$_2$CH=CF$_2$ | B21 | |
| 1-289 | Me | Me | 2-Me-4-OCH$_2$CH=CCl$_2$ | B21 | |
| 1-290 | Me | Me | 2-Me-4-CH$_2$CH$_2$CH=CF$_2$ | B21 | |
| 1-291 | Me | Me | 2-Me-4-(CH$_2$)$_5$CBrF$_2$ | B21 | |
| 1-292 | Me | Me | 2-Me-4-CH$_2$C≡CI | B1 | |
| 1-293 | Me | Et | 3-Cl-4-Cl | B1 | |
| 1-294 | Me | Et | 3-Me-4-Cl | B1 | |
| 1-295 | Me | Et | 2-Me-4-OMe | B1 | |
| 1-296 | Me | Et | 2-Me-4-OEt | B1 | |
| 1-297 | Me | Et | 2-Me-4-OPr(i) | B1 | |
| 1-298 | Me | Et | 3-Cl-4-Br | B1 | |
| 1-299 | Me | Et | 3-Br-4-Cl | B1 | |
| 1-300 | Me | Et | 3-F-4-Cl | B1 | |
| 1-301 | Me | Et | 3-Me-4-Br | B1 | |
| 1-302 | Et | Et | 3-Cl-4-Cl | B1 | |
| 1-303 | Et | Et | 3-Me-4-Cl | B1 | |
| 1-304 | Et | Et | 2-Me-4-OEt | B1 | |
| 1-305 | Et | Et | 2-Me-4-OPr(i) | B1 | |
| 1-306 | Me | Et | 3-Cl-4-Cl | B16 | |
| 1-307 | Me | Et | 3-Me-4-Cl | B16 | |
| 1-308 | Me | Et | 2-Me-4-OMe | B16 | |
| 1-309 | Me | Et | 2-Me-4-OEt | B16 | |
| 1-310 | Me | Et | 2-Me-4-OPr(i) | B16 | |
| 1-311 | Me | Et | 3-Cl-4-Br | B16 | |
| 1-312 | Me | Et | 3-Br-4-Cl | B16 | |
| 1-313 | Me | Et | 3-F-4-Cl | B16 | |
| 1-314 | Me | Et | 3-Me-4-Br | B16 | |
| 1-315 | Et | Et | 3-Cl-4-Cl | B16 | |
| 1-316 | Et | Et | 3-Me-4-Cl | B16 | |
| 1-317 | Et | Et | 2-Me-4-OEt | B16 | |
| 1-318 | Et | Et | 2-Me-4-OPr(i) | B16 | |
| 1-319 | Me | Et | 3-Me-4-Cl | B21 | |
| 1-320 | Me | Et | 2-Me-4-OMe | B21 | |
| 1-321 | Me | Et | 2-Me-4-OEt | B21 | |
| 1-322 | Me | Et | 2-Me-4-OPr(i) | B21 | |
| 1-323 | Me | Et | 3-Cl-4-Br | B21 | |
| 1-324 | Me | Et | 3-Br-4-Cl | B21 | |
| 1-325 | Me | Et | 3-F-4-Cl | B21 | |
| 1-326 | Me | Et | 3-Me-4-Br | B21 | |
| 1-327 | Et | Et | 3-Cl-4-Cl | B21 | |
| 1-328 | Et | Et | 3-Me-4-Cl | B21 | |
| 1-329 | Et | Et | 2-Me-4-OEt | B21 | |
| 1-330 | Et | Et | 2-Me-4-OPr(i) | B21 | |
| 1-331 | Me | Me | 3-Me-4-Cl | B71 | |
| 1-332 | Me | Me | 2-Me-4-OMe | B71 | |
| 1-333 | Me | Me | 2-Me-4-OEt | B71 | |
| 1-334 | Me | Me | 2-Me-4-OPr(i) | B71 | |
| 1-335 | Me | Me | 3-Cl-4-Br | B71 | |
| 1-336 | Me | Me | 3-Br-4-Cl | B71 | |
| 1-337 | Me | Me | 3-F-4-Cl | B71 | |
| 1-338 | Me | Me | 3-Me-4-Br | B71 | |
| 1-339 | Me | Me | 2-Me-4-[D4] | B21 | |
| 1-340 | Me | Me | 2-Me-4-[D5] | B21 | |

TABLE 1-continued

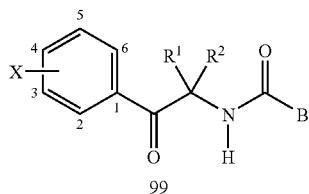

| No. | R¹ | R² | X | B | Physical properties (mp ° C.) |
|---|---|---|---|---|---|
| 1-341 | Me | D3 | 3-Cl-4-Cl | B16 | |
| 1-342 | Me | D3 | 3-Me-4-Cl | B16 | |
| 1-343 | Me | D3 | 2-Me-4-OMe | B16 | |
| 1-344 | Me | D3 | 2-Me-4-OEt | B16 | |
| 1-345 | Me | D3 | 2-Me-4-OPr(i) | B16 | |
| 1-346 | Me | D3 | 3-Cl-4-Br | B16 | |
| 1-347 | Me | D3 | 3-Br-4-Cl | B16 | |
| 1-348 | Me | D3 | 3-F-4-Cl | B16 | |
| 1-349 | Me | D3 | 3-Me-4-Br | B16 | |
| 1-350 | H | D3 | 3-Cl-4-Cl | B16 | |
| 1-351 | H | D3 | 3-Me-4-Cl | B16 | |
| 1-352 | H | D3 | 2-Me-4-OMe | B16 | |
| 1-353 | H | D3 | 2-Me-4-OEt | B16 | |
| 1-354 | H | D3 | 2-Me-4-OPr(i) | B16 | |
| 1-355 | Me | D3 | 3-Cl-4-Cl | B21 | |
| 1-356 | Me | D3 | 3-Me-4-Cl | B21 | |
| 1-357 | Me | D3 | 2-Me-4-OMe | B21 | |
| 1-358 | Me | D3 | 2-Me-4-OEt | B21 | |
| 1-359 | Me | D3 | 2-Me-4-OPr(i) | B21 | |
| 1-360 | Me | D3 | 3-Cl-4-Br | B21 | |
| 1-361 | Me | D3 | 3-Br-4-Cl | B21 | |
| 1-362 | Me | D3 | 3-F-4-Cl | B21 | |
| 1-363 | Me | D3 | 3-Me-4-Br | B21 | |
| 1-364 | H | D3 | 3-Cl-4-Cl | B21 | |
| 1-365 | H | D3 | 3-Me-4-Cl | B21 | |
| 1-366 | H | D3 | 2-Me-4-OMe | B21 | |
| 1-367 | H | D3 | 2-Me-4-OEt | B21 | |
| 1-368 | H | D3 | 2-Me-4-OPr(i) | B21 | |
| 1-369 | Me | CH₂F | 3-Cl-4-Cl | B21 | |
| 1-370 | Me | CH₂F | 3-Me-4-Cl | B21 | |
| 1-371 | Me | CH₂Cl | 2-Me-4-OMe | B21 | |
| 1-372 | Me | CH₂F | 2-Me-4-OEt | B21 | |
| 1-373 | Me | CH₂F | 2-Me-4-OPr(i) | B21 | |
| 1-374 | CH₂F | CH₂F | 2-Me-4-OEt | B21 | |
| 1-375 | CH₂F | CH₂F | 2-Me-4-OPr(i) | B21 | |
| 1-376 | Me | Me | 4-SMe | B16 | |
| 1-377 | Me | Me | 4-SOMe | B16 | |
| 1-378 | Me | Me | 4-SO₂Me | B16 | |
| 1-379 | Me | Me | 4-SO₂CF₃ | B16 | |
| 1-380 | Me | Me | 4-SO₂NMe₂ | B16 | |
| 1-381 | Me | Me | 4-CH₂CH=CH₂ | B16 | |
| 1-382 | Me | Me | 4-CH₂NHMe | B16 | |
| 1-383 | Me | Me | 2-Me-4-CH₂NHMe | B21 | |
| 1-384 | Me | Me | 2-Me-4-OCH₂CN | B21 | |
| 1-385 | Me | Me | 2-Me-4-NHCH₂CN | B21 | |
| 1-386 | Me | Me | 2-Me-4-SCH₂CN | B21 | |
| 1-387 | Me | Me | 4-OCH₂CH=CH₂ | B16 | |
| 1-388 | Me | Me | 4-SCH₂CH=CH₂ | B16 | |
| 1-389 | Me | Me | 4-OCH₂C≡CH | B16 | |
| 1-390 | Me | Me | 4-SCH₂C≡CH | B16 | |
| 1-391 | Me | Me | 4-OCH₂C≡Cl | B16 | |
| 1-392 | Me | Me | 4-SCH₂C≡Cl | B16 | |
| 1-393 | Me | Me | 2-Me-4-OCF₂CHFOMe | B21 | |
| 1-394 | Me | Me | 4-S—CH₂CH=CF₂ | B16 | |
| 1-395 | Me | Me | 4-SOCHF₂ | B16 | |
| 1-396 | Me | Me | 2-Me-4-CH₂OCHF₂ | B21 | |
| 1-397 | Me | Me | 2-Me-4-CH₂NH₂ | B21 | |
| 1-398 | Me | Me | 2-Me-4-SCHF₂ | B21 | |
| 1-399 | Me | Me | 2-Me-4-SOCHF₂ | B21 | |
| 1-400 | Me | Me | 2-Me-4-SO₂CHF₂ | B21 | |
| 1-401 | Me | Me | 2-Me-4-OCH₂CH₂SMe | B21 | |
| 1-402 | Me | Me | 2-Me-4-OCH₂CH₂NHMe | B21 | |
| 1-403 | Me | Me | 2-Me-4-OCH₂CH₂NMe₂ | B21 | |
| 1-404 | Me | Me | 2-Me-4-NH—[D3] | B21 | |
| 1-405 | Me | Me | 2-Me-4-S—[D3] | B21 | |

TABLE 1-continued

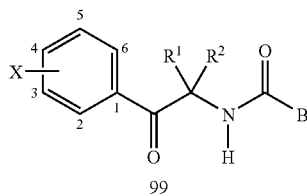

| No. | R¹ | R² | X | B | Physical properties (mp °C.) |
|---|---|---|---|---|---|
| 1-406 | Me | Me | 2-Me-4-OCH$_2$CH$_2$OCHF$_2$ | B71 | |
| 1-407 | Me | Me | 4-CH=NOCH$_2$CH=CH$_2$ | B1 | |
| 1-408 | Me | Me | 4-CH=NOCH$_2$C≡CH | B1 | |
| 1-409 | Me | Me | 4-CH=NCO$_2$Me | B1 | |
| 1-410 | Me | Me | 2-Me-4-CH=NMe | B21 | |
| 1-411 | Me | Me | 2-Me-4-CH=N—OMe | B21 | |
| 1-412 | Me | Me | 4-[D6] | B71 | |
| 1-413 | Me | Me | 2-Me-4-OCOCF$_3$ | B21 | |
| 1-414 | Me | Me | 2-Me-4-OCO$_2$Me | B16 | |
| 1-415 | Me | Me | 2-Me-4-OCONMe$_2$ | B16 | |
| 1-416 | Me | Me | 2-Me-4-OCOSPh | B16 | |
| 1-417 | Me | Me | 2-Me-4-OCSOMe | B14 | |
| 1-418 | Me | Me | 2-Me-4-OCS$_2$Me | B14 | |
| 1-419 | Me | Me | 2-Me-4-OCSNMe$_2$ | B14 | |
| 1-420 | Me | Me | 2-Me-4-OSCCl$_3$ | B14 | |
| 1-421 | Me | Me | 2-Me-4-OSO$_2$Me | B14 | |
| 1-422 | Me | Me | 2-Me-4-OSO$_2$CF$_3$ | B14 | |
| 1-423 | Me | Me | 2-Me-4-OSO$_2$Ph | B14 | |
| 1-424 | Me | Me | 2-Me-4-OSNMe$_2$ | B14 | |
| 1-425 | Me | Me | 2-Me-4-OSO$_2$NMe$_2$ | B14 | |
| 1-426 | Me | Me | 2-Me-4-NH$_2$ | B14 | |
| 1-427 | Me | Me | 2-Me-4-NH$_2$•HCl | B14 | |
| 1-428 | Me | Me | 2-Me-4-NHMe | B14 | |
| 1-429 | Me | Me | 2-Me-4-NMe$_2$ | B14 | |
| 1-430 | Me | Me | 2-Me-4-NHCOMe | B14 | |
| 1-431 | Me | Me | 2-Me-4-NHCOBu(t) | B14 | |
| 1-432 | Me | Me | 2-Me-4-NHCOCF$_3$ | B14 | |
| 1-433 | Me | Me | 2-Me-4-NHCO$_2$Me | B14 | |
| 1-434 | Me | Me | 2-Me-4-N(Me)CO$_2$Me | B14 | |
| 1-435 | Me | Me | 2-Me-4-NHCONMe$_2$ | B14 | |
| 1-436 | Me | Me | 2-Me-4-NHCOSMe | B14 | |
| 1-437 | Me | Me | 2-Me-4-NHCSOMe | B14 | |
| 1-438 | Me | Me | 2-Me-4-NHCS$_2$Me | B14 | |
| 1-439 | Me | Me | 2-Me-4-NHCSNMe$_2$ | B14 | |
| 1-440 | Me | Me | 2-Me-4-NHCS$_2$Ph | B14 | |
| 1-441 | Me | Me | 2-Me-4-NHSCCl$_3$ | B14 | |
| 1-442 | Me | Me | 2-Me-4-NHSOMe | B14 | |
| 1-443 | Me | Me | 2-Me-4-NHSO$_2$Me | B14 | |
| 1-444 | Me | Me | 2-Me-4-NHSO$_2$Ph | B14 | |
| 1-445 | Me | Me | 2-Me-4-NHCOPh | B14 | |
| 1-446 | Me | Me | 4-CO$_2$Me | B14 | |
| 1-447 | Me | Me | 4-CO$_2$Et | B14 | |
| 1-448 | Me | Me | 4-CO$_2$H | B14 | |
| 1-449 | Me | Me | 4-CONH$_2$ | B14 | |
| 1-450 | Me | Me | 4-CONMe$_2$ | B14 | |
| 1-451 | Me | Me | 4-CONHMe | B14 | |
| 1-452 | Me | Me | 2-Me-4-SCH$_2$CF$_3$ | B21 | |
| 1-453 | Me | Me | 2-Me-4-NHCH$_2$CF$_3$ | B21 | |
| 1-454 | Me | Me | 2-Me-4-SCHF$_2$ | B21 | |
| 1-455 | Me | Me | 2-Me-4-SO$_2$CH$_2$CF$_3$ | B21 | |
| 1-456 | Me | Me | 2-Me-4-OCN | B21 | |
| 1-457 | Me | Me | 2-Me-4-CH$_2$CO$_2$Me | B21 | |
| 1-458 | Me | Me | 2-Me-4-OPh | B21 | |
| 1-459 | Me | Me | 2-Me-4-Ph | B21 | |
| 1-460 | Me | Me | 2-Me-4-C≡CCO$_2$Me | B21 | |
| 1-461 | Me | Me | 2-Me-4-C≡CCO$_2$H | B21 | |
| 1-462 | Me | Me | 2-Me-4-C≡CCH$_2$OH | B21 | |
| 1-463 | Me | Me | 2-Me-4-C≡CCH$_2$Br | B21 | |
| 1-464 | Me | Me | 2-Me-4-C≡CCH$_2$NH$_2$•HCl | B21 | |
| 1-465 | Me | Me | 2-Me-4-[D7] | B21 | |
| 1-466 | Me | Me | 2-Me-4-C≡COEt | B21 | |
| 1-467 | Me | Me | 2-Me-4-C≡CCH$_2$OMe | B21 | |
| 1-468 | Me | Me | 2-Me-4-C≡C—[D4] | B21 | |
| 1-469 | Me | Me | 2-Me-4-OCH$_2$—[D4] | B21 | |
| 1-470 | Me | Me | 2-Me-4-[D5] | B14 | |

TABLE 1-continued

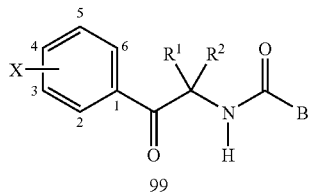

| No. | R¹ | R² | X | B | Physical properties (mp ° C.) |
|---|---|---|---|---|---|
| 1-471 | Me | Me | 2-Me-4-[D4] | B14 | |
| 1-472 | Me | Me | 2-Me-4-CH=CH—[D4] | B21 | |
| 1-473 | Me | Me | 2-Me-4-CH$_2$—[D4] | B21 | |
| 1-474 | Me | Me | 2-Me-4-OC≡C—[D4] | B21 | |
| 1-475 | Me | Me | 2-Me-4-OCH=CH—[D4] | B21 | |
| 1-476 | Me | Me | 4-Me | B62 | |
| 1-477 | Me | Me | 4-Me | B25 | |
| 1-478 | Me | Me | 3-Cl-4-Cl | B80 | |
| 1-479 | Me | Me | 3-Cl-4-Cl | B81 | |
| 1-480 | Me | Me | 3-Cl-4-Cl | B82 | |
| 1-481 | Me | Me | 3-Cl-4-Cl | B83 | |
| 1-482 | Me | Me | 3-Me-4-Cl | B84 | |
| 1-483 | Me | Me | 2-Me-4-OMe | B85 | |
| 1-484 | Me | Me | 2-Me-4-OEt | B86 | |
| 1-485 | Me | Me | 2-Me-4-OPr(i) | B87 | |
| 1-486 | Me | Me | 3-Cl-4-Br | B88 | |
| 1-487 | Me | Me | 3-Br-4-Cl | B89 | |
| 1-488 | Me | Me | 3-F-4-Cl | B90 | |
| 1-489 | Me | Me | 3-Me-4-Br | B91 | |
| 1-490 | Me | Me | 3-Cl-4-Cl | B92 | |
| 1-491 | Me | Me | 3-Me-4-Cl | B93 | |
| 1-492 | Me | Me | 2-Me-4-OMe | B94 | |
| 1-493 | Me | Me | 2-Me-4-OEt | B95 | |
| 1-494 | Me | Me | 2-Me-4-OPr(i) | B96 | |
| 1-495 | Me | Me | 3-Cl-4-Br | B97 | |
| 1-496 | Me | Me | 3-Br-4-Cl | B98 | |
| 1-497 | Me | Me | 3-F-4-Cl | B99 | |
| 1-498 | Me | Me | 3-Me-4-Br | B100 | |
| 1-499 | Me | Me | 3-Cl-4-Cl | B101 | |
| 1-500 | Me | Me | 3-Me-4-Cl | B102 | |
| 1-501 | Me | Me | 2-Me-4-OMe | B103 | |
| 1-502 | Me | Me | 2-Me-4-OEt | B104 | |
| 1-503 | Me | Me | 2-Me-4-OPr(i) | B105 | |
| 1-504 | Me | Me | 3-Cl-4-Br | B106 | |
| 1-505 | Me | Me | 3-Br-4-Cl | B107 | |
| 1-506 | Me | Me | 3-F-4-Cl | B108 | |
| 1-507 | Me | Me | 3-Me-4-Br | B109 | |
| 1-508 | Me | Me | 3-Cl-4-Cl | B110 | |
| 1-509 | Me | Me | 3-Me-4-Cl | B111 | |
| 1-510 | Me | Me | 2-Me-4-OMe | B112 | |
| 1-511 | Me | Me | 2-Me-4-OEt | B113 | |
| 1-512 | Me | Me | 2-Me-4-OPr(i) | B114 | |
| 1-513 | Me | Me | 3-Cl-4-Br | B115 | |
| 1-514 | Me | Me | 3-Br-4-Cl | B116 | |
| 1-515 | Me | Me | 3-F-4-Cl | B117 | |
| 1-516 | Me | Me | 2-Br-5-OMe | B21 | Oil |
| 1-517 | Me | Me | 2-Me-4-OCH(Me)OMe | B16 | |
| 1-518 | Me | Me | 4-CH$_2$Br | B25 | Viscous |
| 1-519 | Me | Me | 4-CH$_2$Br | B62 | 108-111 |
| 1-520 | Me | Me | 4-CH$_2$OMe | B25 | 97-102 |
| 1-521 | Me | Me | 4-CH$_2$NMe$_2$ | B25 | Viscous |
| 1-522 | Me | Me | 2-Me-4-OCH$_2$Ph | B14 | |
| 1-523 | Me | CH$_2$Cl | 3-F-4-Cl | B1 | |
| 1-524 | Me | CH$_2$Cl | 3-Me-4-Br | B14 | |
| 1-525 | Me | CH$_2$Cl | 3-Cl-4-Cl | B16 | |
| 1-526 | Me | CH=CH$_2$ | 3-Me-4-Cl | B21 | |
| 1-527 | Me | CH=CH$_2$ | 2-Me-4-OMe | B1 | |
| 1-528 | Me | CH=CH$_2$ | 2-Me-4-OEt | B14 | |
| 1-529 | Me | C≡CH | 2-Me-4-OPr(i) | B16 | |
| 1-530 | Me | C≡CH | 3-Cl-4-Br | B21 | |
| 1-531 | Me | C≡CH | 3-Br-4-Cl | B1 | |
| 1-532 | Me | CH$_2$OMe | 3-F-4-Cl | B14 | |
| 1-533 | Me | CH$_2$OMe | 3-Me-4-Br | B16 | |
| 1-534 | Me | CH$_2$OMe | 3-Cl-4-Cl | B21 | |
| 1-535 | Me | Me | 3-OMe-4-OMe | B21 | 138-140 |

TABLE 1-continued

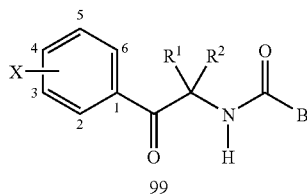

| No. | R¹ | R² | X | B | Physical properties (mp ° C.) |
|---|---|---|---|---|---|
| 1-536 | Me | Me | 2-Br | B21 | Viscous |
| 1-537 | Me | Me | 4-SPh | B1 | |
| 1-538 | Me | Me | 4-CH$_2$OMe | B62 | 74-76 |
| 1-539 | Me | Me | 4-CH$_2$NMe$_2$ | B62 | Viscous |
| 1-540 | Me | Me | 4-CH$_2$OMe | B21 | 117-119 |
| 1-541 | Me | Me | 4-CH$_2$SMe | B21 | |
| 1-542 | Me | Me | 4-CH$_2$NMe$_2$ | B21 | |
| 1-543 | Me | Me | 2-Me-4-Ph(4-Cl) | B21 | |
| 1-544 | Me | Me | 2-Me-4-Ph(4-Me) | B21 | |
| 1-545 | Me | Me | 2-Me-4-CH=CHCMe$_3$ | B16 | |
| 1-546 | Me | Me | 2-Me-4-Ph(4-CF$_3$) | B21 | |
| 1-547 | Me | Me | 2-Me-4-CH=CHPh | B14 | |
| 1-548 | Me | Me | 2-Me-4-CH$_2$SO$_2$Me | B21 | |
| 1-549 | Me | Me | 4-Me | B25 | 96-98 |
| 1-550 | Me | Me | 4-Me | B62 | 98-102 |
| 1-551 | Me | Me | 4-SCO$_2$Me | B1 | |
| 1-552 | Me | Me | 2-Me-4-CH$_2$CN | B16 | |
| 1-553 | Me | Me | 4-NHPh | B1 | |
| 1-554 | Me | Me | 2-Me-4-OBu(t) | B21 | |

TABLE 2

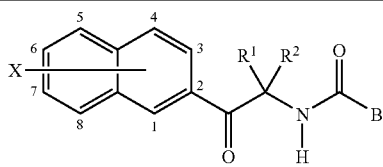

| No. | R¹ | R² | X | B | Physical properties (mp ° C.) |
|---|---|---|---|---|---|
| 2-1 | Me | Me | H | B1 | 145-147 |
| 2-2 | Me | Me | H | B16 | 159-161 |
| 2-3 | Me | Me | H | B7 | 152-154 |
| 2-4 | Me | Me | H | B2 | Solid |
| 2-5 | Me | Et | H | B1 | |
| 2-6 | Me | Et | H | B16 | |
| 2-7 | Me | Et | H | B21 | |
| 2-8 | —(CH$_2$)$_5$— | | H | B16 | |
| 2-9 | Me | Me | H | B12 | 225-226 |
| 2-10 | Me | Me | H | B5 | 159-160 |
| 2-11 | Me | Me | H | B8 | 196-198 |
| 2-12 | Me | Me | H | B13 | 195-197 |
| 2-13 | Me | Me | H | B15 | 158-160 |
| 2-14 | Me | Me | H | B21 | 163-164 |
| 2-15 | —(CH$_2$)$_5$— | | H | B21 | |
| 2-16 | Me | Et | H | B1 | |
| 2-17 | Me | Et | H | B5 | |
| 2-18 | Me | Et | H | B8 | |
| 2-19 | Me | Et | H | B11 | |
| 2-20 | Me | Et | H | B14 | |
| 2-21 | Me | Et | H | B15 | |
| 2-22 | Me | Et | H | B16 | |
| 2-23 | Me | Et | H | B21 | |
| 2-24 | Me | Me | 1-Me | B1 | |
| 2-25 | Me | Me | 3-Me | B5 | |
| 2-26 | Me | Me | 4-Me | B8 | |
| 2-27 | Me | Me | 5-Me | B14 | |
| 2-28 | Me | Me | 6-Me | B15 | |
| 2-29 | Me | Me | 7-Me | B16 | |

TABLE 2-continued

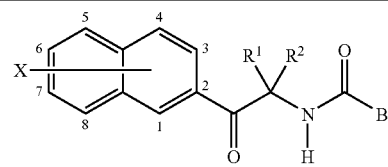

| No. | R¹ | R² | X | B | Physical properties (mp ° C.) |
|---|---|---|---|---|---|
| 2-30 | Me | Me | 8-Me | B21 | |
| 2-31 | Me | Me | H | B48 | |
| 2-32 | Me | Me | H | B49 | |
| 2-33 | Me | Me | H | B19 | |
| 2-34 | Me | Me | H | B20 | |
| 2-35 | Me | Me | H | B50 | |
| 2-36 | Me | Me | 1-Me | B21 | |
| 2-37 | Me | Me | 1-Me | B16 | |

TABLE 3

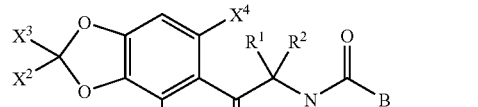

| No. | R¹ | R² | X¹ | X² | X³ | X⁴ | B | Physical properties (mp ° C.) |
|---|---|---|---|---|---|---|---|---|
| 3-1 | Me | Me | H | H | H | H | B1 | 127-128 |
| 3-2 | Me | Me | H | H | H | H | B16 | 130-132 |
| 3-3 | Me | Me | H | H | H | H | B21 | 155-158 |

TABLE 3-continued

| No. | R¹ | R² | X¹ | X² | X³ | X⁴ | B | Physical properties (mp ° C.) |
|---|---|---|---|---|---|---|---|---|
| 3-4 | Me | Me | H | F | F | H | B1 | 124-126 |
| 3-5 | Me | Me | H | F | F | H | B16 | |
| 3-6 | Me | Me | H | F | F | H | B21 | 116-118 |
| 3-7 | Me | Me | Me | H | H | H | B1 | |
| 3-8 | Me | Me | Me | H | H | H | B16 | |
| 3-9 | Me | Me | Me | H | H | H | B21 | 98-102 |
| 3-10 | Me | Me | Me | F | F | H | B1 | 99-107 |
| 3-11 | Me | Me | Me | F | F | H | B16 | |
| 3-12 | Me | Me | Me | F | F | H | B21 | 145-148 |
| 3-13 | Me | Me | Cl | H | H | H | B1 | |
| 3-14 | Me | Me | Cl | H | H | H | B16 | |
| 3-15 | Me | Me | Cl | H | H | H | B21 | |
| 3-16 | Me | Me | Cl | F | F | H | B1 | |
| 3-17 | Me | Me | Cl | F | F | H | B16 | |
| 3-18 | Me | Me | Cl | F | F | H | B21 | |
| 3-19 | Me | Me | Me | F | F | H | B8 | 142-145 |
| 3-20 | Me | Me | Me | F | F | H | B5 | 104-108 |
| 3-21 | —(CH₂)₅— | | H | F | F | H | B21 | |
| 3-22 | —(CH₂)₅— | | Me | F | F | H | B1 | |
| 3-23 | Me | Me | H | F | F | H | B5 | 158-160 |
| 3-24 | Me | Me | Me | F | F | H | B47 | 97-99 |
| 3-25 | Me | Me | H | F | F | Me | B21 | 85-90 |
| 3-26 | Me | Me | H | H | H | Me | B21 | 111-114 |
| 3-27 | Me | Me | Me | Me | Me | H | B21 | |
| 3-28 | Me | Me | Me | Me | H | H | B21 | |
| 3-29 | Me | Me | Me | Et | H | H | B21 | |
| 3-30 | Me | Me | Me | D3 | H | H | B21 | |

TABLE 4

| No. | R¹ | R² | X¹ | X² | X³ | B | Physical properties (mp ° C.) |
|---|---|---|---|---|---|---|---|
| 4-1 | Me | Me | H | H | H | B1 | |
| 4-2 | Me | Me | H | H | H | B5 | |
| 4-3 | Me | Me | H | H | H | B8 | |
| 4-4 | Me | Me | H | H | H | B16 | |
| 4-5 | Me | Me | H | H | H | B21 | |
| 4-6 | Me | Me | H | F | F | B1 | |
| 4-7 | Me | Me | H | F | F | B5 | |
| 4-8 | Me | Me | H | F | F | B8 | |
| 4-9 | Me | Me | H | F | F | B11 | |
| 4-10 | Me | Me | H | F | F | B21 | 120-122 |
| 4-11 | Me | Me | Me | H | H | B1 | |
| 4-12 | Me | Me | Me | H | H | B4 | |
| 4-13 | Me | Me | Me | H | H | B8 | |
| 4-14 | Me | Me | Me | H | H | B16 | |
| 4-15 | Me | Me | Me | H | H | B21 | |
| 4-16 | Me | Me | Me | F | F | B1 | |
| 4-17 | Me | Me | Me | F | F | B15 | |
| 4-18 | Me | Me | Me | F | F | B10 | |
| 4-19 | Me | Me | Me | F | F | B21 | 74-78 |
| 4-20 | Me | Me | Me | F | F | B25 | |
| 4-21 | Me | Me | Me | H | Me | B21 | |
| 4-22 | Me | Me | Me | H | Me | B16 | |

TABLE 4-continued

| No. | R¹ | R² | X¹ | X² | X³ | B | Physical properties (mp ° C.) |
|---|---|---|---|---|---|---|---|
| 4-23 | Me | Me | Me | H | Me | B14 | |
| 4-24 | Me | Me | Me | Me | H | B1 | |
| 4-25 | Me | Me | Me | Me | H | B5 | |
| 4-26 | Me | Me | Me | Me | H | B8 | |
| 4-27 | Me | Me | Me | H | Me | B1 | |
| 4-28 | Me | Me | Me | H | Me | B5 | |
| 4-29 | Me | Me | Me | H | Me | B8 | |
| 4-30 | Me | Me | Me | H | Me | B71 | |

TABLE 5

| No. | R¹ | R² | X¹ | X² | X³ | B | Physical properties (mp ° C.) |
|---|---|---|---|---|---|---|---|
| 5-1 | Me | Me | H | H | H | B1 | |
| 5-2 | Me | Me | H | H | H | B5 | |
| 5-3 | Me | Me | H | H | H | B7 | |
| 5-4 | Me | Me | H | H | H | B14 | |
| 5-5 | Me | Me | H | H | H | B15 | |
| 5-6 | Me | Me | Me | H | H | B1 | |
| 5-7 | Me | Me | Me | H | H | B5 | |
| 5-8 | Me | Me | Me | H | H | B8 | |
| 5-9 | Me | Me | Me | H | H | B11 | |
| 5-10 | Me | Me | Me | H | H | B21 | |
| 5-11 | Me | Me | H | F | F | B1 | |
| 5-12 | Me | Me | H | F | F | B4 | |
| 5-13 | Me | Me | H | F | F | B8 | |
| 5-14 | Me | Me | H | F | F | B16 | |
| 5-15 | Me | Me | H | F | F | B21 | |
| 5-16 | Me | Me | Me | F | F | B1 | |
| 5-17 | Me | Me | Me | F | F | B15 | |
| 5-18 | Me | Me | Me | F | F | B10 | |
| 5-19 | Me | Me | Me | F | F | B21 | |
| 5-20 | Me | Me | Me | F | F | B25 | |
| 5-21 | Me | Me | Me | H | Me | B21 | |
| 5-22 | Me | Me | Me | H | Me | B16 | |
| 5-23 | Me | Me | Me | H | Me | B14 | |
| 5-24 | Me | Me | Me | F | H | B1 | |
| 5-25 | Me | Me | Me | F | H | B5 | |
| 5-26 | Me | Me | Me | F | H | B8 | |
| 5-27 | Me | Me | Me | Me | H | B14 | |
| 5-28 | Me | Me | Me | Me | H | B16 | |
| 5-29 | Me | Me | Me | Me | H | B21 | |
| 5-30 | Me | Me | Me | Me | Me | B21 | |

TABLE 6

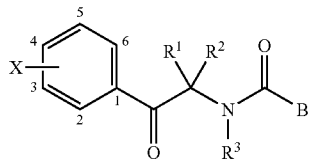

| No. | R¹ | R² | R³ | X | B | Physical properties (mp ° C.) |
|---|---|---|---|---|---|---|
| 6-1 | Me | Me | $CO_2Bu(t)$ | 4-Br | B21 | Oil |
| 6-2 | Me | Me | COMe | 4-Br | B21 | Oil |
| 6-3 | Me | Me | COMe | 3-Cl-4-Cl | B21 | Oil |
| 6-4 | Me | Me | Me | 3-Cl-4-Cl | B1 | 147-150 |
| 6-5 | Me | Me | $CO_2Bu(t)$ | 3-Cl-4-Cl | B21 | 66-68 |
| 6-6 | Me | Me | $SCCl_3$ | 3-Br-4-Cl | B1 | |
| 6-7 | Me | Me | SPh | 3-Cl-4-Br | B5 | |
| 6-8 | Me | Me | SOPh | 3-Me-4-Br | B8 | |
| 6-9 | Me | Me | $SO_2Ph$ | 3-Me-4-Cl | B14 | |
| 6-10 | Me | Me | $SO_2Me$ | 3-Cl-4-Cl | B16 | |
| 6-11 | Me | Me | $SO_2CF_3$ | 3-F-4-Cl | B21 | |
| 6-12 | Me | Me | $SO_2NMe_2$ | 2-Me-4-OMe | B71 | |
| 6-13 | Me | Me | $CH_2OMe$ | 2-Me-4-OEt | B1 | |
| 6-14 | Me | Me | $CH_2SMe$ | 2-Me-4-OPr(i) | B5 | |
| 6-15 | Me | Me | CN | 3-Br-4-Br | B8 | |
| 6-16 | Me | Me | CHO | 2-Me-4-Cl | B14 | |
| 6-17 | Me | Me | $CH_2CF_3$ | 2-Me-4-Br | B16 | |
| 6-18 | Me | Me | $OCH_2CF_3$ | 3-Br-4-Cl | B21 | |
| 6-19 | Me | Me | D3 | 3-Cl-4-Br | B71 | |
| 6-20 | Me | Me | OH | 3-Me-4-Br | B1 | |
| 6-21 | Me | Me | $CO_2CH_2Ph$ | 3-Me-4-Cl | B5 | |
| 6-22 | Me | Me | $CO_2CH_2OMe$ | 3-Cl-4-Cl | B8 | |
| 6-23 | Me | Me | COPh | 3-Cl-4-Cl | B14 | |
| 6-24 | Me | Me | $COCF_3$ | 3-Cl-4-Cl | B16 | |
| 6-25 | Me | Me | $CH_2C\equiv CH$ | 3-Cl-4-Cl | B21 | |
| 6-26 | Me | Me | $CH_2CH=CH_2$ | 3-F-4-Cl | B71 | |
| 6-27 | Me | Me | $CH_2CN$ | 2-Me-4-OMe | B1 | |
| 6-28 | Me | Me | Cyclopentyloxy | 2-Me-4-OEt | B5 | |
| 6-29 | Me | Me | $CH_2CH_2OCHF_2$ | 2-Me-4-OPr(i) | B8 | |
| 6-30 | Me | Me | $CH_2CH_2NH_2$ | 3-Br-4-Br | B14 | |
| 6-31 | Me | Me | $CH_2CH_2NHMe$ | 2-Me-4-Cl | B16 | |
| 6-32 | Me | Me | $CH_2CH_2NMe_2$ | 2-Me-4-Br | B21 | |

TABLE 7

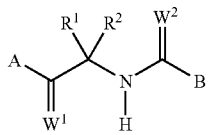

| No. | A | W¹ | R¹ | R² | W² | B | Physical properties (mp ° C.) |
|---|---|---|---|---|---|---|---|
| 7-1 | 2-thienyl | O | Me | Me | O | B1 | 101-105 |
| 7-2 | 2-thienyl | O | Me | Me | O | B21 | 118-121 |
| 7-3 | 3-thienyl | O | Me | Me | O | B1 | 121-125 |
| 7-4 | 5-Cl-3-thienyl | O | Me | Me | O | B21 | 138-142 |
| 7-5 | 2-Cl-5-Cl-3-thienyl | O | Me | Me | O | B21 | 119-121 |
| 7-6 | 5-Cl-2-thienyl | O | Me | Me | O | B21 | 127-132 |
| 7-7 | 5-Cl-2-thienyl | O | Me | Me | O | B1 | 115-120 |
| 7-8 | 4-Cl-2-thienyl | O | Me | Me | O | B21 | 119-121 |
| 7-9 | 4-Cl-2-thienyl | O | Me | Me | O | B1 | Oil |
| 7-10 | 1-naphthyl | O | Me | Me | O | B48 | |
| 7-11 | 1-naphthyl | O | Me | Me | O | B49 | |
| 7-12 | 1-naphthyl | O | Me | Me | O | B19 | |
| 7-13 | 1-naphthyl | O | Me | Me | O | B20 | |
| 7-14 | 1-naphthyl | O | Me | Me | O | B50 | |
| 7-15 | 1-naphthyl | O | Me | Me | O | B12 | |
| 7-16 | 1-naphthyl | O | Me | Me | O | B13 | |
| 7-17 | 2-thienyl | O | Me | Me | O | B48 | |
| 7-18 | 2-thienyl | O | Me | Me | O | B49 | |
| 7-19 | 2-thienyl | O | Me | Me | O | B19 | |
| 7-20 | 2-thienyl | O | Me | Me | O | B20 | |
| 7-21 | 2-thienyl | O | Me | Me | O | B50 | |
| 7-22 | 2-thienyl | O | Me | Me | O | B12 | |
| 7-23 | 2-thienyl | O | Me | Me | O | B13 | |
| 7-24 | 3-thienyl | O | Me | Me | O | B48 | |
| 7-25 | 3-thienyl | O | Me | Me | O | B49 | |
| 7-26 | 3-thienyl | O | Me | Me | O | B19 | |
| 7-27 | 3-thienyl | O | Me | Me | O | B20 | |
| 7-28 | 3-thienyl | O | Me | Me | O | B50 | |
| 7-29 | 3-thienyl | O | Me | Me | O | B12 | |
| 7-30 | 3-thienyl | O | Me | Me | O | B13 | |
| 7-31 | 2-pyridyl | O | Me | Me | O | B48 | |
| 7-32 | 2-pyridyl | O | Me | Me | O | B49 | |
| 7-33 | 2-pyridyl | O | Me | Me | O | B19 | |
| 7-34 | 2-pyridyl | O | Me | Me | O | B20 | |
| 7-35 | 2-pyridyl | O | Me | Me | O | B50 | |
| 7-36 | 2-pyridyl | O | Me | Me | O | B12 | |
| 7-37 | 2-pyridyl | O | Me | Me | O | B13 | |
| 7-38 | 3-pyridyl | O | Me | Me | O | B48 | |
| 7-39 | 3-pyridyl | O | Me | Me | O | B49 | |
| 7-40 | 3-pyridyl | O | Me | Me | O | B19 | |
| 7-41 | 3-pyridyl | O | Me | Me | O | B20 | |
| 7-42 | 3-pyridyl | O | Me | Me | O | B50 | |
| 7-43 | 3-pyridyl | O | Me | Me | O | B12 | |
| 7-44 | 4-pyridyl | O | Me | Me | O | B13 | |
| 7-45 | 4-pyridyl | O | Me | Me | O | B48 | |
| 7-46 | 4-pyridyl | O | Me | Me | O | B49 | |
| 7-47 | 4-pyridyl | O | Me | Me | O | B19 | |
| 7-48 | 4-pyridyl | O | Me | Me | O | B20 | |
| 7-49 | 4-pyridyl | O | Me | Me | O | B50 | |
| 7-50 | 4-pyridyl | O | Me | Me | O | B12 | |
| 7-51 | 4-pyridyl | O | Me | Me | O | B13 | |
| 7-52 | Indol-3-yl | O | Me | Me | O | B48 | |
| 7-53 | Indol-3-yl | O | Me | Me | O | B49 | |
| 7-54 | Indol-3-yl | O | Me | Me | O | B19 | |
| 7-55 | Indol-3-yl | O | Me | Me | O | B20 | |
| 7-56 | Indol-3-yl | O | Me | Me | O | B50 | |
| 7-57 | Indol-3-yl | O | Me | Me | O | B12 | |
| 7-58 | Indol-3-yl | O | Me | Me | O | B13 | |
| 7-59 | N-Me-indol-3-yl | O | Me | Me | O | B48 | |
| 7-60 | N-Me-indol-3-yl | O | Me | Me | O | B49 | |
| 7-61 | N-Me-indol-3-yl | O | Me | Me | O | B19 | |
| 7-62 | N-Me-indol-3-yl | O | Me | Me | O | B20 | |
| 7-63 | N-Me-indol-3-yl | O | Me | Me | O | B50 | |
| 7-64 | N-Me-indol-3-yl | O | Me | Me | O | B12 | |
| 7-65 | N-Me-indol-3-yl | O | Me | Me | O | B13 | |
| 7-66 | 3-thienyl | O | Me | Me | O | B21 | 131-133 |
| 7-67 | Ph(3,4-Cl₂) | S | Me | Me | O | B21 | |
| 7-68 | Ph(3,4-Cl₂) | O | Me | Me | S | B21 | |
| 7-69 | 2-Cl-5-pyridyl | O | Me | Me | O | B21 | |
| 7-70 | 3-pyridyl | O | Me | Me | O | B21 | |
| 7-71 | 2-OMe-5-pyridyl | O | Me | Me | O | B21 | |
| 7-72 | 2-Cl-5-pyridyl | O | Me | Me | O | B16 | |
| 7-73 | 2-OMe-5-pyridyl | O | Me | Me | O | B16 | |
| 7-74 | 5-OMe-2-pyridyl | O | Me | Me | O | B21 | |
| 7-75 | 5-OMe-2-pyridyl | O | Me | Me | O | B16 | |
| 7-76 | 5-Cl-2-pyridyl | O | Me | Me | O | B21 | |
| 7-77 | 5-Cl-2-pyridyl | O | Me | Me | O | B16 | |

TABLE 8

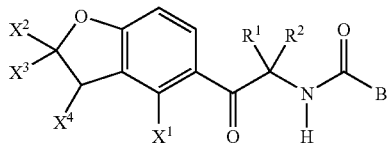

| No. | R¹ | R² | X¹ | X² | X³ | X⁴ | B | Physical properties (mp ° C.) |
|---|---|---|---|---|---|---|---|---|
| 8-1 | Me | Me | Me | F | F | H | B1 | |
| 8-2 | Me | Me | Me | F | F | H | B5 | |
| 8-3 | Me | Me | Me | F | F | H | B8 | |
| 8-4 | Me | Me | Me | F | F | H | B14 | |
| 8-5 | Me | Me | Me | F | F | H | B16 | |
| 8-6 | Me | Me | Me | F | F | H | B21 | |
| 8-7 | Me | Me | Me | F | F | H | B71 | |
| 8-8 | Me | Me | Me | H | H | H | B1 | |
| 8-9 | Me | Me | Me | H | H | H | B14 | |
| 8-10 | Me | Me | Me | H | H | H | B16 | |
| 8-11 | Me | Me | Me | Me | H | H | B1 | |
| 8-12 | Me | Me | Me | Me | H | H | B5 | |
| 8-13 | Me | Me | Me | Me | H | H | B8 | |
| 8-14 | Me | Me | Me | Me | H | H | B14 | |
| 8-15 | Me | Me | Me | Me | H | H | B16 | |
| 8-16 | Me | Me | Me | Me | H | H | B21 | |
| 8-17 | Me | Me | Me | Me | H | H | B71 | |
| 8-18 | Me | Me | Me | Me | Me | H | B1 | |
| 8-19 | Me | Me | Me | Me | Me | H | B5 | |
| 8-20 | Me | Me | Me | Me | Me | H | B8 | |
| 8-21 | Me | Me | Me | Me | Me | H | B14 | |
| 8-22 | Me | Me | Me | Me | Me | H | B16 | |
| 8-23 | Me | Me | Me | Me | Me | H | B21 | |
| 8-24 | Me | Me | Me | Me | Me | H | B71 | |
| 8-25 | Me | Me | H | F | F | H | B5 | |
| 8-26 | Me | Me | H | F | F | H | B8 | |
| 8-27 | Me | Me | Me | F | F | Me | B14 | |
| 8-28 | Me | Me | Me | F | F | Me | B16 | |
| 8-29 | Me | Me | Me | Me | H | Me | B21 | |
| 8-30 | Me | Me | Me | Me | Me | Me | B71 | |

TABLE 9

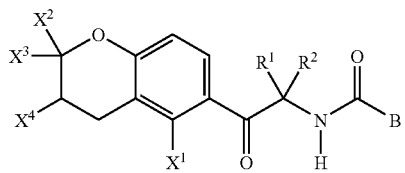

| No. | R¹ | R² | X¹ | X² | X³ | X⁴ | B | Physical properties (mp ° C.) |
|---|---|---|---|---|---|---|---|---|
| 9-1 | Me | Me | Me | F | F | H | B1 | |
| 9-2 | Me | Me | Me | F | F | H | B5 | |
| 9-3 | Me | Me | Me | F | F | H | B8 | |
| 9-4 | Me | Me | Me | F | F | H | B14 | |
| 9-5 | Me | Me | Me | F | F | H | B16 | |
| 9-6 | Me | Me | Me | F | F | H | B21 | |
| 9-7 | Me | Me | Me | F | F | H | B71 | |
| 9-8 | Me | Me | Me | H | H | H | B1 | |
| 9-9 | Me | Me | Me | H | H | H | B14 | |
| 9-10 | Me | Me | Me | H | H | H | B16 | |
| 9-11 | Me | Me | Me | Me | H | H | B1 | |
| 9-12 | Me | Me | Me | Me | H | H | B5 | |
| 9-13 | Me | Me | Me | Me | H | H | B8 | |
| 9-14 | Me | Me | Me | Me | H | H | B14 | |
| 9-15 | Me | Me | Me | Me | H | H | B16 | |
| 9-16 | Me | Me | Me | Me | H | H | B21 | |
| 9-17 | Me | Me | Me | Me | H | H | B71 | |
| 9-18 | Me | Me | Me | Me | Me | H | B1 | |
| 9-19 | Me | Me | Me | Me | Me | H | B5 | |
| 9-20 | Me | Me | Me | Me | Me | H | B8 | |
| 9-21 | Me | Me | Me | Me | Me | H | B14 | |
| 9-22 | Me | Me | Me | Me | Me | H | B16 | |
| 9-23 | Me | Me | Me | Me | Me | H | B21 | |
| 9-24 | Me | Me | Me | Me | Me | H | B71 | |
| 9-25 | Me | Me | H | F | F | H | B5 | |
| 9-26 | Me | Me | H | F | F | H | B8 | |
| 9-27 | Me | Me | Me | F | F | Me | B14 | |
| 9-28 | Me | Me | Me | F | F | Me | B16 | |
| 9-29 | Me | Me | Me | Me | H | Me | B21 | |
| 9-30 | Me | Me | Me | Me | Me | Me | B71 | |

TABLE 10

| No. | ¹H-NMR δppm (Solvent: CDCl₃/400 MHz) |
|---|---|
| 1-21 | 1.73 (s, 6H), 6.97 (d, 1H), 7.42 (m, 2H), 7.59 (s, 1H), 7.84 (dd, 1H), 8.10 (d, 1H) |
| 1-24 | 1.56 (s, 6H), 1.71 (s, 3H), 6.44 (s, 1H), 6.71 (dd, 1H), 7.30 (d, 1H), 7.41 (d, 1H), 7.82 (dd, 1H), 8.08 (d, 1H) |
| 1-28 | 1.76 (s, 6H), 2.34 (s, 3H), 2.40 (s, 3H), 6.83 (m, 2H), 7.23 (m, 3H), 7.74 (m, 3H) |
| 1-29 | 1.74 (s, 6H), 2.33 (s, 3H), 6.51 (s, 1H), 6.83 (d, 1H), 7.22 (d, 1H), 7.50 (t, 1H), 7.70 (d, 1H), 8.18 (d, 1H), 8.26 (s, 1H) |
| 1-46 | 1.73 (s, 6H), 3.88 (s, 3H), 6.75 (s, 1H), 7.45 (d, 1H), 7.83 (m, 2H), 8.10 (d, 1H) |
| 1-76 | 1.71 (s, 6H), 6.70 (t, 1H), 6.90 (d, 1H), 7.42 (m, 3H), 7.81 (dd, 1H), 8.06 (d, 1H) |
| 1-120 | 1.72 (s, 6H), 2.24 (s, 3H), 2.35 (s, 3H), 2.47 (s, 3H), 6.80 (s, 1H), 6.86 (d, 1H), 7.20 (d, 2H), 7.25 (d, 1H) |
| 1-121 | 1.76 (s, 6H), 2.34 (s, 3H), 2.53 (s, 3H), 6.88 (d, 1H), 6.94 (s, 1H), 7.09 (d, 1H), 7.24 (d, 1H), 7.28 (d, 1H) |
| 1-123 | 1.50 (d, 3H), 2.26 (s, 3H), 2.56 (s, 3H), 5.66 (m, 1H), 6.70 (bd, 1H), 7.48 (bd, 1H), 7.96 (d, 2H) |
| 1-136 | 1.81 (s, 6H), 2.24 (s, 3H), 2.39 (s, 3H), 6.78 (d, 1H), 6.83 (d, 1H), 7.20 (d, 1H), 7.22 (m, 2H), 7.40 (d, 2H), 8.03 (d, 2H) |
| 1-140 | 1.73 (s, 6H), 2.24 (s, 3H), 2.47 (s, 3H), 6.58 (s, 1H), 6.75 (d, 1H), 7.15 (d, 1H), 7.22 (d, 1H), 7.33 (d, 1H), 7.54 (d, 1H), 7.63 (dd, 1H), 7.91 (dd, 1H), 8.21 (d, 1H) |
| 1-143 | 1.76 (s, 3H), 2.17 (s, 3H), 2.36 (s, 3H), 6.71 (s, 1H), 6.83 (d, 1H), 7.00 (d, 1H), 7.10 (d, 1H), 7.20 (d, 1H), 7.41 (d, 1H), 7.47 (d, 1H), 7.93 (dd, 1H), 7.96 (d, 1H) |
| 1-144 | 1.77 (s, 6H), 2.38 (s, 3H), 6.45 (d, 1H), 6.67 (d, 1H), 6.83 (d, 1H), 7.22 (d, 1H), 7.40 (d, 1H), 7.47 (d, 1H), 7.75 (dd, 1H), 7.83 (dd, 1H), 8.26 (d, 1H) |

TABLE 10-continued

| No. | $^1$H-NMR δppm (Solvent: CDCl$_3$/400 MHz) |
|---|---|
| 1-148 | 1.72 (s, 6H), 2.53 (s, 3H), 2.65 (s, 3H), 6.38 (s, 1H), 7.44 (d, 1H), 7.89 (dd, 1H), 8.05 (d, 1H) |
| 1-149 | 1.74 (s, 6H), 7.45 (d, 1H), 7.74 (s, 1H), 7.82 (dd, 1H), 8.07 (d, 1H) |
| 1-157 | 1.76 (s, 6H), 7.38 (d, 1H), 7.55 (d, 1H), 7.59 (d, 1H), 7.83 (dd, 1H), 8.09 (d, 1H), 9.98 (s, 1H) |
| 1-179 | 1.72 (s, 6H), 2.21 (s, 3H), 2.22 (s, 3H), 2.45 (s, 3H), 6.50 (t, 1H), 6.78 (s, 1H), 6.85 (d, 1H), 6.91 (d, 1H), 7.25 (m, 2H) |
| 1-181 | 1.32 (d, 6H), 1.72 (s, 6H), 2.36 (s, 3H), 2.46 (s, 3H), 2.80 (m, 1H), 6.74 (s, 1H), 6.84-6.92 (m, 2H), 6.98 (s, 1H), 7.25 (d, 1H), 7.52 (d, 1H) |
| 1-184 | 1.73 (s, 6H), 2.46 (s, 3H), 3.82 (s, 3H), 6.84 (d, 1H), 6.85-6.91 (m, 3H), 7.00 (t, 1H), 7.26 (d, 1H), 7.27-7.39 (m, 2H) |
| 1-187 | 1.75 (s, 6H), 2.38 (s, 3H), 2.43 (s, 3H), 4.35 (q, 2H), 6.69 (s, H), 6.71 (dd, 1H), 6.82 (d, 1H), 6.86 (d, 1H), 7.25 (d, 1H), 7.52 (d, 1H) |
| 1-189 | 1.52 (d, 3H), 2.57 (s, 3H), 5.67 (m, 1H), 6.90 (d, 1H), 7.0 (bd, 1H), 7.31 (d, 1H), 7.50 (d, 2H), 7.97 (d, 2H) |
| 1-231 | 1.77 (s, 6H), 2.25 (s, 3H), 2.48 (s, 3H), 3.77 (s, 3H), 6.85 (dd, 1H), 6.87 (d, 1H), 6.89 (s, 1H), 6.97 (d, 1H), 7.15 (d, 1H), 7.26 (d, 1H) |
| 1-270 | 1.75 (s, 6H), 2.29 (s, 3H), 2.36 (s, 3H), 2.44 (s, 3H), 6.73 (s, 1H), 6.86 (d, 1H), 6.91 (dd, 1H), 6.99 (d, 1H), 7.25 (d, 1H), 7.51 (d, 1H) |
| 1-271 | 1.31 (d, 9H), 1.73 (s, 6H), 2.31 (s, 3H), 2.44 (s, 3H), 6.75 (s, 1H), 6.85 (d, 2H), 7.17 (dd, 1H), 7.25 (d, 1H), 7.28 (bs, 1H), 7.39 (d, 1H) |
| 1-273 | 0.96 (t, 3H), 1.26-1.31 (m, 3H), 1.61-1.75 (m, 2H), 2.35 (s, 3H), 2.44 (s, 3H), 4.32 (m, 1H), 6.64 (dd, 1H), 6.75 (d, 1H), 6.85 (d, 1H), 6.88 (s, 1H), 7.24 (d, 1H), 7.47 (d, 1H) |
| 1-276 | 1.75 (s, 6H), 2.38 (s, 3H), 2.43 (s, 3H), 6.71 (s, 1H), 6.85 (d, 1H) 7.24 (d, 1H), 7.32 (dd, 1H), 7.34-7.36 (m, 3H), 7.43 (bs, 1H), 7.51-7.54 (m, 2H) |
| 1-282 | 0.24 (s, 9H), 1.73 (s, 6H), 2.33 (s, 3H), 2.44 (s, 3H), 6.68 (s, 1H), 6.86 (d, 1H), 7.24 (dd, 1H), 7.25 (d, 1H), 7.36 (bs, 1H), 7.42 (d, 1H) |
| 1-516 | 1.78 (s, 6H), 2.53 (s, 3H), 3.79 (s, 3H), 6.76 (s, 1H), 6.83 (dd, 1H), 6.89 (d, 1H), 7.14 (d, 1H), 7.29 (d, 1H), 7.47 (d, 1H) |
| 1-518 | 1.78 (s, 6H), 4.43 (s, 2H), 6.96 (d, 1H), 7.38 (d, 2H), 7.41 (d, 1H), 7.80 (s, 1H), 7.96 (d, 2H) |
| 1-521 | 1.74 (s, 6H), 2.13 (s, 6H), 3.34 (s, 2H), 6.87 (d, 1H), 7.25 (d, 2H), 7.32 (d, 1H), 7.86 (s, 1H), 7.88 (d, 2H) |
| 1-536 | 1.73 (s, 6H), 2.48 (s, 3H), 6.75 (s, 1H), 6.85 (d, 1H), 7.22-7.26 (m, 2H), 7.32 (dt, 1H), 7.55-7.58 (m, 2H) |
| 1-539 | 1.80 (s, 6H), 2.30 (s, 6H), 3.56 (s, 2H), 7.01 (d, 1H), 7.39 (m, 3H), 7.93 (s, 1H), 7.98 (d, 2H) |
| 2-4 | 1.87 (s, 6H), 2.45 (s, 3H), 3.80 (s, 3H), 7.54 (m, 2H), 7.69 (s, 1H), 7.90 (m, 3H), 8.00 (d, 1H), 8.50 (s, 1H) |
| 6-1 | 0.75 (s, 3H), 1.34 (s, 9H), 1.59 (s, 3H), 2.57 (s, 3H), 6.93 (d, 1H), 7.38 (d, 1H), 7.39 (d, 2H)7.54 (d, 2H), |
| 6-2 | 0.74 (s, 3H), 1.62 (s, 3H), 2.04 (s, 3H), 2.56 (s, 3H), 6.92 (d, 1H), 7.35 (d, 1H), 7.37 (d, 2H), 7.53 (d, 2H), |
| 6-3 | 1.60 (s, 6H), 2.04 (s, 3H), 2.54 (s, 3H), 6.91 (d, 1H), 7.29 (m, 1H), 7.36 (m, 1H), 7.45 (d, 1H), 7.54 (s, 1H) |
| 7-9 | 1.60 (s, 6H), 2.30 (s, 3H), 3.76 (s, 3H), 6.67 (s, 1H), 6.91 (d, 1H), 7.25 (d, 1H) |

Now, Test Examples for the composition of the present invention will be described. In each test, the controlling index was determined on the basis of the following standards:
[Controlling Index]:[Degree of Disease Outbreak:Visual Observation]

5: No lesions nor sporulation recognizable

4: Area of lesions, length of lesions, number of lesions or area of sporulation is less than 10% of non-treated plot 3: Area of lesions, length of lesions, number of lesions or area of sporulation is less than 40% of non-treated plot 2: Area of lesions, length of lesions, number of lesions or area of sporulation is less than 70% of non-treated plot 1: Area of lesions, length of lesions, number of lesions or area of sporulation is at least 70% of non-treated plot Test Example 1

Test on Preventive Effect Against Wheat Powdery Mildew

Wheat (cultivar: Norin-61-go) was cultivated in a plastic pot having a diameter of 7.5 cm, and when it reached 1.5-leaf stage, 10 ml of a chemical solution having the acid amide derivative of the formula (I) or a salt thereof adjusted to a prescribed concentration, was applied by a spray gun. After the chemical solution dried (the same day as the application), conidia of *Erysiphe graminis* were dusted and inoculated and maintained in a constant temperature chamber at 20° C. From 6 to 7 days after the inoculation, the area of sporulation was investigated, and the controlling index was determined in accordance with the above evaluation standards. The test was carried out with respect to the above compounds No. 1-13, 1-29, 1-39, 1-54, 1-90, 1-96, 1-100, 1-101, 1-106, 1-107, 1-109, 1-124, 1-125, 1-127, 1-148, 1-152, 1-156, 1-174, 1-175, 1-190, 1-205, 1-516, 3-4, 3-9, 3-10, 3-12, 3-19, 3-20, 4-19, 6-1 and 7-2, and all compounds showed effects with a controlling index of 4 or 5 at a concentration of 500 ppm.

Test Example 2

Test on Preventive Effect Against Cucumber Powdery Mildew

Cucumber (cultivar: Sagamihanpaku) was cultivated in a plastic pot having a diameter of 7.5 cm, and when it reached 1.5-leaf stage, 10 ml of a chemical solution having the acid amide derivative of the formula (I) or a salt thereof adjusted to a prescribed concentration, was applied by a spray gun. After the chemical solution dried (the same day as the application or the next day), a suspension of conidia of *Sphaerotheca fuliginea* was sprayed and inoculated and maintained in a constant temperature chamber at 20° C. From 6 to 7 days after the inoculation, the area of sporulation was investigated, and the controlling index was determined in accordance with the above evaluation standards. The test was carried out with respect to the above compounds No. 1-6, 1-9, 1-11, 1-14, 1-15, 1-17 to 1-22, 1-27 to 1-29, 1-32, 1-33, 1-36, 1-39, 1-41 to 1-43, 1-47, 1-53 to 1-56, 1-62 to 1-64, 1-66, 1-73, 1-77, 1-79, 1-90, 1-93, 1-97 to 1-104, 1-106 to 1-108, 1-111, 1-115, 1-119, 1-120, 1-124, 1-127, 1-129, 1-131, 1-148, 1-150, 1-152, 1-156, 1-160, 1-161, 1-164, 1-165, 1-167, 1-170, 1-172, 1-174, 1-175, 1-190, 1-205, 1-516, 2-1, 2-14, 3-2, 3-4, 3-6, 3-9, 3-10, 3-12, 3-19, 3-20, 3-23, 4-10 and 6-1 to 6-3, and all compounds showed effects with a controlling index of 4 or 5 at a concentration of 500 ppm. The test was carried out with respect to the above compound No. 1-34, it showed an effect with a controlling index of 4 at a concentration of 200 ppm.

Test Example 3

Test on Preventive Effect Against Rice Blast

Rice (cultivar: Nihonbare) was cultivated in a plastic pot having a diameter of 7.5 cm, and when it reached 1.5-leaf stage, 10 ml of a chemical solution having the acid amide derivative of the formula (I) or a salt thereof adjusted to a prescribed concentration, was applied by a spray gun. After the chemical solution dried (the same day as the application or the next day), a suspension of conidia of *Pyricularia oryzae* was sprayed and inoculated and maintained in an inoculation box at 20° C. for 24 hours and thereafter maintained in a constant temperature chamber at 20° C. From 5 to 7 days after the inoculation, the number of lesions were investigated, and the controlling index was determined in accordance with the above evaluation standards. The test was carried out with respect to the above compounds No. 1-6, 1-9, 1-13, 1-14, 1-28, 1-45, 1-47, 1-52, 1-53, 1-55, 1-56, 1-62, 1-63, 1-66, 1-75, 1-77, 1-79, 1-109, 1-119, 1-164, 2-1, 2-2, 3-25 and 4-19, and all compounds showed effects with a controlling index of 4 or 5 at a concentration of 500 ppm.

Test Example 4

Test on Preventive Effect Against Kidney Bean Gray Mold

Kidney bean (cultivar: Taisyou Kintoki) was cultivated in a plastic pot having a diameter of 15 cm, and when the main leaf developed sufficiently, 10 ml of a chemical solution having the acid amide derivative of the formula (I) or a salt thereof adjusted to a prescribed concentration, was applied by a spray gun. After the chemical solution dried (the same day as the application or the next day), a suspension of spores of *Botrytis cinerea* (potato-glucose extract diluted to 50% with water) was inoculated and maintained in a constant temperature chamber at 20° C. Three days after the inoculation, the length of lesions (mm) was investigated, and the controlling index was determined in accordance with the above evaluation standards. The test was carried out with respect to the above compounds No. 1-11, 1-15, 1-17, 1-20, 1-22, 1-27, 1-41, 1-43, 1-52, 1-80, 1-99, 1-102, 1-112 to 1-115, 1-117, 1-118, 1-120, 1-125, 1-131, 1-136, 1-160, 1-162, 1-169, 1-172, 1-176, 1-180, 1-182, 1-186 to 1-189, 1-273, 2-2, 2-9, 2-13, 2-14 and 7-6, and all compounds showed effects with a controlling index of 4 or 5 at a concentration of 500 ppm.

Test Example 5

Test on Preventive Effect Against Kidney Bean Stem Rot

Kidney bean (cultivar: Taisyou Kintoki) was cultivated in a plastic pot having a diameter of 15 cm, and when the main leaf developed sufficiently, 10 ml of a chemical solution having the acid amide derivative of the formula (I) or a salt thereof adjusted to a prescribed concentration, was applied by a spray gun. After the chemical solution dried (the same day as the application or the next day), mycelial disc of *Sclerotinia sclerotiorum* was inoculated and maintained in a constant temperature chamber at 20° C. Three days after the inoculation, the length of lesions (mm) was investigated, and the controlling index was determined in accordance with the above evaluation standards. The test was carried out with respect to the above compounds 1-1, 1-4, 1-7, 1-10, 1-16, 1-18, 1-19, 1-21, 1-26, 1-30 to 1-33, 1-36, 1-38, 1-42, 1-44, 1-46, 1-57, 1-60, 1-64, 1-69, 1-71, 1-73, 1-75, 1-80, 1-86, 1-93, 1-96 to 1-98, 1-103 to 1-105, 1-108, 1-111 to 1-114, 1-117, 1-118, 1-123, 1-126, 1-128, 1-129, 1-133 to 1-136, 1-141 to 1-144, 1-146, 1-149, 1-150, 1-159, 1-161 to 1-163, 1-165 to 1-171, 1-176, 1-180, 1-181, 1-186, 1-188, 1-208, 1-209, 1-271, 1-273, 1-276, 1-535, 2-1, 2-3, 2-4, 2-10, 2-11, 2-13, 3-2, 3-3, 3-6, 3-23, 3-26, 4-10, 6-2, 6-3, 7-2, 7-4, 7-6 to 7-8, and 7-66, and all compounds showed effects with a controlling index of 4 or 5 at a concentration of 500 ppm.

Test Example 6

Test on Preventive Effect Against Wheat Glume Blotch

Wheat (cultivar: Norin-61-go) was cultivated in a plastic pot having a diameter of 7.5 cm, and when it reached 1.5-leaf stage, 10 ml of a chemical solution having the acid amide derivative of the formula (I) or a salt thereof adjusted to a prescribed concentration, was applied by a spray gun. After the chemical solution dried (the same day as the application), a suspension of conidia of *Septoria nodorum* was sprayed and inoculated and maintained in an inoculation box at 20° C. for 72 hours and thereafter maintained in a constant temperature chamber at 20° C. From 5 to 10 days after the inoculation, the number of lesions was investigated, and the controlling index was determined in accordance with the above evaluation standards. The test was carried out with respect to the above compounds No. 1-179 and 1-189, and all compounds showed effects with a controlling index of 4 or 5 at a concentration of 500 ppm.

Test Example 7

Test on Preventive Effect Against Rice Sheath Blight

Rice (cultivar: Nihonbare) was cultivated in a plastic pot having a diameter of 7.5 cm, and when it reached 5-leaf stage, 10 ml of a chemical solution having the acid amide derivative of the formula (I) or a salt thereof adjusted to a prescribed concentration, was applied by a spray gun. After the chemical solution dried (the same day as the application or next day), mycelial disc of *Rhizoctonia solani* preliminarily cultured, was inserted in a leaf sheath and fixed by a string, and maintained in an inoculation box at 25° C. From 5 to 7 days after the inoculation, the length of lesions was investigated, and the controlling index was determined in accordance with the above evaluation standards. The test was carried out with respect to the above compounds No. 1-130, 1-137 and 3-3, and all compounds showed effects with a controlling index of 4 or 5 at a concentration of 500 ppm.

Now, Formulation Examples of the composition of the present invention will be described below. However, the weight ratio, type of formulation or the like is by no means restricted to the following Examples.

Formulation Example 1

| | |
|---|---|
| (1) Compound of the formula (I) | 20 parts by weight |
| (2) Clay | 72 parts by weight |
| (3) Sodium lignin sulfonate | 8 parts by weight |

The above components are uniformly mixed to obtain a wettable powder.

Formulation Example 2

| | |
|---|---|
| (1) Compound of the formula (I) | 5 parts by weight |
| (2) Talc | 95 parts by weight |

The above components are uniformly mixed to obtain a dust.

Formulation Example 3

| | |
|---|---|
| (1) Compound of the formula (I) | 20 parts by weight |
| (2) N,N'-dimethylacetamide | 20 parts by weight |
| (3) Polyoxyethylene alkyl phenyl ether | 10 parts by weight |
| (4) Xylene | 50 parts by weight |

The above components are uniformly mixed and dissolved to obtain an emulsifiable concentrate.

Formulation Example 4

| | |
|---|---|
| (1) Clay | 68 parts by weight |
| (2) Sodium lignin sulfonate | 2 parts by weight |
| (3) Polyoxyethylene alkyl aryl sulfate | 5 parts by weight |
| (4) Fine silica | 25 parts by weight |

A mixture of the above components and the compound of the formula (I) are mixed in a weight ratio of 4:1 to obtain a wettable powder.

Formulation Example 5

| | |
|---|---|
| (1) Compound of the formula (I) | 50 parts by weight |
| (2) Oxylated polyalkylphenyl phosphate-triethanolamine | 2 parts by weight |
| (3) Silicone | 0.2 part by weight |
| (4) Water | 47.8 parts by weight |

The above components are uniformly mixed and pulverized to obtain a stock solution, and (5) Sodium polycarboxylate 5 parts by weight
(6) Anhydrous sodium sulfate 42.8 parts by weight are further added thereto, followed by uniform mixing, granulation and drying to obtain a water-dispersible granules.

Formulation Example 6

| | |
|---|---|
| (1) Compound of the formula (I) | 5 parts by weight |
| (2) Polyoxyethylene octylphenyl ether | 1 part by weight |
| (3) Phosphate of polyoxyethylene | 0.1 part by weight |
| (4) Particulate calcium carbonate | 93.9 parts by weight |

The above components (1) to (3) are preliminarily mixed uniformly and diluted with a proper amount of acetone, the diluted mixture is sprayed on the component (4), and acetone is removed to obtain granules.

Formulation Example 7

| | |
|---|---|
| (1) Compound of the formula (I) | 2.5 parts by weight |
| (2) N-methyl-2-pyrrolidone | 2.5 parts by weight |
| (3) Soybean oil | 95.0 parts by weight |

The above components are uniformly mixed and dissolved to obtain an ultra low volume formulation.

Formulation Example 8

| | |
|---|---|
| (1) Compound of the formula (I) | 20 parts by weight |
| (2) Oxylated polyalkylphenol phosphate triethanolamine | 2 parts by weight |
| (3) Silicone | 0.2 part by weight |
| (4) Xanthan gum | 0.1 part by weight |
| (5) Ethylene glycol | 5 parts by weight |
| (6) Water | 72.7 parts by weight |

The above components are uniformly mixed and pulverized to obtain a water-based suspension concentrate.

The invention claimed is:
1. A method for controlling noxious fungi, the method comprising applying, to the noxious fungi, an acid amide of the formula (I), or a salt thereof, in an amount effective to control the noxious fungi,

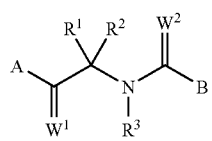

wherein
- A is phenyl which is optionally substituted by X, benzyl which is optionally substituted by X, naphthyl which is optionally substituted by X, heterocyclic ring which is optionally substituted by X, fused heterocyclic ring which is optionally substituted by X, indanyl, wherein the indanyl is optionally substituted by halogen, alkyl, or alkoxy, or tetrahydronaphthyl, wherein the tetrahydronaphthyl is optionally substituted by halogen, alkyl, or alkoxy;
- B is heterocyclic ring, excluding pyridyl, which is optionally substituted by Y, fused heterocyclic ring which is optionally substituted by Y, or naphthyl which is optionally substituted by Y;
- X is halogen, with the proviso that X is not bromine, alkyl which is optionally substituted by $E^1$, alkenyl which is optionally substituted by $E^1$, alkynyl which is optionally substituted by $E^1$, hydroxy, cyanooxy, alkoxy which is optionally substituted by $E^1$, alkenyloxy which is optionally substituted by $E^1$, alkynyloxy which is optionally substituted by $E^1$, mercapto, cyanothio, alkylthio which is optionally substituted by $E^1$, alkenylthio which is optionally substituted by $E^1$, alkynylthio which is optionally substituted by $E^1$, alkylsulfinyl which is optionally substituted by $E^2$, alkylsulfonyl which is optionally substituted by $E^2$, cycloalkyl which is optionally substituted by J, cycloalkyloxy which is optionally substituted by J, cycloalkylthio which is optionally substituted by J, cyano, nitro, formyl, phenyl which is optionally substituted by Y, phenoxy which is optionally substituted by Y, phenylthio which is optionally substituted by Y, phenylalkyl which is optionally substituted by Y, phenylalkenyl which is optionally substituted by Y, phenylalkynyl which is optionally substituted by Y, phenylalkyloxy which is optionally substituted by Y, phenylalkenyloxy which is optionally substituted by Y, phenylalkynyloxy which is optionally substituted by Y, phenylalkylthio which is optionally substituted by Y, phenylalkenylthio which is optionally substituted by Y, phenylalkynylthio which is optionally substituted by Y, phenylamino which is optionally substituted by Y, —$OR^4$, —$SR^5$, —$NR^6$, $R^7$, —$CO_2R^8$, —C(=O)$NR^8$, $R^9$, —$SO_2NR^8$, $R^9$, —CH=$NR^{10}$, or a heterocyclic ring, wherein the heterocyclic ring is optionally substituted by halogen, alkyl, haloalkyl, alkoxy, haloalkoxy, or alkylcarbonyl;
- Y is halogen, alkyl which is optionally substituted by $E^1$, alkenyl which is optionally substituted by $E^1$, alkynyl which is optionally substituted by $E^1$, hydroxy, cyanooxy, alkoxy which is optionally substituted by $E^1$, alkenyloxy which is optionally substituted by $E^1$, alkynyloxy which is optionally substituted by $E^1$, mercapto, cyanothio, alkylthio which is optionally substituted by $E^1$, alkenylthio which is optionally substituted by $E^1$, alkynylthio which is optionally substituted by $E^1$, alkylsulfinyl which is optionally substituted by $E^2$, alkylsulfonyl which is optionally substituted by $E^2$, cycloalkyl which is optionally substituted by J, cycloalkyloxy which is optionally substituted by J, cycloalkylthio which is optionally substituted by J, cyano, nitro, formyl, —$OR^4$, —$SR^5$, —$NR^6$, $R^7$, —$CO_2R^8$, —C(=O)$NR^8R^9$, —$SO_2NR^8R^9$, —CH=$NR^{10}$, or a heterocyclic ring, wherein the heterocyclic ring is optionally substituted by halogen, alkyl, haloalkyl, alkoxy, haloalkoxy, or alkylcarbonyl;
- each of $R^1$ and $R^2$ which are independent of each other, is hydrogen, alkyl, haloalkyl, hydroxyalkyl, alkoxyalkyl, haloalkoxyalkyl, cyanoalkyl, alkoxycarbonylalkyl, alkenyl, haloalkenyl, alkoxyalkenyl, alkynyl, haloalkynyl, alkoxyalkynyl, cycloalkyl, halocycloalkyl, (alkyl)cycloalkyl, (haloalkyl)cycloalkyl, cyano, or —$CO_2R^8$, or $R^1$ and $R^2$ may together form a 3- to 6-membered saturated carbocyclic ring;
- $R^3$ is hydrogen, alkyl which is optionally substituted by $E^1$, alkenyl which is optionally substituted by $E^1$, alkynyl which is optionally substituted by $E^1$, hydroxy, cyanooxy, alkoxy which is optionally substituted by $E^1$, cycloalkyl which is optionally substituted by J, cycloalkyloxy which is optionally substituted by J, cycloalkylthio which is optionally substituted by J, cyano, formyl, —C(=$W^3$)$R^{11}$, —C(=$W^3$)$OR^{12}$, —C(=$W^3$)$SR^{12}$, —C(=$W^3$)$NR^{12}R^{13}$ —S(O)m$R^{12}$, or —S(O)n$NR^{12}R^{13}$;
- $R^4$ is —C(=$W^3$)$R^{12}$, —C(=$W^3$)$OR^{12}$, —C(=$W^3$)$SR^{12}$, —C(=$W^3$)$NR^{12}R^{13}$, —S(O)m$R^{12}$, —S(O)n$NR^{12}R^{13}$, or a heterocyclic ring, wherein the heterocyclic ring is optionally substituted by halogen, alkyl, haloalkyl, alkoxy, haloalkoxy, or alkylcarbonyl;
- $R^5$ is —C(=$W^3$)$R^{12}$, —C(=$W^3$)$OR^{12}$, —C(=$W^3$)$SR^{12}$, —C(=$W^3$)$NR^{12}R^{13}$, or a heterocyclic ring, wherein the heterocyclic ring is optionally substituted by halogen, alkyl, haloalkyl, alkoxy, haloalkoxy, or alkylcarbonyl;
- $R^6$ is hydrogen, alkyl, haloalkyl, alkoxyalkyl, haloalkoxyalkyl, cyanoalkyl, (cycloalkyl)alkyl, cycloalkyl, cyano, —C(=$W^3$)$R^{12}$, —C(=$W^3$)$OR^{12}$, —C(=$W^3$)$SR^{12}$, —C(=$W^3$)$NR^{12}R^{13}$, —S(O)m$R^{12}$, —S(O)n$NR^{12}R^{13}$, or a heterocyclic ring, wherein the heterocyclic ring is optionally substituted by halogen, alkyl, haloalkyl, alkoxy, haloalkoxy, or an alkylcarbonyl;
- $R^7$ is hydrogen, alkyl, haloalkyl, alkoxyalkyl, or haloalkoxyalkyl;
- each of $R^8$ and $R^9$ which are independent of each other, is hydrogen, alkyl, haloalkyl, alkoxyalkyl, or haloalkoxyalkyl, and adjacent $R^8$ and $R^9$ may together form a ring;
- $R^{10}$ is alkyl, wherein the alkyl is optionally substituted by halogen, alkoxy, or haloalkoxy, alkoxy, wherein the alkoxy is optionally substituted by halogen, alkoxy, or haloalkoxy, alkenyloxy, wherein the alkenyloxy is optionally substituted by halogen, alkoxy, or haloalkoxy, alkynyloxy, wherein the alkynyloxy is optionally substituted by halogen, alkoxy, or haloalkoxy, or alkoxycarbonyl, wherein the alkoxycarbonyl is optionally substituted by halogen, alkoxy, or haloalkoxy;
- $R^{11}$ is hydrogen, alkyl which is optionally substituted by $E^3$, phenyl, wherein the phenyl is optionally substituted by halogen, alkyl, haloalkyl, alkoxy, haloalkoxy, or alkylcarbonyl, or a heterocyclic ring, wherein the heterocyclic ring is optionally substituted by halogen, alkyl, haloalkyl, alkoxy, haloalkoxy, or alkylcarbonyl;
- each of $R^{12}$ and $R^{13}$ which are independent of each other, is alkyl which is optionally substituted by $E^3$, alkoxy, haloalkoxy, cycloalkyl which is optionally substituted by J, or phenyl, wherein the phenyl is optionally substituted by halogen, alkyl, haloalkyl, alkoxy, haloalkoxy, or alkylcarbonyl, or adjacent $R^{12}$ and $R^{13}$ may together form a ring;
- each of $W^1$, $W^2$ and $W^3$ which are independent of one another, is oxygen or sulfur;
- each of m and n which are independent of each other, is an integer of from 0 to 2;
- $E^1$ is halogen, hydroxy, alkoxy, haloalkoxy, mercapto, alkylthio, haloalkylthio, alkylsulfonyl, cycloalkyl, amino, monoalkylamino, dialkylamino, cyano, nitro, hydroxycarbonyl, alkoxycarbonyl, alkylcarbonyloxy, trialkylsilyl, or a heterocyclic ring, wherein the heterocyclic ring is optionally substituted by halogen, alkyl, haloalkyl, alkoxy, haloalkoxy, or alkylcarbonyl;

$E^2$ is halogen, hydroxy, alkoxy, haloalkoxy, cycloalkyl, amino, monoalkylamino, dialkylamino, cyano, nitro, hydroxycarbonyl, alkoxycarbonyl, trialkylsilyl, or a heterocyclic ring, wherein the heterocyclic ring is optionally substituted by halogen, alkyl, haloalkyl, alkoxy, haloalkoxy, or alkylcarbonyl;

$E^3$ is halogen, alkoxy, alkylthio, amino, monoalkylamino, dialkylamino, cycloalkyl, cyano, alkoxycarbonyl, haloalkoxy, haloalkylthio, or phenyl, wherein the phenyl is optionally substituted by halogen, alkyl, haloalkyl, alkoxy, haloalkoxy, or alkylcarbonyl; and J is halogen, alkyl, haloalkyl, alkoxy, or haloalkoxy.

2. A method for controlling a plant disease, the method comprising applying, to a plant, an acid amide of formula (I) or a salt thereof, in an amount sufficient to control the plant disease,

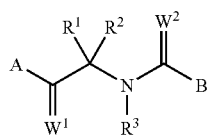

(I)

wherein

A is phenyl which is optionally substituted by X, benzyl which is optionally substituted by X, naphthyl which is optionally substituted by X, heterocyclic ring which is optionally substituted by X, fused heterocyclic ring which is optionally substituted by X, indanyl, wherein the indanyl is optionally substituted by halogen, alkyl, or alkoxy, or tetrahydronaphthyl, wherein the tetrahydronaphthyl is optionally substituted by halogen, alkyl, or alkoxy;

B is heterocyclic ring, excluding pyridyl, which is optionally substituted by Y, fused heterocyclic ring which is optionally substituted by Y, or naphthyl which is optionally substituted by Y;

X is halogen, with the proviso that X is not bromine, alkyl which is optionally substituted by $E^1$, alkenyl which is optionally substituted by $E^1$, alkynyl which is optionally substituted by $E^1$, hydroxy, cyanooxy, alkoxy which is optionally substituted by $E^1$, alkenyloxy which is optionally substituted by $E^1$, alkynyloxy which is optionally substituted by $E^1$, mercapto, cyanothio, alkylthio which is optionally substituted by $E^1$, alkenylthio which is optionally substituted by $E^1$, alkynylthio which is optionally substituted by $E^1$, alkylsulfinyl which is optionally substituted by $E^2$, alkylsulfonyl which is optionally substituted by $E^2$, cycloalkyl which is optionally substituted by J, cycloalkyloxy which is optionally substituted by J, cycloalkylthio which is optionally substituted by J, cyano, nitro, formyl, phenyl which is optionally substituted by Y, phenoxy which is optionally substituted by Y, phenylthio which is optionally substituted by Y, phenylalkyl which is optionally substituted by Y, phenylalkenyl which is optionally substituted by Y, phenylalkynyl which is optionally substituted by Y, phenylalkyloxy which is optionally substituted by Y, phenylalkenyloxy which is optionally substituted by Y, phenylalkynyloxy which is optionally substituted by Y, phenylalkylthio which is optionally substituted by Y, phenylalkenylthio which is optionally substituted by Y, phenylalkynylthio which is optionally substituted by Y, phenylamino which is optionally substituted by Y, $-OR^4$, $-SR^5$, $-NR^6R^7$, $-CO_2R^8$, $-C(=O)NR^8R^9$, $-SO_2NR^8R^9$, $-CH=NR^{10}$, or a heterocyclic ring, wherein the heterocyclic ring is optionally substituted by halogen, alkyl, haloalkyl, alkoxy, haloalkoxy, or alkylcarbonyl;

Y is halogen, alkyl which is optionally substituted by $E^1$, alkenyl which is optionally substituted by $E^1$, alkynyl which is optionally substituted by $E^1$, hydroxy, cyanooxy, alkoxy which is optionally substituted by $E^1$, alkenyloxy which is optionally substituted by $E^1$, alkynyloxy which is optionally substituted by $E^1$, mercapto, cyanothio, alkylthio which is optionally substituted by $E^1$, alkenylthio which is optionally substituted by $E^1$, alkynylthio which is optionally substituted by $E^1$, alkylsulfinyl which is optionally substituted by $E^2$, alkylsulfonyl which is optionally substituted by $E^2$, cycloalkyl which is optionally substituted by J, cycloalkyloxy which is optionally substituted by J, cycloalkylthio which is optionally substituted by J, cyano, nitro, formyl, $-OR^4$, $-SR^5$, $-NR^6R^7$, $-CO_2R^8$, $-C(=O)NR^8R^9$, $-SO_2NR^8R^9$, $-CH=NR^{10}$, or a heterocyclic ring, wherein the heterocyclic ring is optionally substituted by halogen, alkyl, haloalkyl, alkoxy, haloalkoxy, or alkylcarbonyl;

each of $R^1$ and $R^2$ which are independent of each other, is hydrogen, alkyl, haloalkyl, hydroxyalkyl, alkoxyalkyl, haloalkoxyalkyl, cyanoalkyl, alkoxycarbonylalkyl, alkenyl, haloalkenyl, alkoxyalkenyl, alkynyl, haloalkynyl, alkoxyalkynyl, cycloalkyl, halocycloalkyl, (alkyl)cycloalkyl, (haloalkyl)cycloalkyl, cyano, or $-CO_2R^8$, or $R^1$ and $R^2$ may together form a 3- to 6-membered saturated carbocyclic ring;

$R^3$ is hydrogen, alkyl which is optionally substituted by $E^1$, alkenyl which is optionally substituted by $E^1$, alkynyl which is optionally substituted by $E^1$, hydroxy, cyanooxy, alkoxy which is optionally substituted by $E^1$, cycloalkyl which is optionally substituted by J, cycloalkyloxy which is optionally substituted by J, cycloalkylthio which is optionally substituted by J, cyano, formyl, $-C(=W^3)R^{11}$, $-C(=W^3)OR^{12}$, $-C(=W^3)SR^{12}$, $-C(=W^3)NR^{12}R^{13}$, $-S(O)mR^{12}$, or $-S(O)nNR^{12}R^{13}$;

$R^4$ is $-C(=W^3)R^{12}$, $-C(=W^3)OR^{12}$, $-C(=W^3)SR^{12}$, $-C(=W^3)NR^{12}R^{13}$, $-S(O)mR^{12}$, $-S(O)nNR^{12}R^{13}$, or a heterocyclic ring, wherein the heterocyclic ring is optionally substituted by halogen, alkyl, haloalkyl, alkoxy, haloalkoxy, or alkylcarbonyl;

$R^5$ is $-C(=W^3)R^{12}$, $-C(=W^3)OR^{12}$, $-C(=W^3)SR^{12}$, $-C(=W^3)NR^{12}R^{13}$, or a heterocyclic ring, wherein the heterocyclic ring is optionally substituted by halogen, alkyl, haloalkyl, alkoxy, haloalkoxy, or alkylcarbonyl;

$R^6$ is hydrogen, alkyl, haloalkyl, alkoxyalkyl, haloalkoxyalkyl, cyanoalkyl, (cycloalkyl)alkyl, cycloalkyl, cyano, $-C(=W^3)R^{12}$, $-C(=W^3)OR^{12}$, $-C(=W^3)SR^{12}$, $-C(=W^3)NR^{12}R^{13}$, $-S(O)mR^{12}$, $-S(O)nNR^{12}R^{13}$, or a heterocyclic ring, wherein the heterocyclic ring is optionally substituted by halogen, alkyl, haloalkyl, alkoxy, haloalkoxy, or an alkylcarbonyl;

$R^7$ is hydrogen, alkyl, haloalkyl, alkoxyalkyl, or haloalkoxyalkyl;

each of $R^8$ and $R^9$ which are independent of each other, is hydrogen, alkyl, haloalkyl, alkoxyalkyl, or haloalkoxyalkyl, and adjacent $R^8$ and $R^9$ may together form a ring;

R¹⁰ is alkyl, wherein the alkyl is optionally substituted by halogen, alkoxy, or haloalkoxy, alkoxy, wherein the alkoxy is optionally substituted by halogen, alkoxy, or haloalkoxy, alkenyloxy, wherein the alkenyloxy is optionally substituted by halogen, alkoxy, or haloalkoxy, alkynyloxy, wherein the alkynyloxy is optionally substituted by halogen, alkoxy, or haloalkoxy, or alkoxycarbonyl, wherein the alkoxycarbonyl is optionally substituted by halogen, alkoxy, or haloalkoxy;

R¹¹ is hydrogen, alkyl which is optionally substituted by E³, phenyl, wherein the phenyl is optionally substituted by halogen, alkyl, haloalkyl, alkoxy, haloalkoxy, or alkylcarbonyl, or a heterocyclic ring, wherein the heterocyclic ring is optionally substituted by halogen, alkyl, haloalkyl, alkoxy, haloalkoxy, or alkylcarbonyl;

each of R¹² and R¹³ which are independent of each other, is alkyl which is optionally substituted by E³, alkoxy, haloalkoxy, cycloalkyl which is optionally substituted by J, or phenyl, wherein the phenyl is optionally substituted by halogen, alkyl, haloalkyl, alkoxy, haloalkoxy, or alkylcarbonyl, or adjacent R¹² and R¹³ may together form a ring;

each of W¹, W² and W³ which are independent of one another, is oxygen or sulfur;

each of m and n which are independent of each other, is an integer of from 0 to 2;

E¹ is halogen, hydroxy, alkoxy, haloalkoxy, mercapto, alkylthio, haloalkylthio, alkylsulfonyl, cycloalkyl, amino, monoalkylamino, dialkylamino, cyano, nitro, hydroxycarbonyl, alkoxycarbonyl, alkylcarbonyloxy, trialkylsilyl, or a heterocyclic ring, wherein the heterocyclic ring is optionally substituted by halogen, alkyl, haloalkyl, alkoxy, haloalkoxy, or alkylcarbonyl;

E² is halogen, hydroxy, alkoxy, haloalkoxy, cycloalkyl, amino, monoalkylamino, dialkylamino, cyano, nitro, hydroxycarbonyl, alkoxycarbonyl, trialkylsilyl, or a heterocyclic ring, wherein the heterocyclic ring is optionally substituted by halogen, alkyl, haloalkyl, alkoxy, haloalkoxy, or alkylcarbonyl;

E³ is halogen, alkoxy, alkylthio, amino, monoalkylamino, dialkylamino, cycloalkyl, cyano, alkoxycarbonyl, haloalkoxy, haloalkylthio, or phenyl, wherein the phenyl is optionally substituted by halogen, alkyl, haloalkyl, alkoxy, haloalkoxy, or alkylcarbonyl; and J is halogen, alkyl, haloalkyl, alkoxy, or haloalkoxy.

3. A method for protecting a crop plant against fungus or diseases caused by fungus, the method comprising applying, to the crop plant, an acid amide of formula (I) or a salt thereof, in an amount sufficient to protect the crop plant,

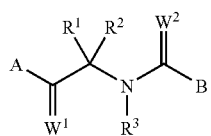

(I)

wherein

A is phenyl which is optionally substituted by X, benzyl which is optionally substituted by X, naphthyl which is optionally substituted by X, heterocyclic ring which is optionally substituted by X, fused heterocyclic ring which is optionally substituted by X, indanyl, wherein the indanyl is optionally substituted by halogen, alkyl, or alkoxy, or tetrahydronaphthyl, wherein the tetrahydronaphthyl is optionally substituted by halogen, alkyl, or alkoxy;

B is heterocyclic ring, excluding pyridyl, which is optionally substituted by Y, fused heterocyclic ring which is optionally substituted by Y, or naphthyl which is optionally substituted by Y;

X is halogen, with the proviso that X is not bromine, alkyl which is optionally substituted by E¹, alkenyl which is optionally substituted by E¹, alkynyl which is optionally substituted by E¹, hydroxy, cyanooxy, alkoxy which is optionally substituted by E¹, alkenyloxy which is optionally substituted by E¹, alkynyloxy which is optionally substituted by E¹, mercapto, cyanothio, alkylthio which is optionally substituted by E¹, alkenylthio which is optionally substituted by E¹, alkynylthio which is optionally substituted by E¹, alkylsulfinyl which is optionally substituted by E², alkylsulfonyl which is optionally substituted by E², cycloalkyl which is optionally substituted by J, cycloalkyloxy which is optionally substituted by J, cycloalkylthio which is optionally substituted by J, cyano, nitro, formyl, phenyl which is optionally substituted by Y, phenoxy which is optionally substituted by Y, phenylthio which is optionally substituted by Y, phenylalkyl which is optionally substituted by Y, phenylalkenyl which is optionally substituted by Y, phenylalkynyl which is optionally substituted by Y, phenylalkyloxy which is optionally substituted by Y, phenylalkenyloxy which is optionally substituted by Y, phenylalkynyloxy which is optionally substituted by Y, phenylalkylthio which is optionally substituted by Y, phenylalkenylthio which is optionally substituted by Y, phenylalkynylthio which is optionally substituted by Y, phenylamino which is optionally substituted by Y, —OR⁴, —SR⁵, —NR⁶R⁷, —CO₂R⁸, —C(=O)NR⁸R⁹, —SO₂NR⁸R⁹, —CH=NR¹⁰, or a heterocyclic ring, wherein the heterocyclic ring is optionally substituted by halogen, alkyl, haloalkyl, alkoxy, haloalkoxy, or alkylcarbonyl;

Y is halogen, alkyl which is optionally substituted by E¹, alkenyl which is optionally substituted by E¹, alkynyl which is optionally substituted by E¹, hydroxy, cyanooxy, alkoxy which is optionally substituted by E¹, alkenyloxy which is optionally substituted by E¹, alkynyloxy which is optionally substituted by E¹, mercapto, cyanothio, alkylthio which is optionally substituted by E¹ alkenylthio which is optionally substituted by E¹, alkynylthio which is optionally substituted by E¹, alkylsulfinyl which is optionally substituted by E², alkylsulfonyl which is optionally substituted by E², cycloalkyl which is optionally substituted by J, cycloalkyloxy which is optionally substituted by J, cycloalkylthio which is optionally substituted by J, cyano, nitro, formyl, —OR⁴, —SR⁵, —NR⁶R⁷, —CO₂R⁸, —C(=O)NR⁸R⁹, —SO₂NR⁸R⁹, —CH=NR¹⁰, or a heterocyclic ring, wherein the heterocyclic ring is optionally substituted by halogen, alkyl, haloalkyl, alkoxy, haloalkoxy, or alkylcarbonyl;

each of R¹ and R² which are independent of each other, is hydrogen, alkyl, haloalkyl, hydroxyalkyl, alkoxyalkyl, haloalkoxyalkyl, cyanoalkyl, alkoxycarbonylalkyl, alkenyl, haloalkenyl, alkoxyalkenyl, alkynyl, haloalkynyl, alkoxyalkynyl, cycloalkyl, halocycloalkyl, (alkyl)cycloalkyl, (haloalkyl)cycloalkyl, cyano, or —CO₂R⁸, or R¹ and R² may together form a 3- to 6-membered saturated carbocyclic ring;

R³ is hydrogen, alkyl which is optionally substituted by E¹, alkenyl which is optionally substituted by E¹, alkynyl which is optionally substituted by E¹, hydroxy, cyanooxy, alkoxy which is optionally substituted by E¹, cycloalkyl which is optionally substituted by J, cycloalkyloxy which is optionally substituted by J, cycloalkylthio which is optionally substituted by J, cyano, formyl, —C(=W³)R¹¹, —C(=W³)OR¹², —C(=W³)SR¹², —C(=W³)NR¹²R¹³, —S(O)mR¹², or —S(O)nNR¹²R¹³;

R⁴ is —C(=W3)R¹², —C(=W³)OR¹², —C(=W³)SR¹², —C(=W³)NR¹²R¹³, —S(O)mR¹², —S(O)nNR¹²R¹³, or a heterocyclic ring, wherein the heterocyclic ring is optionally substituted by halogen, alkyl, haloalkyl, alkoxy, haloalkoxy, or alkylcarbonyl;

R⁵ is —C(=W³)R¹², —C(=W³)OR¹², —C(=W³)SR¹², —C(=W³)NR¹²R¹³, or a heterocyclic ring, wherein the heterocyclic ring is optionally substituted by halogen, alkyl, haloalkyl, alkoxy, haloalkoxy, or alkylcarbonyl;

R⁶ is hydrogen, alkyl, haloalkyl, alkoxyalkyl, haloalkoxyalkyl, cyanoalkyl, (cycloalkyl)alkyl, cycloalkyl, cyano, —C(=W³)R¹², —C(=W³)OR¹², —C(=W³)SR¹², —C(=W³)NR¹²R¹³, —S(O)mR¹², —S(O)nNR¹²R¹³, or a heterocyclic ring, wherein the heterocyclic ring is optionally substituted by halogen, alkyl, haloalkyl, alkoxy, haloalkoxy, or an alkylcarbonyl;

R⁷ is hydrogen, alkyl, haloalkyl, alkoxyalkyl, or haloalkoxyalkyl;

each of R⁸ and R⁹ which are independent of each other, is hydrogen, alkyl, haloalkyl, alkoxyalkyl, or haloalkoxyalkyl, and adjacent R⁸ and R⁹ may together form a ring;

R¹⁰ is alkyl, wherein the alkyl is optionally substituted by halogen, alkoxy, or haloalkoxy, alkoxy, wherein the alkoxy is optionally substituted by halogen, alkoxy, or haloalkoxy, alkenyloxy, wherein the alkenyloxy is optionally substituted by halogen, alkoxy, or haloalkoxy, alkynyloxy, wherein the alkynyloxy is optionally substituted by halogen, alkoxy, or haloalkoxy, or alkoxycarbonyl, wherein the alkoxycarbonyl is optionally substituted by halogen, alkoxy, or haloalkoxy;

R¹¹ is hydrogen, alkyl which is optionally substituted by E³, phenyl, wherein the phenyl is optionally substituted by halogen, alkyl, haloalkyl, alkoxy, haloalkoxy, or alkylcarbonyl, or a heterocyclic ring, wherein the heterocyclic ring is optionally substituted by halogen, alkyl, haloalkyl, alkoxy, haloalkoxy, or alkylcarbonyl;

each of R¹² and R¹³ which are independent of each other, is alkyl which is optionally substituted by E³, alkoxy, haloalkoxy, cycloalkyl which is optionally substituted by J, or phenyl, wherein the phenyl is optionally substituted by halogen, alkyl, haloalkyl, alkoxy, haloalkoxy, or alkylcarbonyl, or adjacent R¹² and R¹³ may together form a ring;

each of W¹, W² and W³ which are independent of one another, is oxygen or sulfur;

each of m and n which are independent of each other, is an integer of from 0 to 2;

E¹ is halogen, hydroxy, alkoxy, haloalkoxy, mercapto, alkylthio, haloalkylthio, alkylsulfonyl, cycloalkyl, amino, monoalkylamino, dialkylamino, cyano, nitro, hydroxycarbonyl, alkoxycarbonyl, alkylcarbonyloxy, trialkylsilyl, or a heterocyclic ring, wherein the heterocyclic ring is optionally substituted by halogen, alkyl, haloalkyl, alkoxy, haloalkoxy, or alkylcarbonyl;

E² is halogen, hydroxy, alkoxy, haloalkoxy, cycloalkyl, amino, monoalkylamino, dialkylamino, cyano, nitro, hydroxycarbonyl, alkoxycarbonyl, trialkylsilyl, or a heterocyclic ring, wherein the heterocyclic ring is optionally substituted by halogen, alkyl, haloalkyl, alkoxy, haloalkoxy, or alkylcarbonyl;

E³ is halogen, alkoxy, alkylthio, amino, monoalkylamino, dialkylamino, cycloalkyl, cyano, alkoxycarbonyl, haloalkoxy, haloalkylthio, or phenyl, wherein the phenyl is optionally substituted by halogen, alkyl, haloalkyl, alkoxy, haloalkoxy, or alkylcarbonyl; and J is halogen, alkyl, haloalkyl, alkoxy, or haloalkoxy.

4. A method for improving a crop yield otherwise limited by the presence of fungus or diseases caused by fungus, the method comprising applying, to the crop, an acid amide of formula (I) or a salt thereof, in an amount sufficient to improve the crop yield,

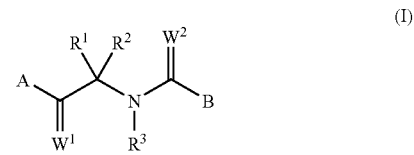

(I)

wherein

A is phenyl which is optionally substituted by X, benzyl which is optionally substituted by X, naphthyl which is optionally substituted by X, heterocyclic ring which is optionally substituted by X, fused heterocyclic ring which is optionally substituted by X, indanyl, wherein the indanyl is optionally substituted by halogen, alkyl, or alkoxy, or tetrahydronaphthyl, wherein the tetrahydronaphthyl is optionally substituted by halogen, alkyl, or alkoxy;

B is heterocyclic ring, excluding pyridyl, which is optionally substituted by Y, fused heterocyclic ring which is optionally substituted by Y, or naphthyl which is optionally substituted by Y;

X is halogen, with the proviso that X is not bromine, alkyl which is optionally substituted by E¹, alkenyl which is optionally substituted by E¹, alkynyl which is optionally substituted by E¹, hydroxy, cyanooxy, alkoxy which is optionally substituted by E¹, alkenyloxy which is optionally substituted by E¹, alkynyloxy which is optionally substituted by E¹, mercapto, cyanothio, alkylthio which is optionally substituted by E¹, alkenylthio which is optionally substituted by E¹, alkynylthio which is optionally substituted by E¹, alkylsulfinyl which is optionally substituted by E², alkylsulfonyl which is optionally substituted by E², cycloalkyl which is optionally substituted by J, cycloalkyloxy which is optionally substituted by J, cycloalkylthio which is optionally substituted by J, cyano, nitro, formyl, phenyl which is optionally substituted by Y, phenoxy which is optionally substituted by Y, phenylthio which is optionally substituted by Y, phenylalkyl which is optionally substituted by Y, phenylalkenyl which is optionally substituted by Y, phenylalkynyl which is optionally substituted by Y, phenylalkyloxy which is optionally substituted by Y, phenylalkenyloxy which is optionally substituted by Y, phenylalkynyloxy which is optionally substituted by Y, phenylalkylthio which is optionally substituted by Y, phenylalkenylthio which is optionally substituted by Y, phenylalkynylthio which is optionally substituted by Y, phenylamino which is optionally substituted by Y, —OR⁴, —SR⁵, —NR⁶R⁷, —CO₂R⁸, —C(=O)NR⁸R⁹, —SO$_2$NR$^8$R$^9$, —CH=NR$^{10}$, or a heterocyclic ring, wherein the heterocyclic ring is optionally substituted by halogen, alkyl, haloalkyl, alkoxy, haloalkoxy, or alkylcarbonyl;

Y is halogen, alkyl which is optionally substituted by E$^1$, alkenyl which is optionally substituted by E$^1$, alkynyl which is optionally substituted by E$^1$, hydroxy, cyanooxy, alkoxy which is optionally substituted by E$^1$, alkenyloxy which is optionally substituted by E$^1$, alkynyloxy which is optionally substituted by E$^1$, mercapto, cyanothio, alkylthio which is optionally substituted by E$^1$, alkenylthio which is optionally substituted by E$^1$, alkynylthio which is optionally substituted by E$^1$, alkylsulfinyl which is optionally substituted by E$^2$, alkylsulfonyl which is optionally substituted by E$^2$, cycloalkyl which is optionally substituted by J, cycloalkyloxy which is optionally substituted by J, cycloalkylthio which is optionally substituted by J, cyano, nitro, formyl, —OR$^4$, —SR$^5$, —NR$^6$R$^7$, —CO$_2$R$^8$, —C(=O)NR$^8$R$^9$, —SO$_2$NR$^8$R$^9$, —CH=NR$^{10}$, or a heterocyclic ring, wherein the heterocyclic ring is optionally substituted by halogen, alkyl, haloalkyl, alkoxy, haloalkoxy, or alkylcarbonyl;

each of R$^1$ and R$^2$ which are independent of each other, is hydrogen, alkyl, haloalkyl, hydroxyalkyl, alkoxyalkyl, haloalkoxyalkyl, cyanoalkyl, alkoxycarbonylalkyl, alkenyl, haloalkenyl, alkoxyalkenyl, alkynyl, haloalkynyl, alkoxyalkynyl, cycloalkyl, halocycloalkyl, (alkyl)cycloalkyl, (haloalkyl)cycloalkyl, cyano, or —CO$_2$R$^8$, or R$^1$ and R$^2$ may together form a 3- to 6-membered saturated carbocyclic ring;

R$^3$ is hydrogen, alkyl which is optionally substituted by E$^1$, alkenyl which is optionally substituted by E$^1$, alkynyl which is optionally substituted by E$^1$, hydroxy, cyanooxy, alkoxy which is optionally substituted by E$^1$, cycloalkyl which is optionally substituted by J, cycloalkyloxy which is optionally substituted by J, cycloalkylthio which is optionally substituted by J, cyano, formyl, —C(=W$^3$)R$^{11}$, —C(=W$^3$)OR$^{12}$, —C(=W$^3$)SR$^{12}$, —C(=W$^3$)NR$^{12}$R$^{13}$, —S(O)mR$^{12}$, or —S(O)nNR$^{12}$R$^{13}$;

R$^4$ is —C(=W$^3$)R$^{12}$, —C(=W$^3$)OR$^{12}$, —C(=W$^3$)SR$^{12}$, —C(=W$^3$)NR$^{12}$R$^{13}$, —S(O)mR$^{12}$, —S(O)nNR$^{12}$R$^{13}$, or a heterocyclic ring, wherein the heterocyclic ring is optionally substituted by halogen, alkyl, haloalkyl, alkoxy, haloalkoxy, or alkylcarbonyl;

R$^5$ is —C(=W$^3$)R$^{12}$, —C(=W$^3$)OR$^{12}$, —C(=W$^3$)SR$^2$, —C(=W$^3$)NR$^{12}$R$^{13}$, or a heterocyclic ring, wherein the heterocyclic ring is optionally substituted by halogen, alkyl, haloalkyl, alkoxy, haloalkoxy, or alkylcarbonyl;

R$^6$ is hydrogen, alkyl, haloalkyl, alkoxyalkyl, haloalkoxyalkyl, cyanoalkyl, (cycloalkyl)alkyl, cycloalkyl, cyano, —C(=W$^3$)R$^{12}$, —C(=W$^3$)OR$^{12}$, —C(=W$^3$)SR$^{12}$, —C(=W$^3$)NR$^{12}$R$^{13}$, —S(O)mR$^{12}$, —S(O)nNR$^{12}$R$^{13}$, or a heterocyclic ring, wherein the heterocyclic ring is optionally substituted by halogen, alkyl, haloalkyl, alkoxy, haloalkoxy, or an alkylcarbonyl;

R$^7$ is hydrogen, alkyl, haloalkyl, alkoxyalkyl, or haloalkoxyalkyl;

each of R$^8$ and R$^9$ which are independent of each other, is hydrogen, alkyl, haloalkyl, alkoxyalkyl, or haloalkoxyalkyl, and adjacent R$^8$ and R$^9$ may together form a ring;

R$^{10}$ is alkyl, wherein the alkyl is optionally substituted by halogen, alkoxy, or haloalkoxy, alkoxy, wherein the alkoxy is optionally substituted by halogen, alkoxy, or haloalkoxy, alkenyloxy, wherein the alkenyloxy is optionally substituted by halogen, alkoxy, or haloalkoxy, alkynyloxy, wherein the alkynyloxy is optionally substituted by halogen, alkoxy, or haloalkoxy, or alkoxycarbonyl, wherein the alkoxycarbonyl is optionally substituted by halogen, alkoxy, or haloalkoxy;

R$^{11}$ is hydrogen, alkyl which is optionally substituted by E$^3$, phenyl, wherein the phenyl is optionally substituted by halogen, alkyl, haloalkyl, alkoxy, haloalkoxy, or alkylcarbonyl, or a heterocyclic ring, wherein the heterocyclic ring is optionally substituted by halogen, alkyl, haloalkyl, alkoxy, haloalkoxy, or alkylcarbonyl;

each of R$^{12}$ and R$^{13}$ which are independent of each other, is alkyl which is optionally substituted by E$^3$, alkoxy, haloalkoxy, cycloalkyl which is optionally substituted by J, or phenyl, wherein the phenyl is optionally substituted by halogen, alkyl, haloalkyl, alkoxy, haloalkoxy, or alkylcarbonyl, or adjacent R$^{12}$ and R$^{13}$ may together form a ring;

each of W$^1$, W$^2$ and W$^3$ which are independent of one another, is oxygen or sulfur;

each of m and n which are independent of each other, is an integer of from 0 to 2;

E$^1$ is halogen, hydroxy, alkoxy, haloalkoxy, mercapto, alkylthio, haloalkylthio, alkylsulfonyl, cycloalkyl, amino, monoalkylamino, dialkylamino, cyano, nitro, hydroxycarbonyl, alkoxycarbonyl, alkylcarbonyloxy, trialkylsilyl, or a heterocyclic ring, wherein the heterocyclic ring is optionally substituted by halogen, alkyl, haloalkyl, alkoxy, haloalkoxy, or alkylcarbonyl;

E$^2$ is halogen, hydroxy, alkoxy, haloalkoxy, cycloalkyl, amino, monoalkylamino, dialkylamino, cyano, nitro, hydroxycarbonyl, alkoxycarbonyl, trialkylsilyl, or a heterocyclic ring, wherein the heterocyclic ring is optionally substituted by halogen, alkyl, haloalkyl, alkoxy, haloalkoxy, or alkylcarbonyl;

E$^3$ is halogen, alkoxy, alkylthio, amino, monoalkylamino, dialkylamino, cycloalkyl, cyano, alkoxycarbonyl, haloalkoxy, haloalkylthio, or phenyl, wherein the phenyl is optionally substituted by halogen, alkyl, haloalkyl, alkoxy, haloalkoxy, or alkylcarbonyl; and J is halogen, alkyl, haloalkyl, alkoxy, or haloalkoxy.

5. The method according to claim 1, wherein X is halogen, alkyl, wherein the alkyl is optionally substituted by halogen, hydroxy, alkoxy, haloalkoxy, alkylthio, alkylsulfonyl, cycloalkyl, amino, monoalkylamino, dialkylamino, cyano, alkoxycarbonyl, or alkylcarbonyloxy, alkenyl, haloalkenyl, alkynyl, wherein the alkynyl is optionally substituted by halogen, hydroxy, alkoxy, amino, hydroxycarbonyl, alkoxycarbonyl, or trialkylsilyl, hydroxy, cyanooxy, alkoxy, wherein the alkoxy is optionally substituted by halogen, alkoxy, haloalkoxy, alkylthio, cycloalkyl, monoalkylamino, dialkylamino, cyano, or a heterocyclic ring, alkenyloxy, haloalkenyloxy, alkynyloxy, haloalkynyloxy, alkylthio, wherein the alkylthio is optionally substituted by halogen, cycloalkyl, or cyano, alkenylthio, haloalkenylthio, alkynylthio, haloalkynylthio, alkylsulfinyl, haloalkylsulfinyl, alkylsulfonyl, haloalkylsulfonyl, cycloalkyl which is optionally substituted by halogen, cycloalkyloxy which is optionally substituted by halogen, cycloalkylthio which is optionally substituted by halogen, cyano, nitro, formyl, phenyl, wherein the phenyl is optionally substituted by halogen, alkyl, haloalkyl, or alkoxy, phenoxy which is optionally substituted by alkyl, phenylthio which is optionally substituted by alkyl, phenylalkyl which is optionally substituted by alkyl, phenylalkenyl which is optionally substituted by alkyl, phenylalkynyl which is optionally substituted by alkyl, phenylalkyloxy which is optionally substituted by alkyl, phenylalkenyloxy which is optionally substituted by alkyl, phenylalkynyloxy which is optionally substituted by alkyl, phenylamino which is optionally substituted by alkyl, —OR$^4$, —SR$^5$, —NR$^6$R$^7$, —CO$_2$R$^8$, —C(=O)NR$^8$R$^9$, —SO$_2$NR$^8$R$^9$, —CH=NR$^{10}$, or a heterocyclic ring, wherein the heterocyclic ring is optionally substituted by halogen, alkyl, or alkylcarbonyl;

Y is halogen, alkyl, wherein the alkyl is optionally substituted by halogen, alkoxy, haloalkoxy, amino, monoalkylamino, or dialkylamino, alkenyl, alkynyl, hydroxy, alkoxy, haloalkoxy, alkylthio, haloalkylthio, alkylsulfinyl, haloalkylsulfinyl, alkylsulfonyl, haloalkylsulfonyl, cycloalkyl, cyano, nitro, formyl, —OR$^4$, —NR$^6$R$^7$, —CO$_2$R$^8$, —C(=O)NR$^8$R$^9$, —SO$_2$NR$^8$R$^9$, or —CH=NR$^{10}$;

each of R$^1$ and R$^2$ which are independent of each other, is alkyl, haloalkyl, alkoxyalkyl, alkenyl, alkynyl, or cycloalkyl, or R$^1$ and R$^2$ may together form a 3- to 6-membered saturated carbocyclic ring; and R$^3$ is hydrogen, alkyl, wherein the alkyl is optionally substituted by halogen, alkoxy, haloalkoxy, alkylthio, amino, monoalkylamino, dialkylamino, or cyano, alkenyl, alkynyl, hydroxy, alkoxy, haloalkoxy, cycloalkyl, cycloalkyloxy, cyano, formyl, —C(=W$^3$)R$^{11}$, —C(=W$^3$)OR$^{12}$, or —S(O)mR$^{12}$.

6. The method according to claim 2, wherein X is halogen, alkyl, wherein the alkyl is optionally substituted by halogen, hydroxy, alkoxy, haloalkoxy, alkylthio, alkylsulfonyl, cycloalkyl, amino, monoalkylamino, dialkylamino, cyano, alkoxycarbonyl, or alkylcarbonyloxy, alkenyl, haloalkenyl, alkynyl, wherein the alkynyl is optionally substituted by halogen, hydroxy, alkoxy, amino, hydroxycarbonyl, alkoxycarbonyl, or trialkylsilyl, hydroxy, cyanooxy, alkoxy, wherein the alkoxy is optionally substituted by halogen, alkoxy, haloalkoxy, alkylthio, cycloalkyl, monoalkylamino, dialkylamino, cyano, or a heterocyclic ring, alkenyloxy, haloalkenyloxy, alkynyloxy, haloalkynyloxy, alkylthio, wherein the alkylthio is optionally substituted by halogen, cycloalkyl, or cyano, alkenylthio, haloalkenylthio, alkynylthio, haloalkynylthio, alkylsulfinyl, haloalkylsulfinyl, alkylsulfonyl, haloalkylsulfonyl, cycloalkyl which is optionally substituted by halogen, cycloalkyloxy which is optionally substituted by halogen, cycloalkylthio which is optionally substituted by halogen, cyano, nitro, formyl, phenyl, wherein the phenyl is optionally substituted by halogen, alkyl, haloalkyl, or alkoxy, phenoxy which is optionally substituted by alkyl, phenylthio which is optionally substituted by alkyl, phenylalkyl which is optionally substituted by alkyl, phenylalkenyl which is optionally substituted by alkyl, phenylalkynyl which is optionally substituted by alkyl, phenylalkyloxy which is optionally substituted by alkyl, phenylalkenyloxy which is optionally substituted by alkyl, phenylalkynyloxy which is optionally substituted by alkyl, phenylamino which is optionally substituted by alkyl, —OR$^4$, —SR$^5$, —NR$^6$R$^7$, —CO$_2$R$^8$, —C(=O)NR$^8$R$^9$, —SO$_2$NR$^8$R$^9$, —CH=NR$^{10}$, or a heterocyclic ring, wherein the heterocyclic ring is optionally substituted by halogen, alkyl, or alkylcarbonyl;

Y is halogen, alkyl, wherein the alkyl is optionally substituted by halogen, alkoxy, haloalkoxy, amino, monoalkylamino, or dialkylamino, alkenyl, alkynyl, hydroxy, alkoxy, haloalkoxy, alkylthio, haloalkylthio, alkylsulfinyl, haloalkylsulfinyl, alkylsulfonyl, haloalkylsulfonyl, cycloalkyl, cyano, nitro, formyl, —OR$^4$, —NR$^6$R$^7$, —CO$_2$R$^8$, —C(=O)NR$^8$R$^9$, —SO$_2$NR$^8$R$^9$, or —CH=NR$^{10}$;

each of R$^1$ and R$^2$ which are independent of each other, is alkyl, haloalkyl, alkoxyalkyl, alkenyl, alkynyl, or cycloalkyl, or R$^1$ and R$^2$ may together form a 3- to 6-membered saturated carbocyclic ring; and R$^3$ is hydrogen, alkyl, wherein the alkyl is optionally substituted by halogen, alkoxy, haloalkoxy, alkylthio, amino, monoalkylamino, dialkylamino, or cyano, alkenyl, alkynyl, hydroxy, alkoxy, haloalkoxy, cycloalkyl, cycloalkyloxy, cyano, formyl, —C(=W$^3$)R$^{11}$, —C(=W$^3$)OR$^{12}$, or —S(O)mR$^{12}$.

7. The method according to claim 3, wherein X is halogen, alkyl, wherein the alkyl is optionally substituted by halogen, hydroxy, alkoxy, haloalkoxy, alkylthio, alkylsulfonyl, cycloalkyl, amino, monoalkylamino, dialkylamino, cyano, alkoxycarbonyl, or alkylcarbonyloxy, alkenyl, haloalkenyl, alkynyl, wherein the alkynyl is optionally substituted by halogen, hydroxy, alkoxy, amino, hydroxycarbonyl, alkoxycarbonyl, or trialkylsilyl, hydroxy, cyanooxy, alkoxy, wherein the alkoxy is optionally substituted by halogen, alkoxy, haloalkoxy, alkylthio, cycloalkyl, monoalkylamino, dialkylamino, cyano, or a heterocyclic ring, alkenyloxy, haloalkenyloxy, alkynyloxy, haloalkynyloxy, alkylthio, wherein the alkylthio is optionally substituted by halogen, cycloalkyl, or cyano, alkenylthio, haloalkenylthio, alkynylthio, haloalkynylthio, alkylsulfinyl, haloalkylsulfinyl, alkylsulfonyl, haloalkylsulfonyl, cycloalkyl which is optionally substituted by halogen, cycloalkyloxy which is optionally substituted by halogen, cycloalkylthio which is optionally substituted by halogen, cyano, nitro, formyl, phenyl, wherein the phenyl is optionally substituted by halogen, alkyl, haloalkyl, or alkoxy, phenoxy which is optionally substituted by alkyl, phenylthio which is optionally substituted by alkyl, phenylalkyl which is optionally substituted by alkyl, phenylalkenyl which is optionally substituted by alkyl, phenylalkynyl which is optionally substituted by alkyl, phenylalkyloxy which is optionally substituted by alkyl, phenylalkenyloxy which is optionally substituted by alkyl, phenylalkynyloxy which is optionally substituted by alkyl, phenylamino which is optionally substituted by alkyl, —OR$^4$, —SR$^5$, —NR$^6$R$^7$, —CO$_2$R$^8$, —C(=O)NR$^8$R$^9$, —SO$_2$NR$^8$R$^9$, —CH=NR$^{10}$, or a heterocyclic ring, wherein the heterocyclic ring is optionally substituted by halogen, alkyl, or alkylcarbonyl;

Y is halogen, alkyl, wherein the alkyl is optionally substituted by halogen, alkoxy, haloalkoxy, amino, monoalkylamino, or dialkylamino, alkenyl, alkynyl, hydroxy, alkoxy, haloalkoxy, alkylthio, haloalkylthio, alkylsulfinyl, haloalkylsulfinyl, alkylsulfonyl, haloalkylsulfonyl, cycloalkyl, cyano, nitro, formyl, —OR$^4$, —NR$^6$R$^7$, —CO$_2$R$^8$, —C(=O)NR$^8$R$^9$, —SO$_2$NR$^8$R$^9$, or —CH=NR$^{10}$;

each of R$^1$ and R$^2$ which are independent of each other, is alkyl, haloalkyl, alkoxyalkyl, alkenyl, alkynyl, or cycloalkyl, or R$^1$ and R$^2$ may together form a 3- to 6-membered saturated carbocyclic ring; and R$^3$ is hydrogen, alkyl, wherein the alkyl is optionally substituted by halogen, alkoxy, haloalkoxy, alkylthio, amino, monoalkylamino, dialkylamino, or cyano, alkenyl, alkynyl, hydroxy, alkoxy, haloalkoxy, cycloalkyl, cycloalkyloxy, cyano, formyl, —C(=W$^3$)R$^{11}$, —C(=W$^3$)OR$^{12}$, or —S(O)mR$^{12}$.

8. The method according to claim 4, wherein X is halogen, alkyl, wherein the alkyl is optionally substituted by halogen, hydroxy, alkoxy, haloalkoxy, alkylthio, alkylsulfonyl, cycloalkyl, amino, monoalkylamino, dialkylamino, cyano, alkoxycarbonyl, or alkylcarbonyloxy, alkenyl, haloalkenyl, alkynyl, wherein the alkynyl is optionally substituted by halogen, hydroxy, alkoxy, amino, hydroxycarbonyl, alkoxycarbonyl, or trialkylsilyl, hydroxy, cyanooxy, alkoxy, wherein the alkoxy is optionally substituted by halogen, alkoxy, haloalkoxy, alkylthio, cycloalkyl, monoalkylamino, dialkylamino, cyano, or a heterocyclic ring, alkenyloxy, haloalkenyloxy, alkynyloxy, haloalkynyloxy, alkylthio, wherein the alkylthio is optionally substituted by halogen, cycloalkyl, or cyano, alkenylthio, haloalkenylthio, alkynylthio, haloalkynylthio, alkylsulfinyl, haloalkylsulfinyl, alkylsulfonyl, haloalkylsulfonyl, cycloalkyl which is optionally substituted by halogen, cycloalkyloxy which is optionally substituted by halogen, cycloalkylthio which is optionally substituted by halogen, cyano, nitro, formyl, phenyl, wherein the phenyl is optionally substituted by halogen, alkyl, haloalkyl, or alkoxy, phenoxy which is optionally substituted by alkyl, phenylthio which is optionally substituted by alkyl, phenylalkyl which is optionally substituted by alkyl, phenylalkenyl which is optionally substituted by alkyl, phenylalkynyl which is optionally substituted by alkyl, phenylalkyloxy which is optionally substituted by alkyl, phenylalkenyloxy which is optionally substituted by alkyl, phenylalkynyloxy which is optionally substituted by alkyl, phenylamino which is optionally substituted by alkyl, —$OR^4$, —$SR^5$, —$NR^6R^7$, —$CO_2R^8$, —$C(=O)NR^8R^9$, —$SO_2NR^8R^9$, —$CH=NR^{10}$, or a heterocyclic ring, wherein the heterocyclic ring is optionally substituted by halogen, alkyl, or alkylcarbonyl;

Y is halogen, alkyl, wherein the alkyl is optionally substituted by halogen, alkoxy, haloalkoxy, amino, monoalkylamino, or dialkylamino, alkenyl, alkynyl, hydroxy, alkoxy, haloalkoxy, alkylthio, haloalkylthio, alkylsulfinyl, haloalkylsulfinyl, alkylsulfonyl, haloalkylsulfonyl, cycloalkyl, cyano, nitro, formyl, —$OR^4$, —$NR^6R^7$, —$CO_2R^8$, —$C(=O)NR^8R^9$, —$SO_2NR^8R^9$, or —$CH=NR^{10}$;

each of $R^1$ and $R^2$ which are independent of each other, is alkyl, haloalkyl, alkoxyalkyl, alkenyl, alkynyl, or cycloalkyl, or $R^1$ and $R^2$ may together form a 3- to 6-membered saturated carbocyclic ring; and $R^3$ is hydrogen, alkyl, wherein the alkyl is optionally substituted by halogen, alkoxy, haloalkoxy, alkylthio, amino, monoalkylamino, dialkylamino, or cyano, alkenyl, alkynyl, hydroxy, alkoxy, haloalkoxy, cycloalkyl, cycloalkyloxy, cyano, formyl, —$C(=W^3)R^{11}$, —$C(=W^3)OR^{12}$, or —$S(O)mR^{12}$.

9. The method according to claim 5, wherein

X is halogen, alkyl, haloalkyl, alkoxyalkyl, dialkylaminoalkyl, alkynyl, trialkylsilylalkynyl, hydroxy, alkoxy, haloalkoxy, alkoxyalkoxy, cycloalkyl, nitro, phenyl, phenylalkynyl, pyridyloxy which is optionally substituted by haloalkyl, alkylcarbonyloxy, alkylsulfonyloxy, or a heterocyclic ring, wherein the heterocyclic ring is optionally substituted by halogen, alkyl, or alkylcarbonyl;

Y is halogen, alkyl, haloalkyl, alkoxy, haloalkoxy, cycloalkyl, or formyl;

each of $R^1$ and $R^2$ which are independent of each other, is alkyl;

$R^3$ is hydrogen, alkyl, alkylcarbonyl, or alkoxycarbonyl; and each of $W^1$ and $W^2$ which are independent of each other, is oxygen or sulfur.

10. The method according to claim 6, wherein

X is halogen, alkyl, haloalkyl, alkoxyalkyl, dialkylaminoalkyl, alkynyl, trialkylsilylalkynyl, hydroxy, alkoxy, haloalkoxy, alkoxyalkoxy, cycloalkyl, nitro, phenyl, phenylalkynyl, pyridyloxy which is optionally substituted by haloalkyl, alkylcarbonyloxy, alkylsulfonyloxy, or a heterocyclic ring, wherein the heterocyclic ring is optionally substituted by halogen, alkyl, or alkylcarbonyl;

Y is halogen, alkyl, haloalkyl, alkoxy, haloalkoxy, cycloalkyl, or formyl;

each of $R^1$ and $R^2$ which are independent of each other, is alkyl;

$R^3$ is hydrogen, alkyl, alkylcarbonyl, or alkoxycarbonyl; and each of $W^1$ and $W^2$ which are independent of each other, is oxygen or sulfur.

11. The method according to claim 7, wherein

X is halogen, alkyl, haloalkyl, alkoxyalkyl, dialkylaminoalkyl, alkynyl, trialkylsilylalkynyl, hydroxy, alkoxy, haloalkoxy, alkoxyalkoxy, cycloalkyl, nitro, phenyl, phenylalkynyl, pyridyloxy which is optionally substituted by haloalkyl, alkylcarbonyloxy, alkylsulfonyloxy, or a heterocyclic ring, wherein the heterocyclic ring is optionally substituted by halogen, alkyl, or alkylcarbonyl;

Y is halogen, alkyl, haloalkyl, alkoxy, haloalkoxy, cycloalkyl, or formyl;

each of $R^1$ and $R^2$ which are independent of each other, is alkyl;

$R^3$ is hydrogen, alkyl, alkylcarbonyl, or alkoxycarbonyl; and each of $W^1$ and $W^2$ which are independent of each other, is oxygen or sulfur.

12. The method according to claim 8, wherein

X is halogen, alkyl, haloalkyl, alkoxyalkyl, dialkylaminoalkyl, alkynyl, trialkylsilylalkynyl, hydroxy, alkoxy, haloalkoxy, alkoxyalkoxy, cycloalkyl, nitro, phenyl, phenylalkynyl, pyridyloxy which is optionally substituted by haloalkyl, alkylcarbonyloxy, alkylsulfonyloxy, or a heterocyclic ring, wherein the heterocyclic ring is optionally substituted by halogen, alkyl, or alkylcarbonyl;

Y is halogen, alkyl, haloalkyl, alkoxy, haloalkoxy, cycloalkyl, or formyl;

each of $R^1$ and $R^2$ which are independent of each other, is alkyl;

$R^3$ is hydrogen, alkyl, alkylcarbonyl, or alkoxycarbonyl; and each of $W^1$ and $W^2$ which are independent of each other, is oxygen or sulfur.

13. The method according to claim 9, wherein each of $W^1$ and $W^2$ is oxygen.

14. The method according to claim 10, wherein each of $W^1$ and $W^2$ is oxygen.

15. The method according to claim 11, wherein each of $W^1$ and $W^2$ is oxygen.

16. The method according to claim 12, wherein each of $W^1$ and $W^2$ is oxygen.

17. The method according to claim 9, wherein

X is halogen, alkyl, haloalkyl, alkynyl, hydroxy, alkoxy, haloalkoxy, alkoxyalkoxy, cycloalkyl, nitro, phenylalkyl, pyridyloxy which is optionally substituted by haloalkyl, alkylcarbonyloxy, or a heterocyclic ring, wherein the heterocyclic ring is optionally substituted by halogen, alkyl, or alkylcarbonyl;

Y is halogen, alkyl, haloalkyl, or alkoxy;

$R^3$ is hydrogen, alkylcarbonyl, or alkoxycarbonyl; and each of $W^1$ and $W^2$ is oxygen.

18. The method according to claim 10, wherein

X is halogen, alkyl, haloalkyl, alkynyl, hydroxy, alkoxy, haloalkoxy, alkoxyalkoxy, cycloalkyl, nitro, phenylalkyl, pyridyloxy which is optionally substituted by haloalkyl, alkylcarbonyloxy, or a heterocyclic ring, wherein the heterocyclic ring is optionally substituted by halogen, alkyl, or alkylcarbonyl;

Y is halogen, alkyl, haloalkyl, or alkoxy;
$R^3$ is hydrogen, alkylcarbonyl, or alkoxycarbonyl; and
each of $W^1$ and $W^2$ is oxygen.

19. The method according to claim 11, wherein
X is halogen, alkyl, haloalkyl, alkynyl, hydroxy, alkoxy, haloalkoxy, alkoxyalkoxy, cycloalkyl, nitro, phenylalkyl, pyridyloxy which is optionally substituted by haloalkyl, alkylcarbonyloxy, or a heterocyclic ring, wherein the heterocyclic ring is optionally substituted by halogen, alkyl, or alkylcarbonyl;
Y is halogen, alkyl, haloalkyl, or alkoxy;
$R^3$ is hydrogen, alkylcarbonyl, or alkoxycarbonyl; and
each of $W^1$ and $W^2$ is oxygen.

20. The method according to claim 12, wherein
X is halogen, alkyl, haloalkyl, alkynyl, hydroxy, alkoxy, haloalkoxy, alkoxyalkoxy, cycloalkyl, nitro, phenylalkyl, pyridyloxy which is optionally substituted by haloalkyl, alkylcarbonyloxy, or a heterocyclic ring, wherein the heterocyclic ring is optionally substituted by halogen, alkyl, or alkylcarbonyl;
Y is halogen, alkyl, haloalkyl, or alkoxy;
$R^3$ is hydrogen, alkylcarbonyl, or alkoxycarbonyl; and
each of $W^1$ and $W^2$ is oxygen.

* * * * *